(12) United States Patent
Benedini et al.

(10) Patent No.: US 8,933,062 B2
(45) Date of Patent: Jan. 13, 2015

(54) NITRIC OXIDE RELEASING STEROIDS

(75) Inventors: Francesca Benedini, San Donato Milanese (IT); Stefano Biondi, Pero (IT); Ennio Ongini, Segrate (IT)

(73) Assignee: Nicox S.A., Valbonne (FR)

( * ) Notice: Subject to any disclaimer, the term of this patent is extended or adjusted under 35 U.S.C. 154(b) by 838 days.

(21) Appl. No.: 12/525,970

(22) PCT Filed: Jan. 28, 2008

(86) PCT No.: PCT/EP2008/050938
§ 371 (c)(1),
(2), (4) Date: Sep. 30, 2009

(87) PCT Pub. No.: WO2008/095806
PCT Pub. Date: Aug. 14, 2008

(65) Prior Publication Data
US 2010/0093685 A1    Apr. 15, 2010

Related U.S. Application Data

(60) Provisional application No. 60/899,376, filed on Feb. 5, 2007, provisional application No. 60/929,456, filed on Jun. 28, 2007.

(51) Int. Cl.
| | | |
|---|---|---|
| A61K 31/58 | (2006.01) | |
| A61K 31/56 | (2006.01) | |
| C07J 7/00 | (2006.01) | |
| C07J 71/00 | (2006.01) | |
| C07J 41/00 | (2006.01) | |

(52) U.S. Cl.
CPC .................................... C07J 41/005 (2013.01)
USPC ............. 514/174; 514/181; 540/67; 552/574

(58) Field of Classification Search
USPC ...................... 514/174, 181; 540/67; 552/574
See application file for complete search history.

(56) References Cited

U.S. PATENT DOCUMENTS

| | | | | |
|---|---|---|---|---|
| 6,610,676 B1 * | 8/2003 | Del Soldato | ................... | 514/178 |
| 6,909,007 B1 * | 6/2005 | del Soldato | ................... | 552/551 |
| 7,056,905 B2 * | 6/2006 | Del Soldato | ................... | 514/178 |
| 7,157,450 B2 * | 1/2007 | Del Soldato | ................... | 514/179 |

FOREIGN PATENT DOCUMENTS

| | | |
|---|---|---|
| EP | 1 336 602 A1 | 8/2003 |
| WO | WO 98/15568 A2 | 4/1998 |
| WO | WO 00/61604 A2 | 10/2000 |
| WO | WO 03/064443 A2 | 8/2003 |
| WO | WO 2007/025632 A2 | 3/2007 |

OTHER PUBLICATIONS

Dorwald F. A, . Side Reactions in Organic Synthesis, 2005, Wiley: VCH, Weinheim p. IX of Preface.*

Mark J. Paul-Clark et al. (Proc Natl Acad Sci U S A. Feb. 5, 2002; 99(3): 1677-1682. ).*
Baraldi, Pier Giovanni et al.; "Synthesis of Nitro Esters of Prednisolone, New Compounds Combining Pharmacological Properties of Both Glucocorticoids and Nitric Oxide"; Journal of Medicinal Chemistry; 47(3); 711-719 Coden: JMCMAR; ISSN: 0022-2623; 2004; p. 712; XP002475140; figure 1.
Perretti, M. et al.; "Generation of innovative anti-inflammatory and anti-arthritic glucocorticoid derivatives that release NO: the nitrosteroids"; Digestive and Liver Disease, 35 (Suppl. 2); S41-S48 Coden: DLDIFK; ISSN: 1590-8658; 2003; XP002475141; p. S43; figure 2.

* cited by examiner

*Primary Examiner* — Sabiha N Qazi
(74) *Attorney, Agent, or Firm* — Arent Fox LLP

(57) ABSTRACT

The invention relates to nitrooxyderivative of corticosteroids of general formula (I) and pharmaceutically acceptable salts or stereoisomers thereof $$R—(Z)_a—R_x \quad (I)$$

wherein R is the corticosteroid residue of formula (II):

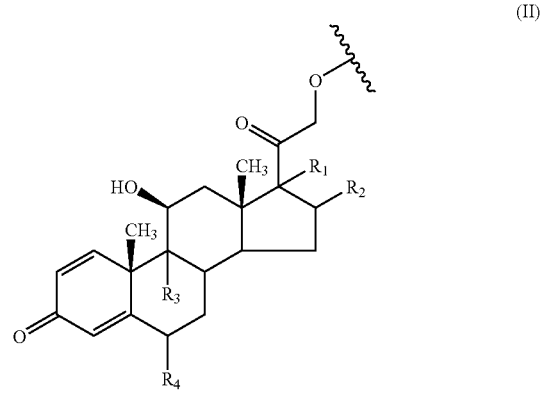

wherein:
$R_1$ is OH, $R_2$—$CH_3$, or $R_1$ and $R_2$ are taken together to form a group of formula (III)

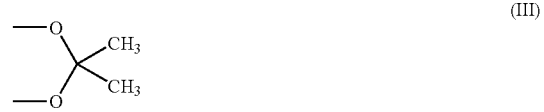

$R_3$ is Cl or F;
$R_4$ is H or F;
wherein $R_1$, $R_2$, $R_3$ and $R_4$ can be linked to the correspondent carbon atoms of the steroidal structure in position α or β;
with the proviso that:
when $R_1$ and $R_2$ are the group of formula (III) then $R_3$ is F and $R_4$ is H or F;
The compounds are useful in the treatment of respiratory diseases, inflammatory diseases, dermatological diseases and ocular diseases.

7 Claims, No Drawings

NITRIC OXIDE RELEASING STEROIDS

CROSS-REFERENCE TO RELATED APPLICATION

This application is a National Stage entry of International Application No. PCT/EP2008/050938, filed Jan. 28, 2008, which claims benefit of U.S. Provisional Nos. 60/929,456 filed Jun. 28, 2007 and 60/899,376 Feb. 5, 2007. The disclosures of the prior applications are hereby incorporated in its entirety by reference.

FIELD OF THE INVENTION

The present invention relates to steroidal compounds having an improved pharmacological activity and lower side effects, to a process for their preparation and to pharmaceutical formulation containing them.

The compounds of the present invention may be used, as drugs having antiinflammatory activity at peripheral level, for the therapy of respiratory diseases such as asthma and COPD, in ocular disease therapies such as ocular hypertension, age-related macular degeneration, diabetic macular edema, diabetic retinopathy, hypertensive retinopathy and retinal vasculopathies, or in dermatological disease therapies such asdermatosis, atopic dermatitis, inflammation, eczema, erythema, papulation, scaling, erosion, oozing, crusting, pruritis, psoriasis, epidermalysis bullosa, erythema, hidradenitis suppurative, warts, diaper rash, jock itch.

In particular the compounds of the present invention are useful in ocular disease therapies.

BACKGROUND OF THE INVENTION

In the prior art nitrooxy derivatives of steroids, which are usable also as cardiovascular agents for the coronary insufficiency or angina pectoris therapy, are described.

For example, German patent DE 2,222,491 describes the preparation of pregnane derivatives having in position 21 the —$CH_2$—O—$NO_2$ group. In said patent it is stated that said derivatives have a cardiotropic activity. This activity represents a drawback for said compounds, since they modify the cardiac frequency.

U.S. Pat. No. 3,494,941 describes steroid derivatives from 3-hydroxy-extrane or from extr-4 en-3 one, used as vasodilators in the treatment of cardiac affections such as coronary insufficiency and angina pectoris. In the structure of said compounds a $ONO_2$ group is at the free end of the alkylene chain which is linked by an ether bond to the steroid in position 17. According to said patent it is possible to have nitrate groups also in the positions 3 and 16 of the steroidal structure. The same drawbacks mentioned above as regards the effects on the cardiac frequency can be repeated for the compounds of this patent.

U.S. Pat. No. 3,183,252 describes derivatives of 16-nitrate-alkylpregnanes wherein the alkyl group is linked to the pregnane structure by a carbon-carbon bond. The compounds according to said patent can be used as vasodilators. The same drawbacks reported for the above prior art can be repeated.

WO 98/15568 and WO 03/064443 in the name of the Applicant is describe nitrate esters of steroidal compounds, wherein between the steroidal structure and the nitrooxy group a bivalent linking group is inserted. Said compounds show a good efficacy and/or good tolerability with respect to the corresponding precursors.

Patent application WO 00/61604 in the name of the Applicant describes nitrooxy derivatives of steroidal compounds with various linking groups having at one end a nitrooxy group, and covalently linked with the other end to a steroidal compound. In said application the uses concern the compounds usable in the treatment of patients in oxidative stress. Said compounds contain in the molecule also a bivalent linking group which must be capable to prevent the free radicals production and is selected on the basis of the tests reported therein.

SUMMARY OF THE INVENTION

The Applicant has surprisingly and unexpectedly found a class of nitric oxide releasing compounds with a better bioavailability and/or a prolonged release of NO in comparison with the compounds known in prior art. In general the compounds of the present invention have a better drugability in comparison to the corresponding compounds of the prior art.

DETAILED DESCRIPTION OF THE INVENTION

Object of the present invention are compounds of general formula (I) and pharmaceutically acceptable salts or stereoisomers thereof.

wherein R is a corticosteroid residue of formula (II):

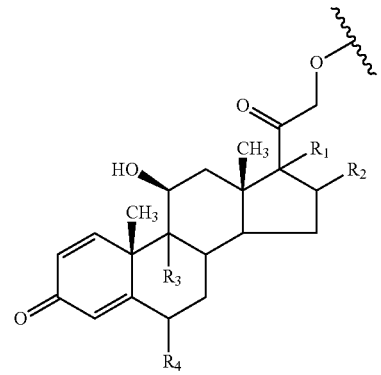

wherein:
$R_1$ is OH, $R_2$—$CH_3$, or $R_1$ and $R_2$ are taken together to form a group of formula (III)

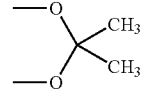

$R_3$ is Cl or F;
$R_4$ is H or F;
wherein $R_1$, $R_2$, $R_3$ and $R_4$ can be linked to the correspondent carbon atoms of the steroidal structure in position α or β; with the proviso that:
when $R_1$ and $R_2$ are the group of formula (III) then $R_3$ is F and $R_9$ is H or F;
when $R_1$ is OH and $R_2$—$CH_3$ then $R_4$ is H and $R_3$ is Cl or F;
preferred corticosteroid radicals are R of formula (II) wherein:
$R_1$ is OH in position α, $R_2$—$CH_3$ in position β, $R_3$ is Cl in position α and $R_4$ is H; or $R_1$ is OH in position α, $R_2$—$CH_3$ in position $R_3$ is F in position α and $R_4$ is H; or
$R_1$ and $R_2$ are taken together to form a group of formula (III)

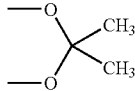
(III)

$R_3$ is F and $R_4$ is H, $R_1$, $R_2$ and $R_3$ are in position α; or
$R_1$ and $R_2$ are taken together to form a group of formula (III)

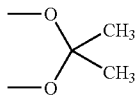
(III)

$R_3$ and $R_4$ are F, $R_1$, $R_2$, $R_3$ and $R_4$ are in position α;
a in formula (I) is equal to 0 or 1;
Z is a group capable of binding $R_x$ and is selected from —C(O)—, or —CH(R')—O— wherein R' is selected from H or a straight or branched $C_1$-$C_4$ alkyl, preferably R' is H or —$CH_3$;
$R_x$ is a radical and is selected from the following meanings:
A)
   (a1) —HN—CH($R^1$)—C(O)-(T-Y—$ONO_2$)
   (a2) —C(O)—CH($R^1$)—NH-(T'-Y—$ONO_2$)
   (a3) —HN—CH($R^{1a}$-T"-Y—$ONO_2$)—$COOR^{3a}$
   (a4) —C(O)—OH($R^{1a}$-T"-Y'—$ONO_2$)
   (a5) —$R^{1b}$—CH(NH$R^{4a}$)—C(O)-(T-Y—$ONO_2$)
   (a6) —$R^{1b}$—CH(COO$R^{3a}$)NH-(T'-Y—$ONO_2$)
   (a7) —HN—CH($R^{1a}$-T"-Y'—$ONO_2$)—C(O)-(T-Y—$ONO_2$)
   (a8) —C(O)—CH($R^{1a}$-T"-Y'—$ONO_2$)—NH-(T'-Y—$ONO_2$)
   (a9) —$R^{1b}$—CH(NH-T'-Y'—$ONO_2$)—C(O)-(T-Y—$ONO_2$)
   (a10) —$R^{1b}$—CH(C(O)-T-Y—$ONO_2$)—NH-(T'-Y—$ONO_2$)
wherein:
$R^1$ is selected from:
   A1) H, —$CH_3$, isopropyl, isobutyl, sec-butyl, tert-butyl, methylthio-$(CH_2)_2$—, phenyl, benzyl, $C_6H_5$—$CH_2$—$CH_2$—, 2-monosubstituted benzyl, or 3-monosubstituted benzyl or 4-monosubstituted benzyl wherein the substituent of the benzyl is selected from —F, —Cl, I, —$NO_2$, —$CF_3$, —$CH_3$, CN, $C_6H_5CO$—;
   2,4-dichlorobenzyl, 3,4-dichlorobenzyl, 3,4-difluorobenzyl, 2-pyrrolidyl, 3-triptophanyl-$CH_2$—, 3-benzothienyl-$CH_2$—, 4-imidazolyl-$CH_2$—, 9-anthranyl-$CH_2$—, cyclohexyl, cyclohexyl-$CH_2$-cyclohexyl-$(CH_2)_2$—, cyclopentyl-$CH_2$—, $(C_6H_5)_2CH$—, 4-B(OH)$_2$— benzyl, 4-quinolyl-$CH_2$—, 3-quinolyl-$CH_2$—, 2-quinolyl-$CH_2$—, 2-quinoxalyl-$CH_2$—, 2-furyl-$CH_2$—, 1-naphtyl-$CH_2$—, 2-naphtyl-$CH_2$—, 2-pyridyl-$CH_2$—, 3-pyridyl-$CH_2$—, 4-pyridyl-$CH_2$—, 2-thienyl-$CH_2$—, 3-thienyl-$CH_2$—, $C_6H_4$—CH═CH—$CH_2$—, $CH_2$═CH—$CH_2$—, CH≡CH—$CH_2$—, $NH_2$—CO—$CH_2$—, $NH_2CH$—CO—$(CH_2)_2$—, $NH_2$(═NH)NH—$(CH_2)_3$—, P(═O)(OCH$_3$)$_2$, I—$CH_2$—, preferably $R^1$ is H, —$CH_3$, isopropyl, benzyl;
   A2) —$CH_2$—SH, —$CH_2$—OH, —CH($CH_3$)—OH, —$CH_2$—[($C_6H_4$)-(4-OH)], —$CH_2$—[($C_6H_2$)-(3,5-diiodo)-(4-OH)], —$CH_2$—[($C_6H_3$)-(3-nitro)-(4-CH)], preferably $R^1$ is —$CH_2$—OH or —$CH_2$—[($C_6H_4$)-(4-OH)];
   A3) —$CH_2$—NHR", —$(CH_2)_2$—NHR", —$(CH_2)_3$—NHR", —$(CH_2)_4$—NHR", wherein R" is H, —C(O)$CH_3$ or

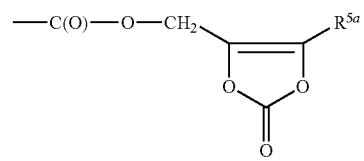

wherein $R^{3a}$ is H or a linear or branched $C_1$-$C_{10}$ alkyl chain, preferably $R^{5a}$ is H or a linear ($C_1$-$C_5$) alkyl, preferably $R^1$ is —$(CH_2)_4$—NHR", wherein R" is as above defined;
   A4) —$CH_2$—C(O)R"—$(CH_2)_2$—C(O)R"—$(CH_2)_4$—C(O)R" wherein R" is —OR$^{5a}$ or

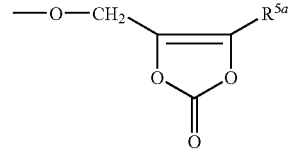

wherein $R^{5a}$ is as above defined, preferably $R^1$ is —$CH_2$—C(O)R'", wherein R" is as above defined;
$R^{1a}$ is selected from,
   A5) —$CH_2$—S—, —$CH_2$—O—, —CH($CH_3$)—O—, —$CH_2$[($C_6H_4$)—(4-O)—], —$CH_2$-[(3,5-diiodo)-($C_6H_2$)—(4-O)—], —$CH_2$-[(3-nitro)-($C_6H_3$)—(4-O)—], preferably $R^{1a}$ is —$CH_2$—O—;
   A6) —$CH_2$—NH—, —$(CH_2)_2$—NH—, —$(CH_2)_3$—NH—, —$(CH_2)_4$—NH—, preferably $R^{1a}$ is —$(CH_2)_4$—NH— or —$CH_2$—NH—;
   A7) —$CH_2$—C(O)—$(CH_2)_2$—C(O)—$(CH_2)_4$—C(O)—, preferably $R^{1a}$ is —$CH_2$—C(O)—;
$R^{3a}$ is selected from H, —$R^{5a}$ or

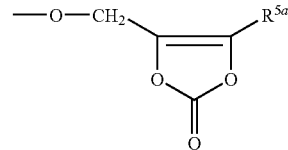

wherein $R^{5a}$ is as above defined;
$R^{4a}$ is selected from H or —C(O)$CH_3$ or

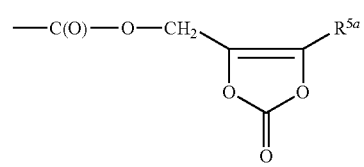

wherein $R^{5a}$ is as above defined;
$R^{1b}$ is selected from
   A8) —S—$CH_2$—, —O—CH($CH_3$)—, —O—$CH_2$—, [-(4-O)—($C_6H_4$)]—$CH_2$—, [—(4-O)-(3,5-diiodo)-

$(C_6H_2)]$—$CH_2$—, [—(4-O)-(3-nitro)-$(C_6H_3)$]—$CH_2$—, preferably $R^{1b}$ is —O—$CH_2$— or [—(4-O)—$(C_6H_4)$]—$CH_2$—;

A9) —HN—$CH_2$—, —HN—$(CH_2)_2$—, —HN—$(CH_2)_3$—, —HN—$(CH_2)_4$—, preferably $R^{1b}$ is —HN—$(CH_2)_4$— or —HN—$CH_2$—;

A10) —C(O)—$CH_2$—, —C(O)—$(CH_2)_2$—, —C(O)—$(CH_2)_4$—, preferably $R^{1b}$ is —C(O)—$CH_2$—;

T is selected from —O—, —S—, —NR'—, —O—CH(R')—O—C(O)— or —O—CH(R')—O—C(O)O— wherein R' is as above defined;

T' is —C(O)—C(O)—X"— wherein X" is —O— or —S—, or T' is —C(O)—NR'— wherein R' is as above defined;

T" is independently selected from —O(O)—, —C(O)—X"—, —C(O)—NR'—O—, —S—, —NR'—O—CH(R')—O—O(O)—, —O—CH(R')—O—C(O)O—, wherein X" and R' are as above defined, with the proviso that T" is —O(O)—, —O(O)—X"— or —C(O)—NR'— when T" is linked to —NH—, —O—, or —S—; or T" is —O—, —S—, —NR'—O—CH(R')—O—O(O)—, —O—CH(R')—O—O(O)O— when T" is linked to —O(O)—;

Y and Y' are as below defined;

B)
(b1) —HN—CH($R^2$)—$CH_2C(O)$-(T-Y—$ONO_2$)
(b2) —O(O)—$CH_2$—CH($R^2$)—NH-(T'-Y—$ONO_2$)
(b3) —HN—CH($R^{2a}$-T"-Y'—$NO_2$)—$CH_2COOR^{3a}$
(b4) —C(O)—$CH_2$—CH($R^{1a}$-T"-Y'—$ONO_2$)—$NHR^{4a}$
(b5) —$R^{2b}$—CH($NHR^{4a}$)—$CH_2C(O)$-(T-Y—$ONO_2$)
(b6) —$R^{2b}$—CH($CH_2COOR^{3a}$)NH-(T-Y—$ONO_2$)
(b7) —HN—CH($R^{2a}$-T"-Y'—$ONO_2$)—$CH_2$—C(O)-(T-Y—$ONO_2$)
(b8) —C(O)—$CH_2$—CH($R^{2a}$-T"-Y—$ONO_2$)—NH-(T-Y—$ONO_2$)
(b9) —$R^{2b}$—CH(NH-T'-Y'—$ONO_2$)—$CH_2O(O)$-(T'-Y—$ONO_2$)
(b10) —$R^{2b}$—CH($CH_2C(O)$-T-Y'—$ONO_2$)—NH-(T'-Y'—$ONO_2$)

wherein
$R^2$ is selected from
B1) H, —$CH_3$, $CF_3$, isopropyl, isobutyl, sec-butyl, methylthio-$(CH_2)_2$—, phenyl, benzyl, 3-triptophanyl-$CH_2$—, $NH_2$—C(O)—$CH_2$—, $NH_2$—C(O)—$(CH_2)_2$—, $NH_2$(=NH)NH—$(CH_2)_3$—, tBuO—CH($CH_3$)—, benzyl-O—$CH_2$—, 4-terbutoxy-benzyl, 4-phenylbenzyl, preferably $R^2$ is H, —$CH_3$, isopropyl, benzyl;

B2) —$CH_2$—SH, —$CH_2$—OH, —CH($CH_3$)—OH, —$CH_2$—$[(C_6H_4)$-(4-OH)]$, —$CH_2$—$[(C_6H_3)$-(3,5-diiodo)-(4-OH)]$, —$(CH_2)$—$[(C_6H_3)$—(3-nitro)-(4-OH)]$;

B3) —$CH_2$—NHR'", —$(CH_2)_2$—NHR'"—$(CH_2)_3$—NHR'", —$(CH_2)_4$—NHR'", wherein R'" is as above defined, preferably $R^2$ is —$(CH_2)_4$—NHR'";

B4) —$CH_2$—C(O)—R'", —$(CH_2)_2$—C(O)—R'", —$(CH_2)_4$—C(O)—R'" wherein R'" is as above defined, preferably $R^2$ is —$CH_2$—C(O)—R'";

$R^{2a}$ is selected from
B5) —$CH_2$—S—, —$CH_2$—O—, —CH($CH_3$)—O— or —$CH_2[(C_6H_4)$—(4-O)—], —$CH_2$-[(3,5-diiodo)-$(C_6H_2)$—(4-O)—], —$CH_2$-[(3-nitro)-$(C_6H_3)$—(4-O)—], preferably $R^{2a}$ is —$CH_2$—O—;

B6) —$CH_2$—NH—, —$(CH_2)_2$—NH—, —$(CH_2)_3$—NH—, —$(CH_2)_4$—NH—, preferably $R^{2a}$ is —$(CH_2)_4$—NH— or —$CH_2$NH—;

B7) —$CH_2$—C(O)—, —$(CH_2)_2$—O(O)—, —$(CH_2)_4$—O(O)—, preferably $R^{2a}$ is —$CH_2$—C(O)—;

$R^{2b}$ is selected from
B8) —S—$CH_2$—, —O—CH($CH_3$)—, —O—$CH_2$—, [-(4-O)—$(C_6H_4)$]—$CH_2$—, [-(4-O)-(3,5-diiodo)$(C_6H_2)$]—$CH_2$—, [-(4-O)-(3-nitro)-$(C_6H_3)$]—$CH_2$—, preferably $R^{2b}$ is —O—$CH_2$— or [-(4-O)—$(C_6H_4)$]—$CH_2$—;

B9) —HN—$CH_2$—, —HN—$(CH_2)_2$—, —HN—$(CH_2)_3$—, —HN—$(CH_2)_4$—, preferably $R^{2b}$ is —HN—$(CH_2)_4$— or —HN—$CH_2$—;

B10) —C(O)—$CH_2$—, —C(O)—$(CH_2)_2$—, —C(O)—$(CH_2)_4$—, preferably $R^{2b}$ is —C(O)—$CH_2$—;

$R^{3a}$ and $R^{4a}$ are as above defined;
T, T' and T" are as above defined and Y and Y' are as below defined;

C)
(c1) —HN—$(CH_2)_b$—C(O)-(T-Y—$ONO_2$)
(c2) —C(O)—$(CH_2)_b$—NH-(T'-Y—$ONO_2$);

wherein b is an integer from 3 to 6,
T and T' are as above defined and Y and Y' are as below defined;

D)
(d1) —HN—CH($R^{12}$)—$CH_2$—O-(T'"-Y—$ONO_2$)
(d2) —O—$CH_2$—CH($R^{12}$)—NH-(T'-Y—$ONO_2$)
(d3) —HN—CH($R^{12a}$-T"-Y'—$ONO_2$)—$CH_2OH$
(d4) —O—$CH_2$—CH($R^{12a}$-T"-Y'—$ONO_2$)—$NHR^{4a}$
(d5) —$R^{12b}$—CH($NHR^{4a}$)—$CH_2$—O-(T'"-Y—$ONO_2$)
(d6) —$R^{12b}$—CH($CH_2OH$)—NH-(T'"-Y—$ONO_2$)
(d7) —HN—CH($R^{12a}$-T"-Y'—$ONO_2$)—$CH_2$—O-(T'"-Y—$ONO_2$)
(d8) —O—$CH_2$—CH($R^{12a}$-T"-Y'—$ONO_2$)—NH-(T'-Y—$ONO_2$)
(d9) —$R^{12b}$—CH(NH-T'-Y'—$ONO_2$)—$CH_2$—O-(T'"-Y—$ONO_2$)
(d10) —$R^{12b}$—CH($CH_2$—O-T'"-Y'—$ONO_2$)—NH-(T'-Y—$ONO_2$)

wherein
T'" is independently selected from —C(O)—, —C(O)X"— wherein X" is —O— or —S—, or —C(O)—NR'— wherein R' is as above defined;
T' and T" are as above defined;
Y and Y' are as below defined;
$R^{12}$ is selected from:
D1) H, —$CH_3$, isopropyl, isobutyl, sec-butyl, methylthio-$(CH_2)_2$—, benzyl, 3-triptophanyl-$CH_2$—, 4-imidazolyl-$CH_2$—, $NH_2$—CO—$CH_2$—, $NH_2$—CO—$(CH_2)_2$—, $NH_2$(=NH)NH—$(CH_2)_3$—, preferably $R^{12}$ is H;

D2) —$CH_2$—OH, —CH($CH_3$)—OH, —$CH_2$—$[(C_6H_4)$-(4-OH)]$, —$CH_2$—$[(C_6H_3)$-(3,5-diiodo)-(4-OH)]$, —$CH_2$—$[(C_6H_3)$-(3-nitro)-(4-OH)]$, preferably $R^{12}$ is —$CH_2$—OH or —$CH_2$—$[(C_6H_4)$—(4-OH)]$;

D3) —$CH_2$—NHR'", —$(CH_2)_2$—NHR'", —$(CH_2)_3$—NHR'", —$(CH_2)_4$—NHR'", wherein R'" is as above defined, preferably $R^{12}$ is —$(CH_2)_4$—NHR'";

D4) —$CH_2$—C(O)R'", —$(CH_2)_2$—C(O)R'", —$(CH_2)_4$—C(O)R'" wherein R'" is as above defined, preferably $R^{12}$ is —$CH_2$—C(O)R'";

$R^{12a}$ is selected from
D5) —$CH_2$—O—, —CH($CH_3$)—O— or —$CH_2$—$[(C_6H_4)$-(4-O)—], —$CH_2$-[3,5-diiodo-$(C_6H_2)$—(4-O)—], —$CH_2$-[3-nitro-$(C_6H_3)$-4-O—], preferably $R^{12a}$ is $CH_2$—O— or —$CH_2[(C_6H_4)$—(4-O)—];

D6) —$CH_2$—NH—, —$(CH_2)_2$—NH—, —$(CH_2)_3$—NH—, —$(CH_2)_4$—NH—, preferably $R^{12a}$ is —$(CH_2)_4$—NH— or —$CH_2$—NH—;

D7) —$CH_2$—C(O)—$(CH_2)_2$—C(O) $(CH_2)_4$—C(O)—, preferably $R^{12a}$ is —$CH_2$—C(O)—;

$R^{12b}$ is selected from

D8) —O—CH$_2$—, —O—CH(CH$_3$)—, [—(4-O)-(C$_6$H$_4$)]—CH$_2$, [—(4-O)-(3,5-diiodo)-(C$_6$H$_2$)]—CH$_2$, [-(4-O)-(3-nitro)-(C$_6$H$_3$)]—CH$_2$—, preferably $R^{12b}$ is —O—CH$_2$— or [-(4-O)-(C$_6$H$_4$)]—CH$_2$—;

D9) —HN—CH$_2$—, —HN—(CH$_2$)$_2$—, —HN—(CH$_2$)$_3$—, —HN—(CH$_2$)$_4$—, preferably $R^{12b}$ is —HN—(CH$_2$)$_4$— or —HN—CH$_2$—;

D10) —C(O)—CH$_2$—, —C(O)—(CH$_2$)$_2$—, is —C(O)—CH$_2$—;

$R^{4a}$ is as above defined;

E)

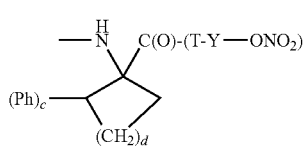 (e1)

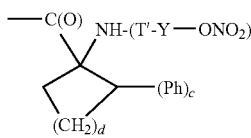 (e2)

wherein c is equal to 0 or 1, d is an integer from 0 to 3 with the proviso that c is 0 or 1 when d is 0 and c is 0 when d is 1, 2 or 3, T and T' are as above defined and Y is as below defined;

F)

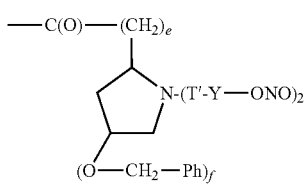 (XI) (f1)

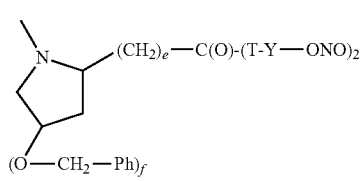 (f2)

wherein e and f are equal to 0 or 1, with the proviso that f is 0 when e is 0 and f is 0 or 1 when e is 1, T and T' are as above defined and Y is as below reported;

G)

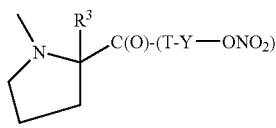 (g1)

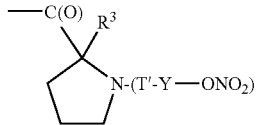 (g2)

wherein $R^3$ is H, CH$_3$, propyl, (C$_6$H$_5$)$_2$CH—, 1-naphtyl-CH$_2$—, benzyl, allyl, 2-bromobenzyl, 2-chlorobenzyl, 3-chlorobenzyl, fluorobenzyl, 4-bromobenzyl, 4-methylbenzyl, preferably $R^3$ is H, T and T' are as above defined and Y is as below defined;

H)

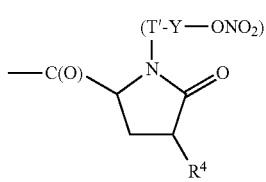 (h1)

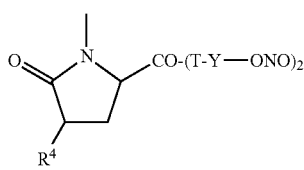 (h2)

wherein $R^4$ is H, benzyl, 4-bromobenzyl, 2-bromobenzyl, T and T' are as above defined and Y is as below defined;

I)

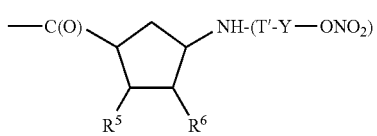 (i1)

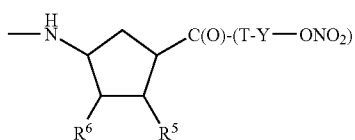 (i2)

wherein $R^5$ is H, $R^6$ is H, or $R^5$ and $R^6$ when taken together are a double bond, T and T' are as above defined and Y is as below reported;

L)

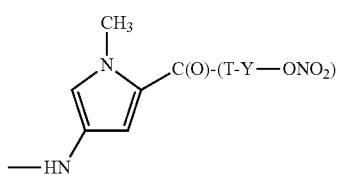 (l1)

-continued

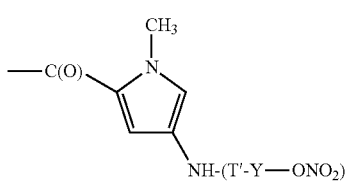
(l2)

wherein T and T' are as above defined and Y is as below reported;

M)

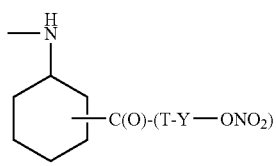
(m1)

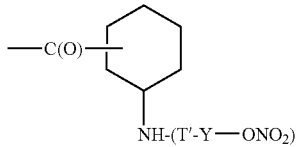
(m2)

wherein T and T' are as above defined and Y is as below reported;

N)

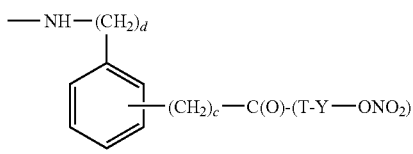
(n1)

(n2)

wherein c is as above defined, d is equal to 0 or 1, T and T' are as above defined and Y is as below reported;

O)

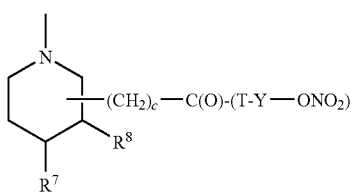
(o1)

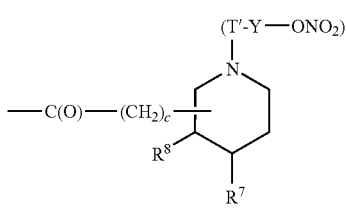
(o2)

wherein $R^7$ is H, $R^8$ is H, or $R^7$ and $R^8$ when taken together are a double bond, c is as above defined, T and T' are as above defined and Y is as below reported;

P)

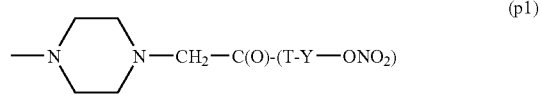
(p1)

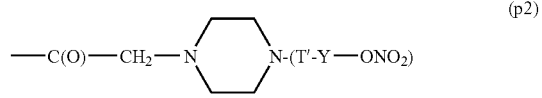
(p2)

wherein T and T' are as above defined and Y is as below reported;

Q)

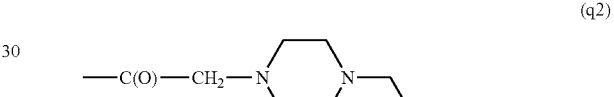
(q1)

(q2)

wherein T and T' are as above defined and Y is as below reported;

R)

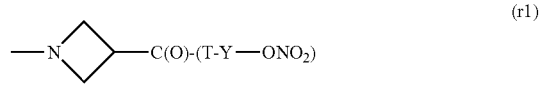
(r1)

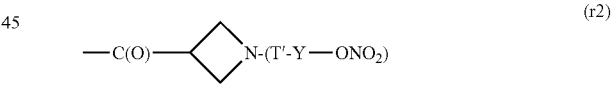
(r2)

wherein T and T' are as above defined and Y is as below reported;

S)

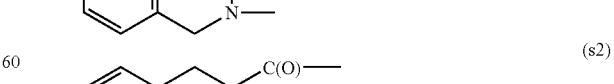
(s1)

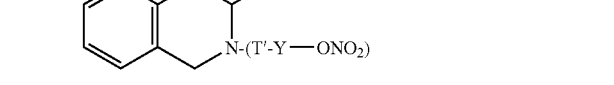
(s2)

wherein T and T' are as above defined and Y is as below reported;

T)

(t1) [structure: tetrahydro-β-carboline with C(O)-(T-Y—ONO$_2$) and N-CH$_3$]

(t2) [structure: tetrahydro-β-carboline with C(O)— and N-(T'-Y—ONO$_2$)]

wherein T and T' are as above defined and Y is as below reported;

U)

(u1) [structure: —N(R$^{11}$)—C(R$^{10}$)(R$^9$)—C(O)-(T-Y—ONO$_2$)]

(u2) [structure: —C(O)—C(R$^9$)(R$^{10}$)—N(R$^{11}$)-(T'-Y—ONO$_2$)]

wherein R$^9$ and R$^{10}$ are H, CH$_3$, R$^{11}$ is CH$_3$ or 4-piperidinyl with the proviso that R$^9$ and R$^{10}$ are H when R$^{11}$ is 4-piperidinyl and R$^9$ and R$^{10}$ are CH$_3$ when R$^{11}$ is CH$_3$, T and T' are as above defined and Y is as below reported;

V)

(v1) [structure: pyrrolidinone with C(O)-(T-Y—ONO$_2$) and CH(CH$_3$)$_2$ substituents, and —NH]

(v2) [structure: pyrrolidinone with C(O) and CH(CH$_3$)$_2$, —NH-(T'-Y—ONO$_2$)]

wherein T and T' are as above defined and Y is as below reported;

with the proviso that in the formula (I):
a is 0 or a is 1 and Z is —CH(R')—O— wherein R' is as above defined, when R$_x$ is:
(a2), (a4) or (a8);
(a5), (a6), (a9) or (a10) and R$^{1b}$ is selected from the group A10);
(b2), (b4) or (b8);
(b5), (b6), (b9) or (b10) and R$^{2b}$ is selected from the group B10);
(c2);
(d5), (d6), (d9) or (d10) and R$^{12b}$ is selected from the group D10);
(e2), (f1), (g2), (h1), (i1), (l2), (m2), (n2), (o2), (p2), (q2), (r2), (s2), (t1) or (u2);
a is 1 and Z is —C(O)—, when R$_x$ is:
(a1), (a3) or (a7);
(a5), (a6), (a9) or (a10) and R$^{1b}$ is selected from the groups A8) and A9);
(b1), (b3) or (b7);
(b5), (b6), (b9) or (b10) and R$^{2b}$ is selected from the groups B8) or B9);
(c1);
(d1), (d2), (d3), (d4), (d7) or (d8);
(d5), (d6), (d9) or (d10) and R$^{12b}$ is selected from the groups D8) or D9);
(e1), (f2), (g1), (h2), (i2), (l1), (m1), (n1), (o1), (p1), (q1), (r1), (s1), (t2) or (u1).

Y and Y' are bivalent radicals each independently selected from the following meanings:

a)
straight or branched C$_1$-C$_{20}$ alkylene, preferably a straight or branched C$_1$-C$_{10}$ alkylene,
straight or branched C$_1$-C$_{20}$ alkylene substituted with one or more of the substituents selected from the group consisting of: halogen atoms, hydroxy, —ONO$_2$ or T$_2$, wherein T$_2$ is —OC(O)(C$_1$-C$_{10}$ alkyl)-ONO$_2$ or —O(C$_1$-C$_{10}$ alkyl)-ONO$_2$, preferably Y or Y' is a straight or branched C$_1$-C$_{10}$ alkylene substituted with a —ONO$_2$ group;
cycloalkylene with 5 to 7 carbon atoms into cycloalkylene ring, the ring being optionally substituted with one or more straight or branched C$_1$-C$_{10}$ alkyl chains, preferably the ring being optionally substituted with CH$_3$;

b) [structure: —(CH$_2$)$_{n^0}$—phenyl—(U)$_{n^1}$—(CH$_2$)—]

wherein
n$^0$ is an integer from 0 to 20, preferably is 0 or 1;
n$^1$ is 0 or 1, preferably n$^1$ is 1;
U is a linear or branched C$_1$-C$_{20}$ alkylene optionally substituted with a —ONO$_2$ group, preferably U is a linear C$_1$-C$_{10}$ alkylene or U is a linear or branched C$_1$-C$_{10}$ alkylene substituted with a —ONO$_2$ group;

c) [structure: —(CH$_2$)$_{n^0}$—phenyl—(U)$_{n^1}$—(CH$_2$)—COOH]

wherein
n$^0$ is an integer from 0 to 20, preferably n$^0$ is 0 or 1;
n is 0 or 1, preferably n$^1$ is 1;

U is a linear or branched $C_1$-$C_{20}$ alkylene optionally substituted with a —$ONO_2$ group, preferably U is a linear $C_1$-$C_{10}$ alkylene or U is a linear or branched $C_1$-$C_{10}$ alkylene substituted with a —$ONO_2$ group;

d)

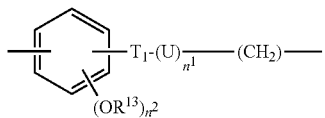

wherein:
$n^2$ is an integer from 0 to 2, $R^{13}$ is H or $CH_3$, $T_1$ is —O—C(O)— or —C(O)O—;
$n^1$ and U are as above defined;

e)

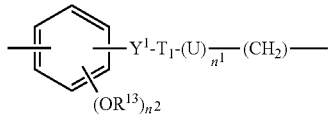

$n^2$ is an integer from 0 to 2, preferably $n^2$ is 1;
$R^{13}$ is H or $CH_3$, preferably $R^{13}$ is $CH_3$;
Y is —$CH_2$—$CH_2$— or —CH=CH—$(CH_2)_{n^{2'}}$—, wherein $n^{2'}$ is 0 or 1, preferably $Y^1$ is —CH=CH—$(CH_2)_{n^{2'}}$— and $n^{2'}$ is 0;
$T_1$=—O—C(O)— or —C(O)O—, preferably $T_1$ is —C(O)O—;
$n^1$ is 0 or 1, preferably $n^1$ is 1;
U is a linear or branched $C_1$-$C_{20}$ alkylene optionally substituted with a —$ONO_2$ group, preferably U is a linear $C_1$-$C_{10}$ alkylene or U is a linear or branched $C_1$-$C_{10}$ alkylene substituted with a —$ONO_2$ group;
more preferably $n^2$ is 1, $R^{13}$ is $CH_3$, $Y^1$ is —CH=CH—$(CH_2)_{n^{2'}}$ and $n^{2'}$ is 0, $T_1$ is —C(O)O— and U is a linear $C_1$-$C_{10}$ alkylene;

e')

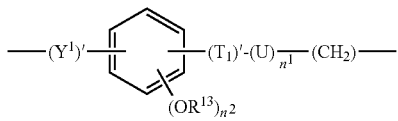

wherein:
$n^2$ is an integer from 0 to 2, preferably $n^2$ is 1;
$R^{13}$ is H or $CH_3$, preferably $R^{13}$ is $CH_3$;
$Y^1$ is —$CH_2$—$CH_2$— or —$(CH_2)_{n^{2'}}$—CH=CH—, wherein n is 0 or 1,
preferably $Y^1$ is —$(CH_2)_{n^{2'}}$—CH=CH— and $n^{2'}$ is 0;
$(T_1)'$=—O—C(O)—;
$n^1$ is 0 or 1, preferably n is 1;
U is a linear or branched $C_1$-$C_{20}$ alkylene optionally substituted with a —$ONO_2$ group, preferably U is a linear $C_1$-$C_{10}$ alkylene or U is a linear or branched $C_1$-$C_{10}$ alkylene substituted with a —$ONO_2$ group;
more preferably $n^2$ is 1, $R^{13}$ is $CH_3$, $Y^1$ is —CH=CH—$(CH_2)_{n^{2'}}$— and $n^{2'}$ is 0, $T_1$ is —OC(O)— and U is a linear $C_1$-$C_{10}$ alkylene; when Y and Y' are selected from b), c), d), e) or e'), the —$ONO_2$ group of -(T-Y—$ONO_2$), -(T'-Y—$ONO_2$), -(T''-Y'—$ONO_2$), -(T'Y'—$ONO_2$), -(T'''-Y—$ONO_2$) and -(T'''-Y'—$ONO_2$) is linked to the —$(CH_2)$— group;

f)

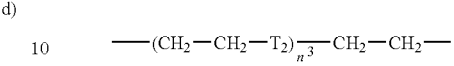

wherein $T_2$ is —O— or —S—, —NH—, preferably $T_2$ is —O—, $n^3$ is an integer from 1 to 6, preferably $n^3$ is 1;

g)

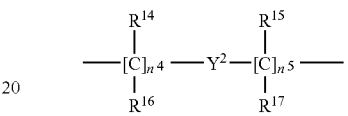

wherein:
$n^4$ is an integer from 0 to 10, preferably n is 0 or 1;
$n^5$ is an integer from 1 to 10, preferably $n^5$ is 1;
$R^{14}$, $R^{15}$, $R^{16}$, $R^{17}$ are the same or different, and are H or straight or branched $C_1$-$C_4$ alkyl, preferably $R^{14}$, $R^{15}$, $R^{16}$ and $R^{17}$ are H;
wherein the —$ONO_2$ group is linked to

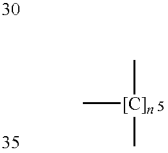

wherein $n^5$ is as defined above;
$Y^2$ is an heterocyclic saturated, unsaturated or aromatic 5 or 6 members ring, containing one or more heteroatoms selected from nitrogen, oxygen, sulphur,
and is selected from the group consisting of:

(Y1)

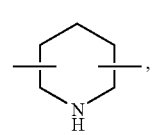

(Y2)

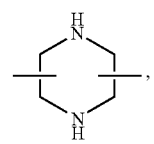

(Y3)

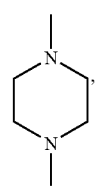

(Y4)

(Y5)

(Y6)

(Y7)

(Y8)

(Y9)

(Y10)

(Y11)

(Y12)

(Y13)

The term "$C_1$-$C_{10}$ alkyl" as used herein refers to branched or straight alkyl groups including methyl, ethyl, n-propyl, isopropyl, n-butyl, isobutyl, t-butyl, pentyl, hexyl, octyl and the like.

The term "cycloalkylene" as used herein refers to ring having from 5 to 7 carbon atoms including, but not limited to, cyclopentylene, cyclohexylene optionally substituted with side chains such as straight or branched ($C_1$-$C_{10}$)-alkyl, preferably $CH_3$.

The term "heterocyclic" as used herein refers to saturated, unsaturated or aromatic 5 or 6 members ring, containing one or more heteroatoms selected from nitrogen, oxygen, sulphur, such as for example pyridine, pyrazine, pyrimidine, pyrrolidine, morpholine, imidazole and the like.

Preferred compounds of formula (I) for the treatment of ocular diseases, in particular ocular hypertension, age-related macular degeneration, diabetic macular edema, diabetic retinopathy, hypertensive retinopathy and retinal vasculopathies, are those wherein the corticosteroid residue R is selected from the group consisting of betamethasone, fluocinolone acetonide, triamcinolone acetonide.

Another embodiment of the invention relates to compounds of formula (I) wherein in the corticosteroid R of formula (II) $R_1$, $R_2$, $R_3$ and $R_4$ have the following meanings:
$R_1$ is OH in position α, $R_2$ —$CH_3$ in position β, $R_3$ is Cl in position α and $R_4$ is H; or
$R_1$ is OH in position α, $R_2$ —$CH_3$ in position β, $R_3$ is F in position α and $R_4$ is H; or
$R_1$ and $R_2$ are taken together to form a group of formula (III)

$$(III)$$

$R_3$ is F and $R_4$ is H, $R_1$, $R_2$ and $R_3$ are in position α; or
$R_1$ and $R_2$ are taken together to form a group of formula (III)

$$(III)$$

$R_3$ and $R_4$ are F, $R_1$, $R_2$, $R_3$ and $R_4$ are in position α;
in formula (I)
a is 0 and
$R_x$ is selected from:
(a2) —C(O)—CH($R^1$)—NH-(T'-Y—$ONO_2$)
wherein
$R^1$ of the group A1) is selected from H, isobutyl, benzyl, $C_6H_5$—$CH_2$—$CH_2$—, 2-monosubstituted benzyl, or 3-monosubstituted benzyl or 4-monosubstituted benzyl wherein the substituent of the benzyl is selected from —F, —Cl, I, —$NO_2$, —$CF_3$, —$CH_3$, CN, $C_6H_5$CO—;
$R^1$ of the group A2) is selected from —$CH_2$—OH, —CH($CH_3$)OH— or —$CH_2$[($C_6H_4$)—(4-OH)], or
$R^1$ of the group A3) is selected from —$CH_2$—NHR", —($CH_2$)$_2$—NHR", —($CH_2$)$_3$—NHR", —($CH_2$)$_4$—NHR", wherein R" is H, or —C(O)$CH_3$;
$R^1$ of the group A4) is selected from —$CH_2$—C(O)R", ($CH_2$)$_2$— C(O)R", —($CH_2$)$_4$—C(O)R'" wherein R" is $OR^{5a}$ wherein $R^{5a}$ is H or a linear ($C_1$-$C_5$) alkyl;
T' is —C(O)— C(O)—X" wherein X" is —S— or —O—, preferably T' is —C(O)—;
Y is as below defined;
or $R_x$ is
(a4) —C(O)—CH($R^{1a}$-T"-Y'—$ONO_2$)—$NHR^{4a}$
wherein $R^{1a}$ of the group A5) is selected from —$CH_2$—O—, —CH($CH_3$) O— or —$CH_2$[($C_6H_4$)-(4-O)—], or
$R^{1a}$ of the group A6) is selected from —$CH_2$—NH—, —($CH_2$)$_2$—NH—, ($CH_2$)$_3$—NH—, —($CH_2$)$_4$—NH—, or
$R^{1a}$ of the group A7) is selected from —$CH_2$—C(O)— ($CH_2$)$_2$—C(O)—, —($CH_2$)$_4$—C(O)—;
$R^{4a}$ is H or —O(O)$CH_3$;
T" is —C(O)— or —C(O)—X" wherein X" is —S— or —O—, when $R^{1a}$ is selected from the group A5) or A6), preferably T" is —C(O)—;
T" is —O—, —S—, —NR'— or —O—CH(R')—O—C(O)— wherein R' is H or —$CH_3$, when $R^{1a}$ is selected from the group A7);
Y' is as below defined;
or $R_x$ is selected from
(a5) —$R^{1b}$—CH($NHR^{4a}$)—C(O)-(T-Y—$ONO_2$)
(a6) —$R^{1b}$—CH($COOR^{3a}$)—NH-(T'Y—$ONO_2$)

(a9) —$R^{1b}$—CH(NH-T'Y'—$ONO_2$)—C(O)-(T-Y—$ONO_2$) or (a10) —$R^{1b}$—CH(C(O)-T-Y'—$ONO_2$)—NH-(T'Y—$ONO_2$)
wherein
$R^{1b}$ of the group A10) is selected from —C(O)—$CH_2$—, —C(O)—$(CH_2)_2$—, —C(O)—$(CH_2)_4$—;
$R^{3a}$ is H or a ($C_1$-$C_5$) alkyl;
$R^{4a}$ is H or —O(O)$CH_3$;
T is —O—, —S—, —NR' or —O—CH(R')—O—C(O)— wherein R' is H or —$CH_3$, preferably T is —O—;
T' is —C(O)— or —O(O)—X" wherein X" is —S— or —O—, preferably T' is —C(O)—;
Y and Y' are as below defined; or $R_x$ is (a8) —C(O)—CH($R^{1a}$-T"-Y'—$ONO_2$)—NH-(T'-Y—$ONO_2$)
wherein
$R^{1a}$ of the group A5) is selected from —$CH_2$—O—, —CH($CH_3$)—O— or —$CH_2$—[($C_6H_4$)-(4-O—)—], or
$R^{1a}$ of the group A6) is selected from —$CH_2$—NH—, —$(CH_2)_2$—NH—, —$(CH_2)_3$—NH—, —$(CH_2)_4$—NH—, or
$R^{1a}$ of the group A7) is selected from —$CH_2$—C(O)—, —$(CH_2)_2$—C(O)—, —$(CH_2)_4$—C(O)—;
T" is —C(O)— or —O(O)—X" wherein X" is —S— or —O—, when $R^{1a}$ is selected from the group A5) or A6), preferably T" is —O(O)—;
T" is —O—, —S—, —NR'— or —O—CH(R')—O—C(O)— wherein R' is H or —$CH_3$, when $R^{1a}$ is selected from the group A7);
T' is —C(O)— or —C(O)—X" wherein X" is —S— or —O—, preferably T' is —C(O)—;
Y and Y' are as below defined;
or $R_x$ is (b2) —C(O)—$CH_2$—CH($R^2$)—NH-(T'-Y—$ONO_2$)
wherein
$R^2$ of the group B1) is selected from H, $CH_3$, isobutyl, isopropyl, benzyl;
T' is —C(O)—, —C(O)—X" wherein X" is —S— or —O—, preferably T' is —O(O)—;
Y and Y' are each independently selected from a)
a straight or branched $C_1$-$C_{10}$ alkylene,
a straight or branched $C_1$-$C_{10}$ alkylene substituted with a —$ONO_2$ group;

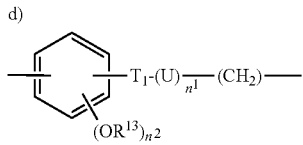

wherein:
$n^2$ is an integer from 0 to 2, $R^{13}$ is H or $CH_3$, $T_1$ is —O—C(O)— or —C(O)O—;
$n^1$ is 1 and U is a linear $C_1$-$C_{10}$ alkylene or U is a linear or branched $C_1$-$C_{10}$ alkylene substituted with a —$ONO_2$ group;

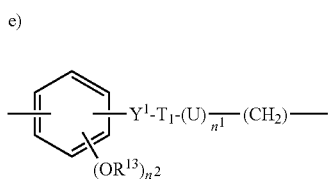

$n^2$ is 1, $R^{13}$ is $CH_3$, $Y^1$ is —CH=CH—$(CH_2)_{n^{2'}}$— and $n^{2'}$ is 0, $T_1$ is —C(O)O— and U is a linear $C_1$-$C_{10}$ alkylene;

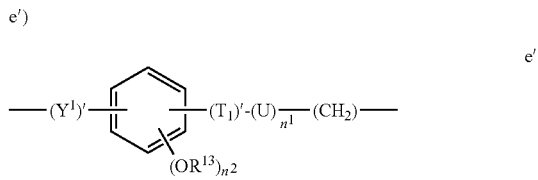

wherein:
$n^2$ is 1, $R^{13}$ is $CH_3$;
$Y^1$ is —$(CH_2)_{n^{2'}}$—CH=CH— and $n^{2'}$ is 0;
$(T_1)'$=—O—C(O)—;
$n^1$ is 1 and U is a linear $C_1$-$C_{10}$ alkylene or U is a linear or branched $C_1$-$C_{10}$ alkylene substituted with a —$ONO_2$ group;
when Y and Y' are selected from d), e) or e'), the —$ONO_2$ group of -(T-Y—$ONO_2$), -(T'-Y—$ONO_2$), (T"-Y'—$ONO_2$) (T'-Y'—$ONO_2$), -(T"-Y—$ONO_2$) and -(T"-Y'—$ONO_2$) is linked to the —$(CH_2)$— group;

wherein $T_2$ is —O— or —S—, —NH—, preferably $T_2$ is —O—, $n^3$ is 1 or 2;

Another embodiment of the invention relates to compounds of formula (I) wherein in the corticosteroid R of formula (II) $R_1$, $R_2$, $R_3$ and $R_4$ have the following meanings:
$R_1$ is OH in position α, $R_2$—$CH_3$ in position β, $R_3$ is Cl in position α and $R_4$ is H; or
$R_1$ is OH in position α, $R_2$—$CH_3$ in position β, $R_3$ is F in position α and $R_4$ is H; or
$R_1$ and $R_2$ are taken together to form a group of formula (III)

$R_3$ is F and $R_4$ is H, $R_1$, $R_2$ and $R_3$ are in position α; or
$R_1$ and $R_2$ are taken together to form a group of formula (III)

$R_3$ and $R_4$ are F, $R_1$, $R_2$, $R_3$ and $R_4$ are in position α;
in formula (I)
a is 1 and Z is —C(O)—;
$R_x$ is
(a1) —HN—CH($R^1$)—C(O)-(T-Y—$ONO_2$)
wherein
$R^1$ of the group A1) is selected from H, isobutyl, benzyl, $C_6H_5$—$CH_2$—$CH_2$—, 2-monosubstituted benzyl, or 3-monosubstituted benzyl or 4-monosubstituted benzyl wherein the substituent of the benzyl is selected from —F, —Cl, I, —NO$_2$, —CF$_3$, —CH$_3$, CN, C$_6$H$_5$CO—;
or
R$^1$ of A2) is selected from —CH$_2$—OH, —CH(CH$_3$)—OH— or —CH$_2$[(C$_6$H$_4$)— (4-OH)], or
R$^1$ of the group A3) is selected from —CH$_2$—NHR", —(CH$_2$)$_2$—NHR", —(CH$_2$)$_3$—NHR", —(CH$_2$)$_4$—NHR", wherein R" is H, or —C(O)CH$_3$,
R$^1$ of the group A4) is —CH$_2$—C(O)R''', —(CH$_2$)$_2$—C(O)R''', —(CH$_2$)$_4$—C(O)R''' wherein R''' is OR$^{5a}$ wherein R$^{5a}$ is H or a linear (C$_1$-C$_5$) alkyl;
T is —O—, —S—, —NR'-O—CH(R')—O—C(O)— wherein R' is H or a straight or branched C$_1$-C$_4$ alkyl, preferably T is —O—;
Y is as below defined;
or R$_x$ is
(a3) —HN—CH(R$^{1a}$-T"-Y'—ONO$_2$)—COOR$^{3a}$ wherein
R$^{1a}$ of the group A5) is selected from —CH$_2$—O—, —CH(CH$_3$) O— or —CH$_2$[(C$_6$H$_4$)O$_p$—], or
R$^{1a}$ of the group A6) is selected from —CH$_2$—NH—, —(CH$_2$)$_2$—NH—, (CH$_2$)$_3$—NH—, —(CH$_2$)$_4$—NH—, or
R$^{1a}$ of the group A7) is —CH$_2$—C(O)—(CH$_2$)$_2$—C(O)—(CH$_2$)$_4$—C(O)—;
R$^{3a}$ is H or a (C$_1$-C$_5$) alkyl;
T" is —C(O)— or —C(O)—X" wherein X" is —S— or —O—, when R$^{1a}$ is selected from the group A5) or A6), preferably T" is —O(O)—;
T" is —O—, —S—, —NR'-O—CH(R')—O—C(O)— wherein R' is H or a straight or branched C$_1$-C$_4$ alkyl, when R$^{1a}$ is selected from the group A7);
Y' is as below defined;
or R$_x$ is
(a5) —R$^{1b}$—CH(NHR$^{4a}$)—C(O)-(T-Y—ONO$_2$)
(a6) —R$^{1b}$—CH(COOR$^{3a}$)NH-(T'-Y—ONO$_2$)
(a9) —R$^{1b}$—CH(NH-T'-Y'—ONO$_2$)—C(O)-(T-Y—ONO$_2$)
or
(a10) —R$^{1b}$—CH(C(O)-T-Y'—ONO$_2$)—NH-(T'-Y—ONO$_2$)
wherein
R$^{1b}$ of the group A8) is selected from —O—CH(CH$_3$)—, —O—CH$_2$—, [-4-O)—(C$_6$H$_4$)]—CH$_2$—, or
R$^{1b}$ of the group A9) is selected from —HN—CH$_2$—, —HN—(CH$_2$)$_2$—, —HN—(CH$_2$)$_3$—, —HN—(CH$_2$)$_4$—;
R$^{3a}$ is H or a (C$_1$-C$_5$) alkyl;
R$^{4a}$ is H or —C(O)CH$_3$;
T is —O—, —S—, —NR'—, —O—CH(R')—O—C(O)— wherein R' is H or a straight or branched C$_1$-C$_4$ alkyl, preferably T is —O—;
T' is —C(O)— or —C(O)—X" wherein X" is —S— or —O—, preferably T' is —C(O)—;
Y and Y' are as below defined;
or R$_x$ is
(a7) —HN—CH—ONO$_2$)—O(O)-(T-Y—ONO$_2$)
wherein
R$^{1a}$ of the group A5) is selected from —OH$_2$—O—, —CH(CH$_3$)—O— or —CH$_2$—[(C$_6$H$_4$)-(4-O)—], or
R$^{1a}$ of the group A6) is selected from —CH$_2$—NH—, —(CH$_2$)$_2$—NH—, —(CH$_2$)$_3$—NH—, —(CH$_2$)$_4$—NH—, or
R$^{1a}$ of the group A7) is —CH$_2$—C(O)—, —(CH$_2$)$_2$—C(O)—, —(CH$_2$)$_4$—C(O)—;
T" is —C(O)— or —C(O)—X" wherein X" is —S— or —O—, preferably T" is —C(O)— when R$^{1a}$ is selected from A5) or A6);
T" is —O—, —S—, —NR'—, —O—CH(R')—O—C(O)— wherein R' is H or a straight or branched C$_1$-C$_4$ alkyl, preferably T" is —O—, when R$^{1a}$ is selected from A7);

T is —O—, —S—, —NR'—, —O—CH(R')—O—C(O)— wherein R' is H or a straight or branched C$_1$-C$_4$ alkyl, preferably T is —O—;
Y and Y' are as below defined;
or R$_x$ is
(b1) —HN—OH(R$^2$)—CH$_2$C(O)-(T-Y—ONO$_2$)
wherein
R$^2$ of the group 131) is selected from H, CH$_3$, isobutyl, isopropyl, benzyl;
R$^2$ of the group B2) is selected from —CH$_2$—OH, —CH(CH$_3$)—OH— or —CH$_2$[(C$_6$H$_4$) (4-OH)], or
R$^2$ of the group B3) is selected from —CH$_2$—NHR", —(CH$_2$)$_2$—NHR", —(CH$_2$)$_3$—NHR", —(CH$_2$)$_4$—NHR", wherein R" is H, or —C(O)CH$_3$,
R$^2$ of the group B4) is —CH$_2$—C(O)R''', —(CH$_2$)$_2$—C(O)R''', —(CH$_2$)$_4$—C(O)R''' wherein R''' is OR$^{5a}$ wherein R$^{5a}$ is H or a linear (C$_1$-C$_5$) alkyl;
T is —O—, —S—, —NR'—, —O—CH)(R')—O—C(O)— wherein R' is H or a straight or branched C$_1$-C$_4$ alkyl, preferably T is —O—;
Y is as below defined;
or R$_x$ is selected from
(d1) —HN—CH(R$^{12}$)—CH$_2$—O-(T"-Y—ONO$_2$)
(d2) —O—CH$_2$—CH(R$^{12}$)—NH-(T'-Y—ONO$_2$)
wherein
R$^{12}$ of the group D1) is selected from H, CH$_3$, isobutyl, isopropyl, benzyl, or
R$^{12}$ of the group D2) is selected from —CH$_2$—OH, —CH(CH$_3$) OH— or —CH$_2$[(C$_6$H$_4$)—(4-OH)], or
R$^{12}$ of the group D3) is selected from —CH$_2$—NHR", —(CH$_2$)$_2$—NHR", (CH$_2$)$_3$—NHR", —(CH$_2$)$_4$—NHR" wherein R" is H, or
R$^{12}$ of the group D4) is —CH$_2$—C(O)R''', —(CH$_2$)$_2$—C(O)R''', —(CH$_2$)$_4$—C(O)R''' wherein R''' is OR$^{5a}$ wherein R$^{5a}$ is H or a linear (C$_1$-C$_5$) alkyl;
T' and T" are each independently selected from —C(O)— or —C(O)—X" wherein X" is —S— or —O—, preferably T' and T" are —C(O)—;
Y is as below defined;
or R$_x$ is selected from
(d3) —HN—CH(R$^{12a}$-T"-Y—ONO$_2$)—CH$_2$OH
(d4) —O—CH$_2$—CH(R$^{12a}$-T"-Y'—ONO$_2$)—NHR$^{4a}$
(d7) —HN—CH(R$^{12a}$-T"-Y'—ONO$_2$)—CH$_2$—O-(T"-Y—ONO$_2$) or
(d8) —O—CH$_2$—CH(R$^{12a}$-T"-Y'—ONO$_2$)—NH-(T'-Y—ONO$_2$)
wherein
R$^{12a}$ of the group D5) is selected from —CH$_2$—O—, —CH(CH$_3$)—O— or —CH$_2$[(C$_6$H$_4$)-(4-O)—], or
R$^{12a}$ of the group D6) is selected from —CH$_2$—NH—, —(CH$_2$)$_2$—NH—, (CH$_2$)$_3$—NH—, —(CH$_2$)$_4$—NH—, or
R$^{12a}$ of the group D7) is —CH$_2$—C(O)—, —(CH$_2$)$_2$—C(O)—, —(CH$_2$)$_4$—C(O)—;
R$^{4a}$ is H or —C(O)CH$_3$;
T" is selected from —C(O)— or —C(O)—X" wherein X" is —S— or —O—, preferably T' and T" are —C(O)—, when R$^{12a}$ is selected from D5) or D6);
T" is —O—, —S—, —NR'—, —O—CH(R')—O—C(O)— wherein R' is H or a straight or branched C$_1$-C$_4$ alkyl, preferably T is —O—, when R$^{12a}$ is selected from D7);
T" selected from —C(O)— or —C(O)—X" wherein X" is —S— or —O—, preferably T" is —C(O)—,
Y and Y' are as below defined;
or R$_x$ is selected from
(d5) —R$^{12b}$—CH(NHR$^{4a}$)—CH$_2$—O-(T"-Y—ONO$_2$)
(d6) —R$^{12b}$—CH(CH$_2$OH)—NH-(T'-Y—ONO$_2$)

(d9) —$R^{12b}$—CH(NH-T'-Y'—$ONO_2$)—$CH_2$—O-(T"-Y—$ONO_2$) or (d10) —$R^{12b}$—CH($CH_2$—O-T"-Y'—$ONO_2$)—NH-(T'-Y—$ONO_2$)

wherein
$R^{12b}$ of the group D8) is selected from —O—CH($CH_3$)—, —O—$CH_2$—, $O_p$ ($C_6H_4$)—$CH_2$—, or
$R^{12b}$ of the group D9) is selected from —HN—$CH_2$—, —HN—$(CH_2)_2$—,
HN—$(CH_2)_3$—, —HN—$(CH_2)_4$—;
$R^{4a}$ is H or —C(O)—$CH_3$,
T' and T" are each independently selected from —C(O)—, —C(O)—X", wherein X" is —S— or —O—, preferably T' and T" are —C(O)—;
Y and Y' are each independently selected from
a)
  a straight or branched $C_1$-$C_{10}$ alkylene,
  a straight or branched $C_1$-$C_{10}$ alkylene substituted with a —$ONO_2$ group;

d)

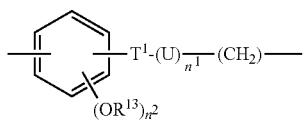

wherein:
$n^2$ is an integer from 0 to 2, $R^{13}$ is H or $CH_3$, $T_1$ is —O—C(O)— or —C(O)O—;
$n^1$ is 1 and U is a linear $C_1$-$C_{10}$ alkylene or U is a linear or branched $C_1$-$C_{10}$ alkylene substituted with a —$ONO_2$ group;

e)

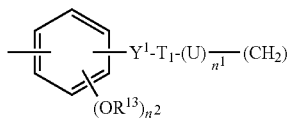

$n^2$ is 1, $R^{13}$ is $CH_3$, Y is —CH=CH—$(CH_2)_{n^{2'}}$— and $n^{2'}$ is 0, $T_1$ is —C(O)O— and U is a linear $C_1$-$C_{10}$ alkylene;

e')

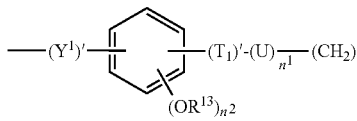

wherein:
$n^2$ is 1, $R^{13}$ is $CH_3$;
$Y^1$ is —$(CH_2)_{n^{2'}}$—CH=CH— and $n^{2'}$ is 0;
$(T_1)'$=—O—C(O)—;
$n^1$ is 1 and U is a linear $C_1$-$C_{10}$ alkylene or U is a linear or branched $C_1$-$C_{10}$ alkylene substituted with a —$ONO_2$ group;
when Y and Y' are selected from d), e) or e'), the —$ONO_2$ group of -(T-Y—$ONO_2$), -(T'-Y—$ONO_2$), -(T"-Y'—$ONO_2$)- (T'-Y'—$ONO_2$) (T"'-Y—$ONO_2$) and -(T"-Y'—$ONO_2$) is linked to the —($CH_2$)— group;

f)
$$—(CH_2—CH_2—T_2)_{\overline{n^3}}—CH_2—CH_2—$$

wherein $T_2$ is —O— or —S—, —NH—, preferably $T_2$ is —O—, $n^3$ is 1 or 2;

Another embodiment of the present invention relates to compounds of formula (I) wherein
R is the corticosteroid of formula (II) as above defined;
a is 0,
$R_x$ is
(a2) —C(O)—CH($R^1$)—NH-(T'-Y—$ONO_2$)
wherein
$R^1$ of A1) is selected from H
T' is —C(O)—;
Y is selected from
a)
  a straight or branched $C_1$-$C_{10}$ alkylene,
  a straight or branched $C_1$-$C_{10}$ alkylene substituted with a —$ONO_2$ group;

d)

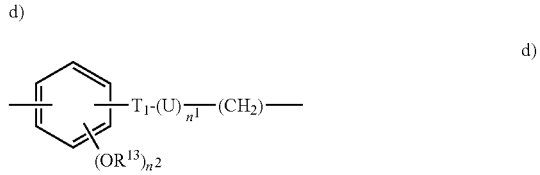

wherein:
$n^2$ is an integer from 0 to 2, $R^{13}$ is H or $CH_3$, $T_1$ is —O—C(O)— or —C(O)O—;
$n^1$ is 1 and U is a linear $C_1$-$C_{10}$ alkylene or U is a linear or branched $C_1$-$C_{10}$ alkylene substituted with a —$ONO_2$ group;

e)

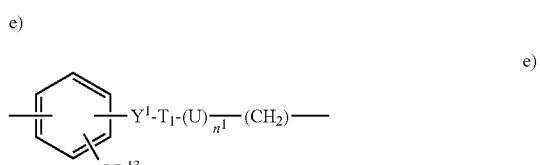

$n^2$ is 1, $R^{13}$ is $CH_3$, $Y^1$ is —CH=CH—$(CH_2)_{n^{2'}}$ and $n^{2'}$ is 0, $T_1$ is —C(O)O— and U is a linear $C_1$-$C_{10}$ alkylene;

e')

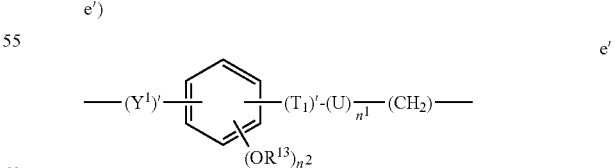

wherein:
$n^2$ is 1, $R^{13}$ is $CH_3$;
$Y^1$ is —$(CH_2)_{n^{2'}}$—CH=CH— and $n^{2'}$ is 0;
$(T_1)'$=—O—C(O)—;
n is 1 and U is a linear $C_1$-$C_{10}$ alkylene or U is a linear or branched $C_1$-$C_{10}$ alkylene substituted with a —$ONO_2$ group;

when Y and Y' are selected from d), e) or e∝0), the —ONO$_2$ group of -(T'-Y—ONO$_2$) is linked to the —(CH$_2$)— group;

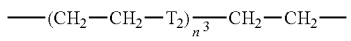   f)

wherein T$_2$ is —O— or —S—, —NH—, preferably T$_2$ is —O—, n$^3$ is 1 or 2;

Another embodiment relates to compounds of formula (I) wherein R is the corticosteroid of formula (II) as above defined;
a is 0, R$_x$ is
(a5) —R$^{1b}$—CH(NHR$^{4a}$)—C(O)-(T-Y—ONO$_2$) or
(a9) —R$^{1b}$—CH(NH-T'-Y'—ONO$_2$)—C(O)-(T-Y—ONO$_2$)
wherein
R$^{1b}$ of A10) is —C(O)—CH$_2$—,
R$^{4d}$ is H or —C(O)CH$_3$;
T is selected from —O—, —S—, —NR'— wherein R' is as above defined,
T' is —C(O)— and
Y and Y' are each independently selected from
a)
 a straight or branched C$_1$-C$_{10}$ alkylene,
 a straight or branched C$_1$-C$_{10}$ alkylene substituted with a —ONO$_2$ group;

d)

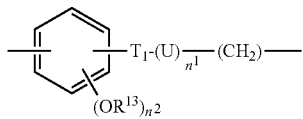   d)

wherein:
n$^2$ is an integer from 0 to 2, R$^{13}$ is H or CH$_3$, T$_1$ is —O—C(O)— or —C(O)O—;
n is 1 and U is a linear C$_1$-C$_{10}$ alkylene or U is a linear or branched C$_1$-C$_{10}$ alkylene substituted with a —ONO$_2$ group;

e)

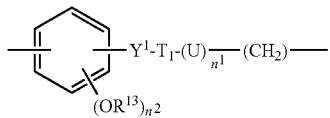   e)

n$^2$ is 1, R$^{13}$ is CH$_3$, T$^1$ is —CH=CH—(CH$_2$)$_n{^{2'}}$— and n$^{2'}$ is 0, T$_1$ is —C(O)O— and U is a linear C$_1$-C$_{10}$ alkylene;

e')

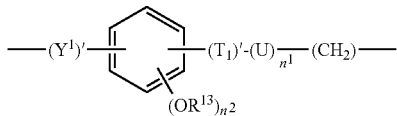   e' wherein:
n$^2$ is 1, R$^{13}$ is CH$_3$;
Y is —(CH$_2$)$_n{^{2'}}$—CH=CH— and n$^{2'}$ is 0;
(T$_1$)$^1$=—O—C(O)—;
n is 1 and U is a linear C$_1$-C$_{10}$ alkylene or U is a linear or branched C$_1$-C$_{10}$ alkylene substituted with a —ONO$_2$ group;

when Y and Y' are selected from d), e) or e), the —ONO$_2$ group of -(T-Y—ONO$_2$), -(T'-Y—ONO$_2$), -(T"-Y'—ONO$_2$), -(T"'-Y'—ONO$_2$), (T"-Y—ONO$_2$) and -(T"'-Y'—ONO$_2$) is linked to the —(CH$_2$)— group;

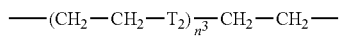   f)

wherein T$_2$ is —O— or —S—, —NH—, preferably T$_2$ is —O—, n$^3$ is 1 or 2;

Another embodiment relates to compounds of formula (I) wherein R is the corticosteroid of formula (II) as above defined;
a is 1 and Z is —C(O)—, R$_x$ is
(a5) —R$^{1b}$—(NHR$^{4a}$)—C(O)-(T-Y—ONO$_2$) or
(a9) —R$^{1b}$—CH(NH-T'-Y'—ONO$_2$)—C(O) (T-Y—ONO$_2$)
wherein R$^{1b}$ of A10) is —O—CH$_2$— or [—O$_p$—(C$_6$H$_4$)]—CH$_2$—,
R$^{4a}$ is H or —C(O)CH$_3$,
T is selected from —O—, —S—, —NR'— wherein R' is as above defined,
T' is —C(O)— and
Y and Y' are each independently selected from
a)
 a straight or branched C$_1$-C$_{10}$ alkylene,
 a straight or branched C$_1$-C$_{10}$ alkylene substituted with a —ONO$_2$ group;

d)

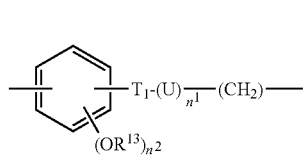   d)

wherein:
n$^2$ is an integer from 0 to 2, R$^{13}$ is H or CH$_3$, T$_1$ is —O—C(O)— or —C(O)O—;
n$^1$ is 1 and U is a linear C$_1$-C$_{10}$ alkylene or U is a linear or branched C$_1$-C$_{10}$ alkylene substituted with a —ONO$_2$ group;

e)

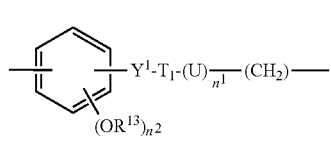   e)

n$^2$ is 1, R$^{13}$ is CH$_3$, Y$^1$ is —CH=CH—(CH$_2$)$_n{^{2'}}$— and n$^{2'}$ is 0, T$_1$ is —C(O)O— and U is a linear C$_1$-C$_{10}$ alkylene;

e')

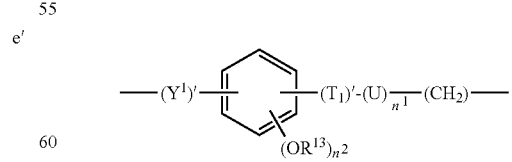   e' wherein:
n$^2$, is 1, R$^{13}$ is CH$_3$;
Y$^1$ is —(CH$_2$)$_n{^{2'}}$—CH=CH— and n$^{2'}$ is 0;
(T$_1$)'=—O—C(O)—;
n$^1$ is 1 and U is a linear C$_1$-C$_{10}$ alkylene or U is a linear or branched C$_1$-C$_{10}$ alkylene substituted with a —ONO$_2$ group;

when Y and Y' are selected from d), e) or e'), the —ONO$_2$ group of -(T-Y—ONO$_2$), -(T'-Y—ONO$_2$), -(T"-Y'—ONO$_2$), -(T'-Y'—ONO$_2$), -(T"-Y—ONO$_2$) and -(T"-Y'—ONO$_2$) is linked to the —(CH$_2$)— group;

$$—(CH_2—CH_2—T_2)_{\overline{n^3}}CH_2—CH_2— \qquad f)$$

wherein T$_2$ is —O— or —S—, —NH—, preferably T$_2$ is —O—, n$^3$ is 1 or 2;

Another embodiment of the present invention relates to compounds of formula (I) wherein
R is the corticosteroid of formula (II) as above defined;
a is 0,
R$_x$ is
(b2) —C(O)—CH$_2$—CH(R$^2$)—NH-(T'-Y—ONO$_2$)
wherein
R$^2$ of B1) is H,
T' is —C(O)—;
Y and Y' are each independently selected from
a)
    a straight or branched C$_1$-C$_{10}$ alkylene,
    a straight or branched O$_1$—C$_{10}$ alkylene substituted with a —ONO$_2$ group;

d)

wherein:
n$^2$ is an integer from 0 to 2, R$^{13}$ is H or CH$_3$, T$_1$ is —O—C(O)— or —C(O)O—;
n$^1$ is 1 and U is a linear C$_1$-C$_{10}$ alkylene or U is a linear or branched C$_1$-C$_{10}$ alkylene substituted with a —ONO$_2$ group;

e)

n$^2$ is 1, R$^{13}$ is CH$_3$, Y$^1$ is —CH═CH—(CH$_2$)$_n{^{2'}}$ and n$^{2'}$ is 0, T$_1$ is —C(O)O— and U is a linear C$_1$-C$_{10}$ alkylene;

e')

wherein:
n$^2$ is 1, R$^{13}$ is CH$_3$;
Y$^1$ is —(CH$_2$)$_n{^{2'}}$—CH═CH— and n$^{2'}$ is 0;
(T$_1$)'═—O—C(O)—;
n$^1$ is 1 and U is a linear C$_1$-C$_{10}$ alkylene or U is a linear or branched C$_1$-C$_{10}$alkylene substituted with a —ONO$_2$ group;
when Y and Y' are selected from d), e) or e'), the —ONO$_2$ group of -(T-Y—ONO$_2$)-(T'-Y—ONO$_2$), -(T"-Y'—ONO$_2$), -(T'-Y'—ONO$_2$), -(T"'-Y—ONO$_2$) and -(T"-Y'—ONO$_2$) is linked to the —(CH$_2$)— group;

$$—(CH_2—CH_2—T_2)_{\overline{n^3}}CH_2—CH_2— \qquad f)$$

wherein T$_2$ is —O— or —S—, —NH—, preferably T$_2$ is —O—, n$^3$ is 1 or 2;

Preferred specific embodiments of the present invention are the selected compounds of formula below reported:

(1)

(2)

(3)

(4)

-continued
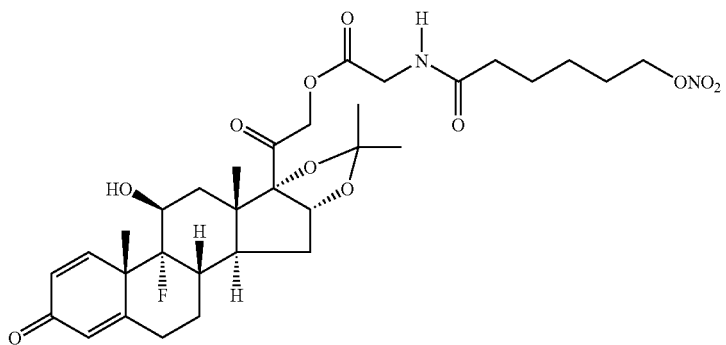
(5)
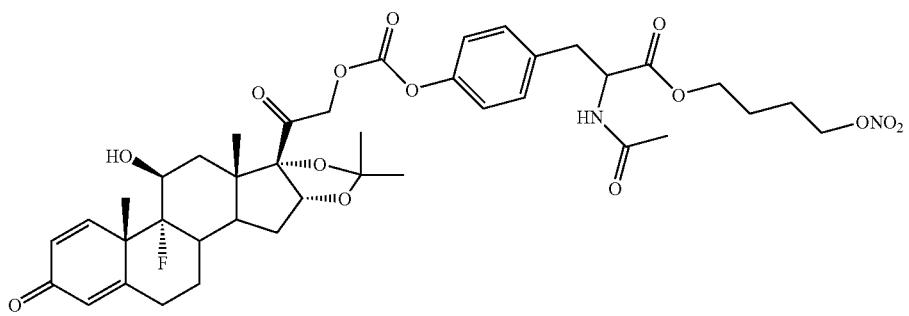
(6)
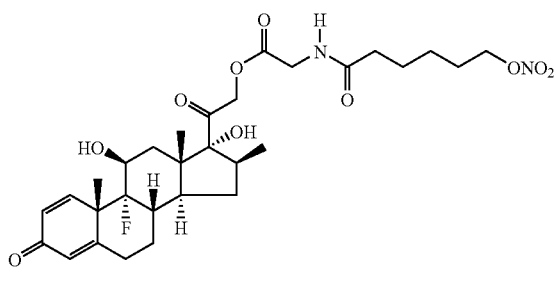
(7)
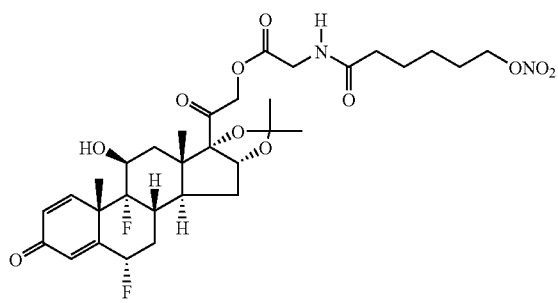
(8)
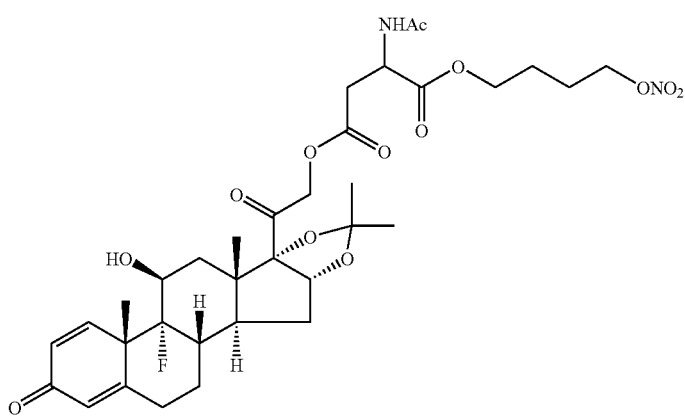
(9)

-continued
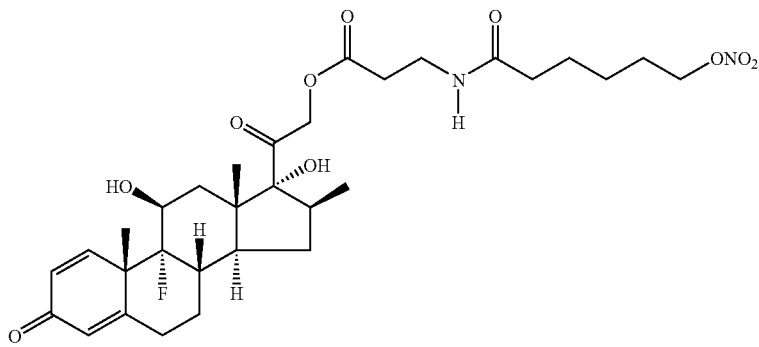
(10)
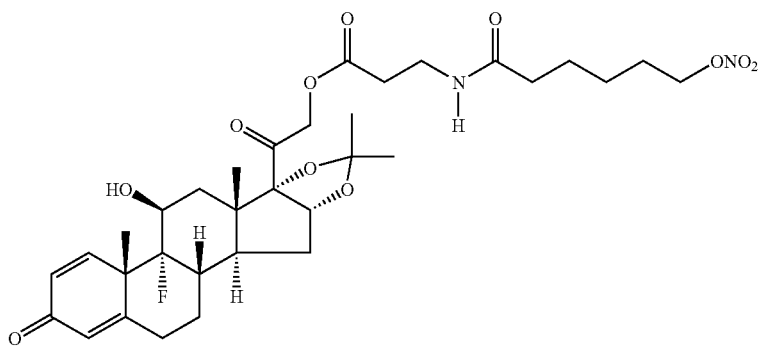
(11)
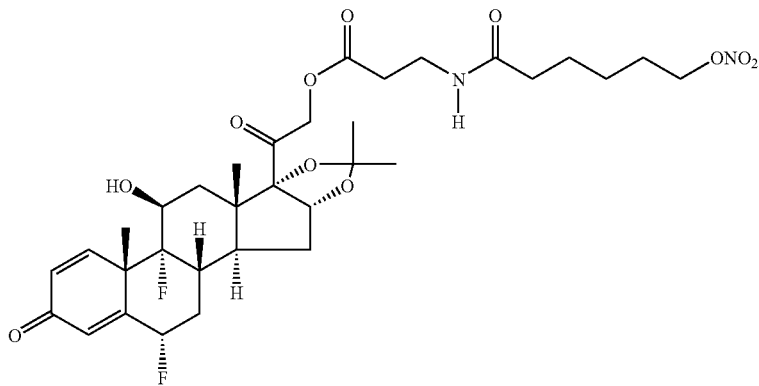
(12)
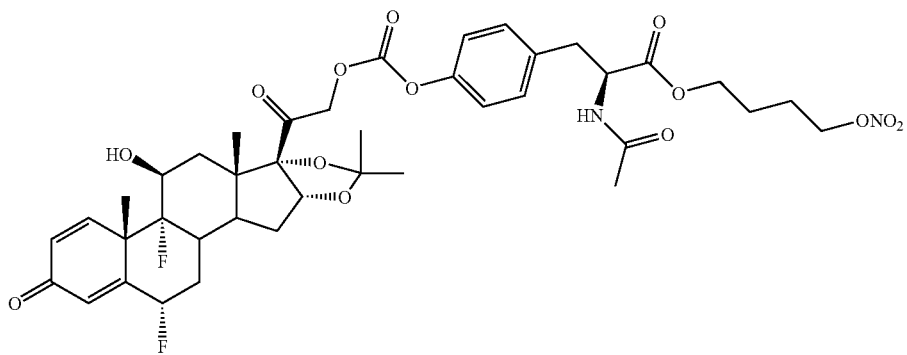
(13)

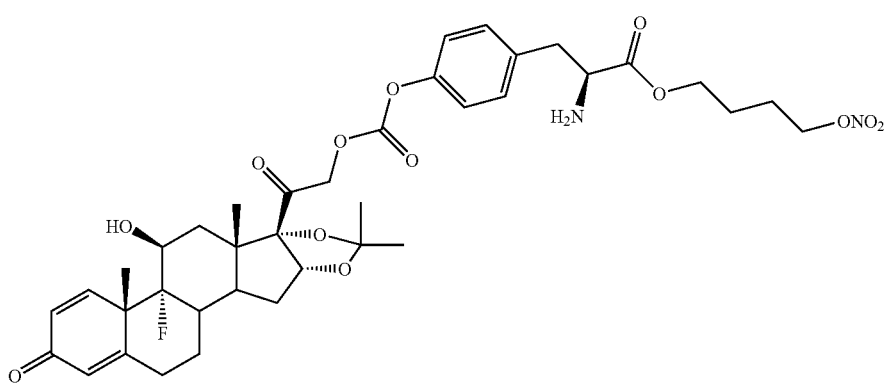
(14)
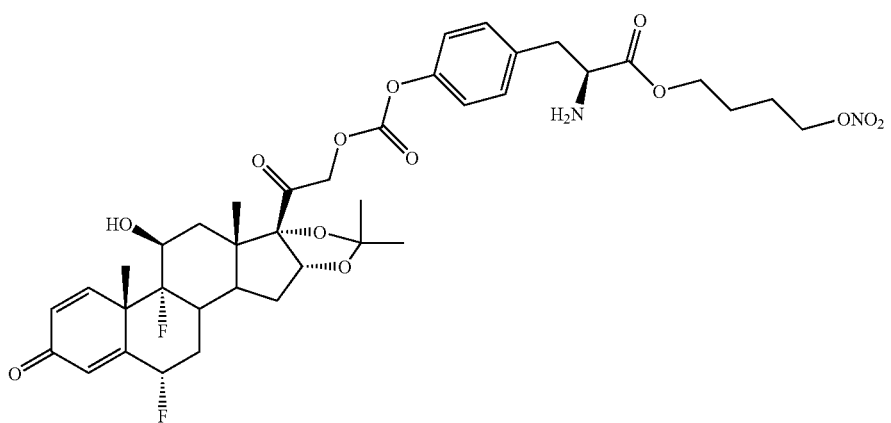
(15)
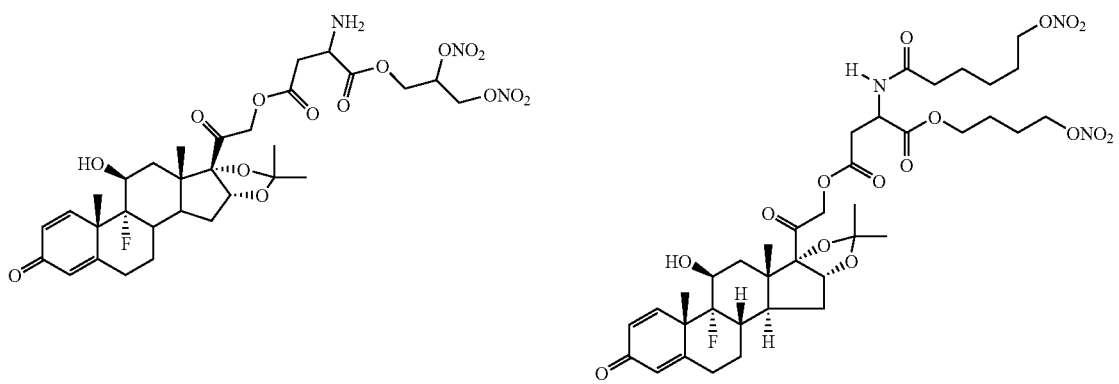
(16) (17)
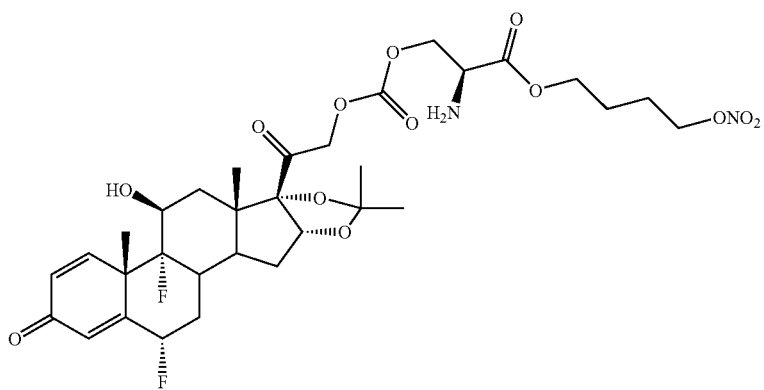
(18)

-continued
(19)
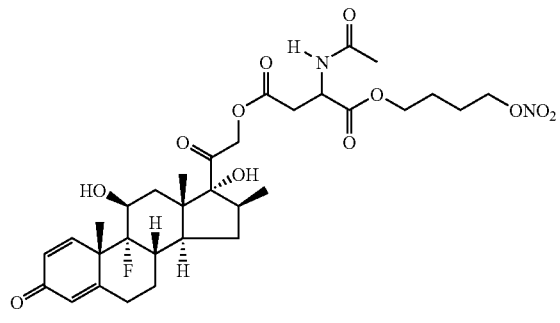
(20)
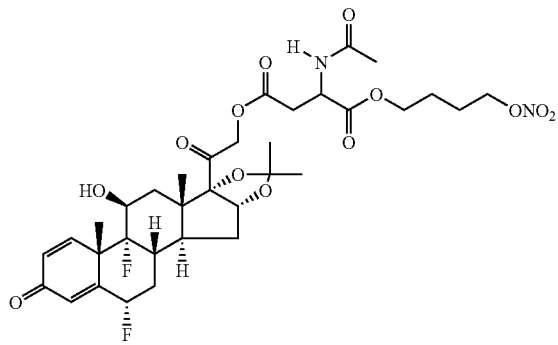
(21)
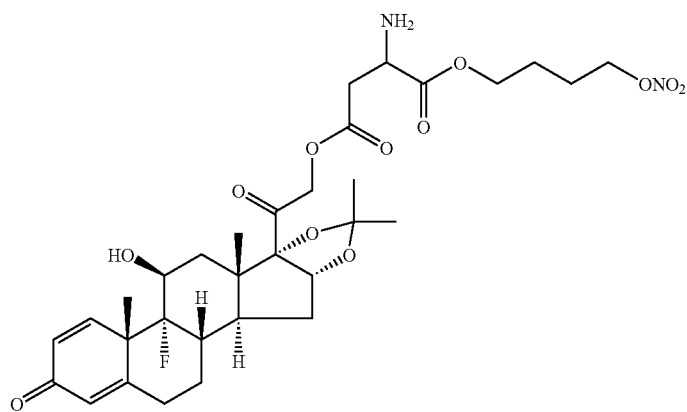
(22)
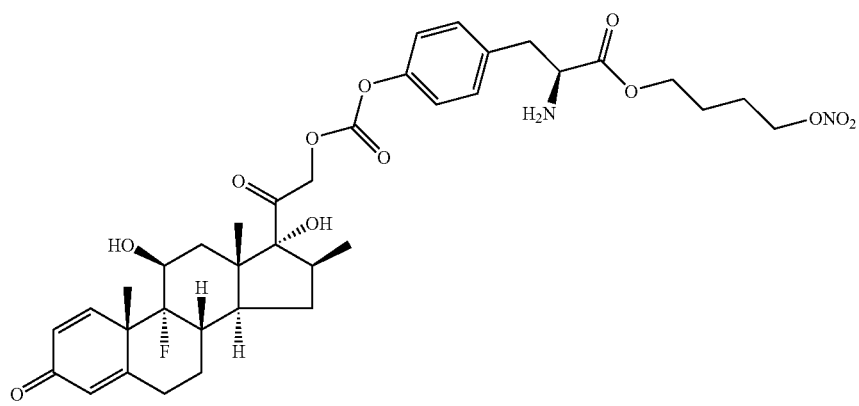
(23)
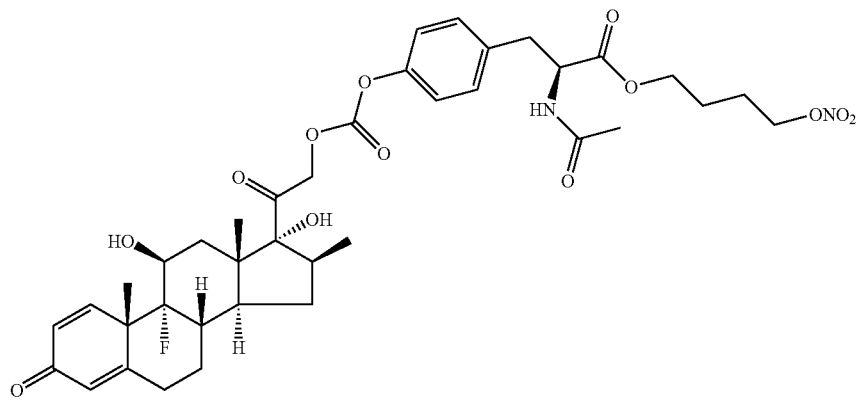

-continued
(24)
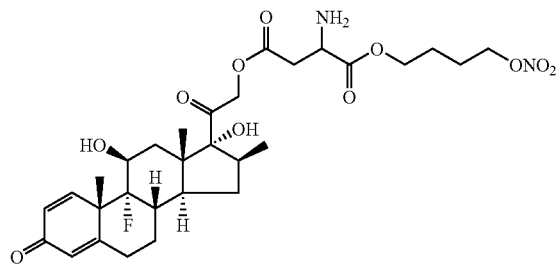
(25)
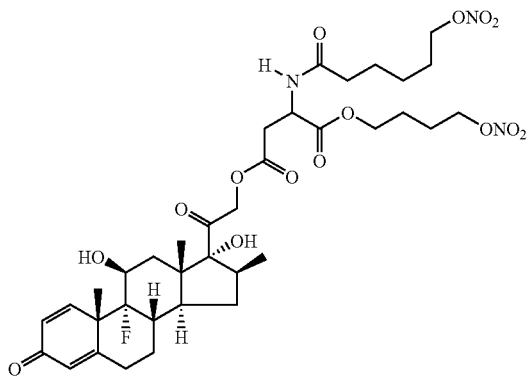
(26)
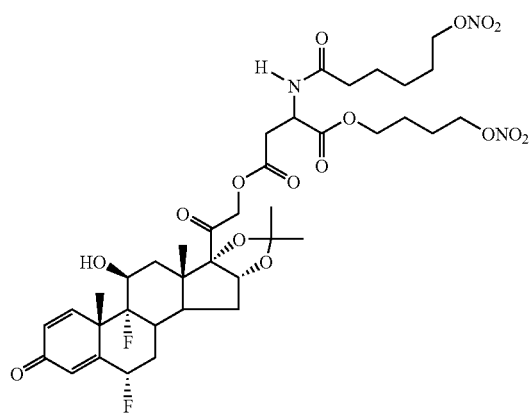
(27)
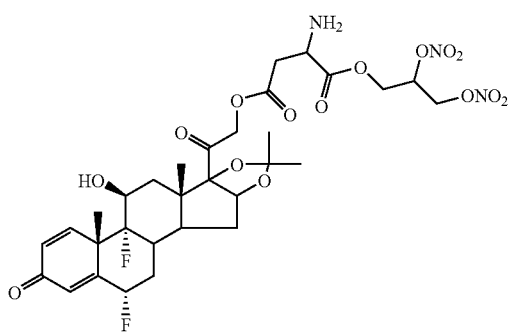
(28)
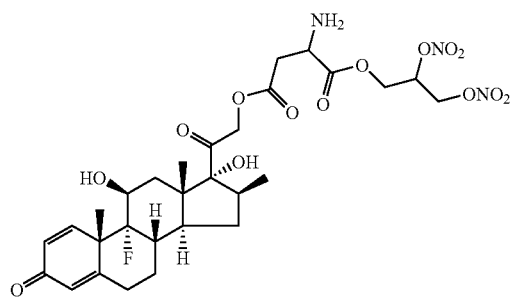
(29)
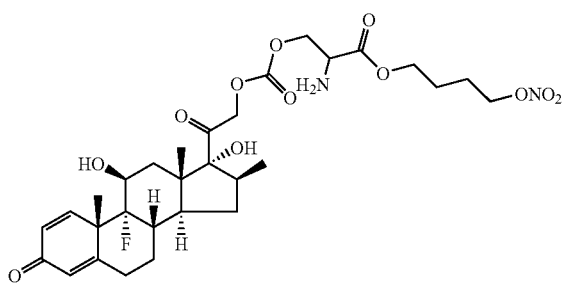
(30)
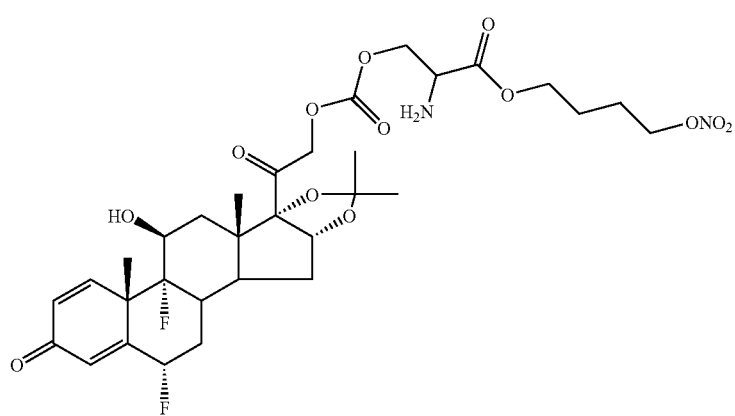

-continued

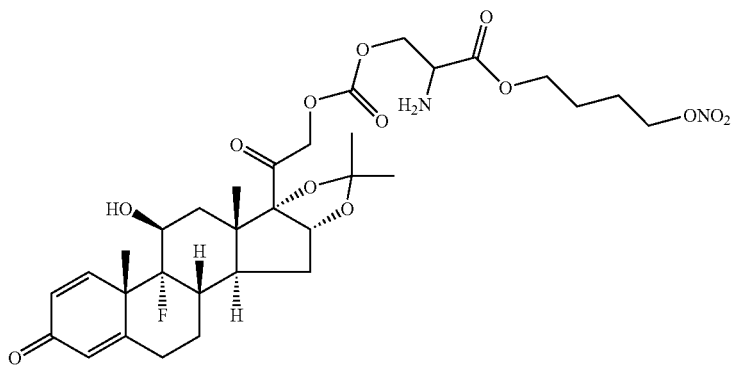

(31)

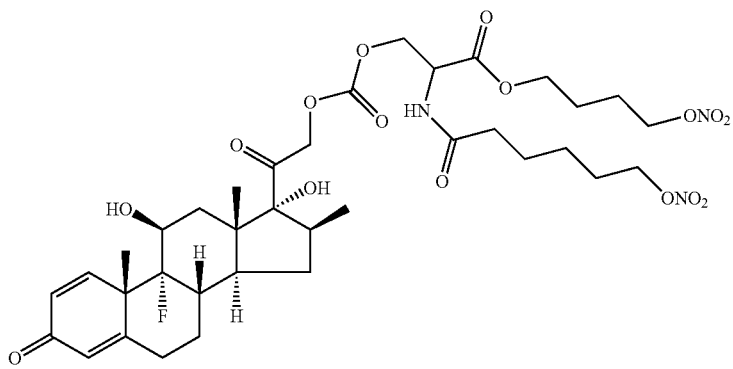

(32)

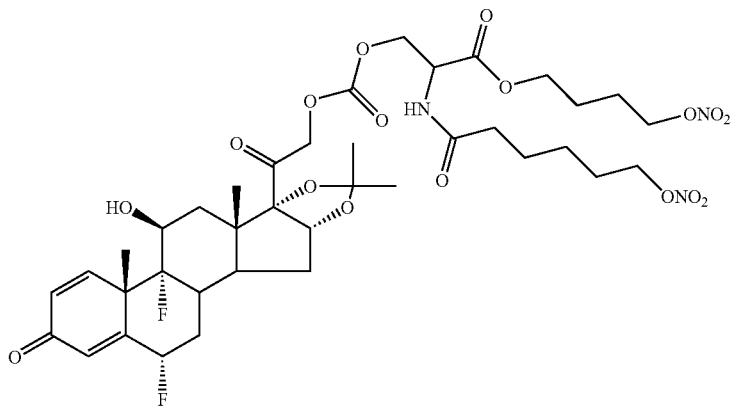

(33)

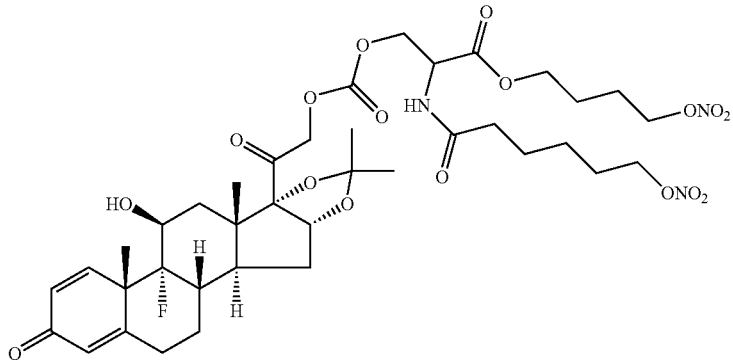

(34)

As stated above, the invention includes also the pharmaceutically acceptable salts of the compounds of formula (I) and stereoisomers thereof.

Examples of pharmaceutically acceptable salts are either those with inorganic bases, such as sodium, potassium, calcium and aluminium hydroxides, or with organic bases, such as lysine, arginine, triethylamine, dibenzylamine, piperidine and other acceptable organic amines.

The compounds according to the present invention, when they contain in the molecule one salifiable nitrogen atom, can be transformed into the corresponding salts by reaction in an organic solvent such as acetonitrile, tetrahydrofuran with the corresponding organic or inorganic acids.

Examples of organic acids are: oxalic, tartaric, maleic, succinic, citric acids. Examples of inorganic acids are: nitric, hydrochloric, sulphuric, phosphoric acids. Salts with nitric acid are preferred.

The compounds of the invention which have one or more asymmetric carbon atoms can exist as optically pure enantiomers, pure diastereomers, enantiomers mixtures, diastereomers mixtures, enantiomer racemic mixtures, racemates or racemate mixtures. Within the object of the invention are also all the possible isomers, stereoisomers and their mixtures of the compounds of formula (I).

The compounds object of the present invention are formulated in the corresponding pharmaceutical compositions, also with belated release, for parenteral, oral and topic use, such as for example sublingual, inhalatory, suppository, transdermal, enema, according to the well known techniques in the art, together with the usual excipients; see for example the publication "Remington's Pharmaceutical Sciences" 15$^{th}$ Ed.

The amount on a molar basis of the active principle in said compositions is generally the same, or lower than that of the corresponding precursor drug.

The daily administrable doses are those of the precursor drugs, or optionally lower. The precursor daily doses can be found in the publications of the field, such for example in the "Physician's Desk reference".

The present invention compounds are used in particular for the treatment of ocular disease therapies such as ocular hypertension, age-related macular degeneration, diabetic macular edema, diabetic retinopathy, hypertensive retinopathy and retinal vasculopathies.

Synthesis Procedure

1) The compound of general formula (I) as above defined wherein a is equal to 0, the radical $R_x$ is selected from (a2), (a4), (a8), (b2), (b4), (b8), (c2), (e2), (f1), (g2), (h1), (i1), (l2), (m2), (n2), (o2), (p2), (q2), (r2), (s2), (t2), (u2), (v2), can be obtained:

1-i) by reacting a compound of (IIa)

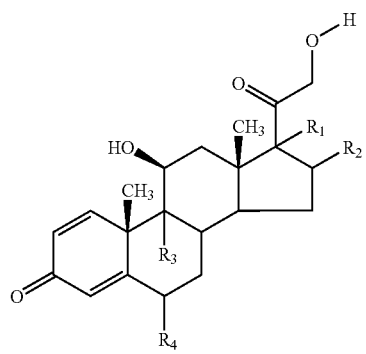

wherein $R_1$, $R_2$, $R_3$, $R_4$, are as above defined, with a compound of formula (Ia)

W—$X_1$ (Ia)

wherein W is —OH, Cl, O—$R_a$, wherein $R_a$ is pentafluorophenyl, 4-nitrophenyl or —(N-succinimidyl), $X_1$ is below defined, to obtain the compound of formula (IIa')

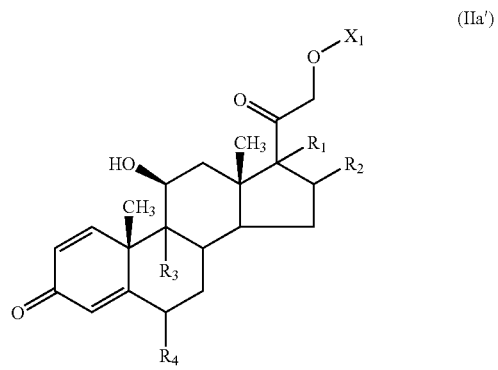

wherein $R_1$, $R_2$, $R_3$, $R_4$, are as above defined and $X_1$ is as below defined, $X_1$ is a radical having the following meaning:
(a2') —C(O)—CH($R^{1'}$)—NH-(T'-Y-Q)
wherein $R^{1'}$ is selected from
A1) as defined above or
A2') —CH$_2$—SP$^1$, —CH$_2$—OP$^1$, —CH(CH$_3$) —OP$^1$, —CH$_2$[(C$_6$H$_4$)-4-OP$^1$]—CH$_2$—[(C$_6$H$_3$)-(3,5-diiodo)-4-OP$^1$], —(CH$_2$—[(C$_6$H$_3$)-3-nitro-4-OP$^1$] or
A3') —CH$_2$—NHR'''', —(CH$_2$)$_2$—NHR'''', —(CH$_2$)$_3$—NHR'''', —(CH$_2$)$_4$—NHR'''', wherein R'''' is P$^3$ or —C(O)CH$_3$ or

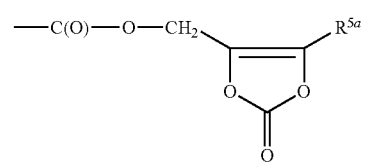

wherein $R^{5a}$ is as defined above;
A4') —CH$_2$—C(O)R''''', —(CH$_2$)$_2$—C(O)R''''', —(CH$_2$)$_4$—C(O)R'''''
wherein R''''' is P$^2$, —OR$^{5a}$ or

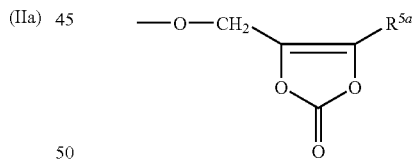

wherein $R^{5a}$ is as above defined;
(a4') —C(O)—CH($R^{1a}$-T''-Y'-Q)-NHR$^{4a'}$
(a8') —C(O)—OH($R^{1a}$-T''-Y'-Q)-NH-(T'-Y-Q)
wherein $R^{1a}$ is as defined above;
(b2') —C(O)—CH$_2$—CH($R^{2'}$)—NH-(T'-Y-Q)
wherein $R^{2'}$ is selected from
B1) as defined above or
B2') —CH(CH$_3$)—OP$^1$, —CH$_2$—[(C$_6$H$_4$)$_4$—OP$^1$];
B3') —CH$_2$—NHR'''', —(CH$_2$)$_2$—NHR''''—(CH$_2$)$_3$—NHR'''', —(CH$_2$)$_4$—NHR'''',
wherein R'''' is above defined;
B4') —CH$_2$—C(O)—R''''', —(CH$_2$)$_2$—C(O)—R''''', —(CH$_2$)$_4$—C(O)—R''''' wherein
R''''' is as above defined;
$R^{4a'}$ is P$^3$ or —C(O)—CH$_3$ or

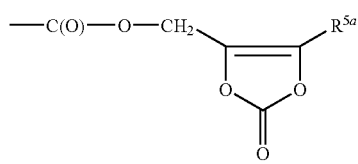

(b4') —C(O)—CH$_2$—CH(R$^{2a}$-T''-Y'-Q)-NHR$^{4a'}$
(b8') —C(O)—CH$_2$—CH(R$^{2a}$-T''-Y'-Q)-NH-(T'-Y-Q)
wherein R$^{2a}$ and R$^{4a'}$ are as defined above;
(c2') —C(O)—(CH$_2$)$_b$—NH-(T'-Y-Q);

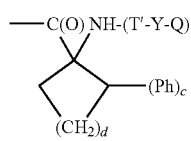 (e2')

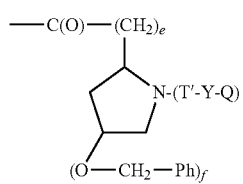 (f1')

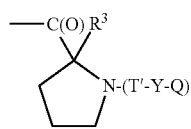 (g2')

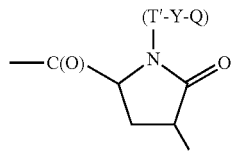 (h1')

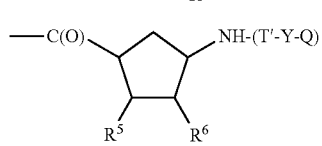 (i1')

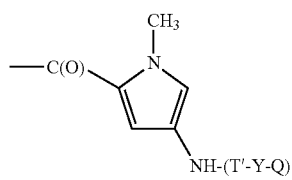 (l2')

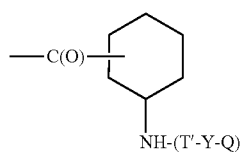 (m2')

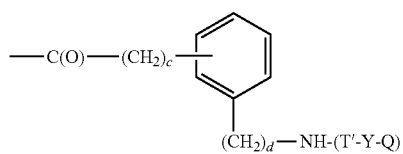 (n2')

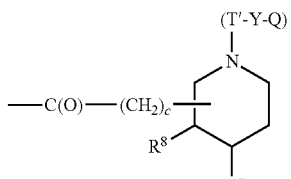 (o2')

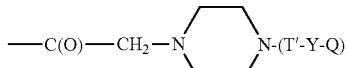 (p2')

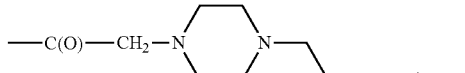 (q2')

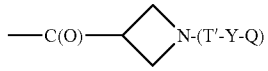 (r2')

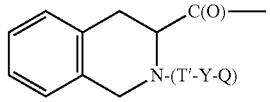 (s2')

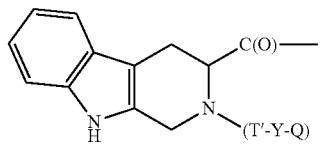 (t2')

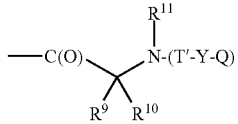 (u2')

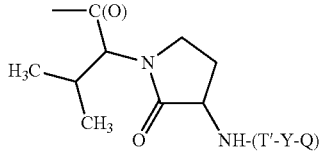 (v2')

wherein R$^3$, R$^4$, R$^5$, R$^6$, R$^7$, R$^8$, R$^9$, R$^{10}$, R$^{11}$, b, c, d, e and f are as above defined;

wherein P$^1$ is a hydroxyl or thiol protecting group such as silyl ethers, such as trimethylsilyl, tert-butyl-dimethylsilyl or trityl and those described in T. W. Greene "Protective groups in organic synthesis", Harvard University Press, 1980, P$^2$ is a carboxylic protecting group such as tert-butyl ester and those described in T. W. Greene "Protective groups in organic synthesis", Harvard University Press, 1980, P$^3$ is a amino protecting group such as Boc, Fmoc or those described in T. W. Greene "Protective groups in organic synthesis", Harvard University Press, 1980, T, T', T'', Y and Y' are as above defined, Q is independently —ONO$_2$ or Z$_2$ wherein Z$_2$ is selected from the group consisting of: a chlorine atom, a bromine atom, a iodine atom, a mesyl group or a tosyl group, and 1-ii) when Q is Z$_{2r}$ by converting the compound obtained in the step 1-i) into nitro derivative by reaction with a nitrate source such as silver nitrate, lithium nitrate, sodium nitrate, potassium nitrate, magnesium nitrate, calcium nitrate, iron nitrate, zinc nitrate or tetraalkylammonium nitrate (wherein alkyl is $C_1$-$C_{10}$alkyl) in a suitable organic solvent such as acetonitrile, tetrahydrofurane, methyl ethyl ketone, ethyl acetate, DMF, the reaction is carried out, in the dark, at a temperature from room temperature to the boiling temperature of the solvent. Preferred nitrate source is silver nitrate and
1-iii) optionally deprotecting the compounds obtained in step 1-i) or 1-ii) as described in T. W. Greene "Protective groups in organic synthesis", Harvard University Press, 1980, $2^{nd}$ edition. Fluoride ion is the preferred method for removing silyl ether protecting group. Trifluoroacetic acid or anhydrous inorganic acid are the preferred method for removing Boc protecting group, anhydrous organic or inorganic acid is the preferred method for removing trityl protecting group. Organic base such as piperidine is the preferred method for removing Fmoc protecting group. Aqueous or anhydrous organic or inorganic acid is the preferred method for removing t-butyl ester protecting group.

1-i-1) The reaction of a compound of formula (Ia) wherein W=—OH and $X_1$ is as above defined, with a compound of formula (IIa) may be carried out in presence of a condensing agent as dicyclohexylcarbodiimide (DCC), N'-(3-dimethylaminopropyl)-N-ethylcarbodiimide hydrochloride (EDAC) N,N'-carbonyldiimidazole (CDI), in the presence or not of a base as for example as N,N-dimethylamino pyridine (DMAP).

The reaction is carried out in an inert organic dry solvent such as N,N'-dimethylformamide, tetrahydrofuran, benzene, toluene, dioxane, a polyhalogenated aliphatic hydrocarbon at a temperature from −20° C. and 50° C. The reaction is completed within a time range from 30 minutes to 36 hours.

1-i-2) The reaction of a compound of formula (Ia) wherein W=—O—R, wherein $R_a$ and $X_1$ are as above defined, with a compound of formula (IIa) may be carried out in presence of a catalyst, such as N,N-dimethylamino pyridine (DMAP) or in the presence of DMAP and a Lewis acid such as Sc(OTf)$_3$ or Bi(OTf)$_3$.

The reaction is carried out in an inert organic solvent such as N,N'-dimethylformamide, tetrahydrofuran, benzene, toluene, dioxane, a polyhalogenated aliphatic hydrocarbon at a temperature from −20° C. and 40° C. The reaction is completed within a time range from 30 minutes to 36 hours.

1-i-3) The reaction of a compound of formula (Ia) wherein W=—Cl, and $X_1$ is are as above defined, with a compound of formula (IIa) may be carried out in presence of an organic base such as N,N-dimethylamino pyridine (DMAP), triethylamine, pyridine. The reaction is carried out in an inert organic solvent such as N,N'-dimethylformamide, tetrahydrofuran, benzene, toluene, dioxane, a polyhalogenated aliphatic hydrocarbon at a temperature from −20° C. and 40° C. The reaction is completed within a time range from 30 minutes to 36 hours.

The compounds of formula (IIa) are commercially available.

1a) The compounds of formula (Ia) wherein W is —OH, T' and T" are C(O), and $X_1$ is the radical selected from (a2'), (a4'), (b2'), (b4'), (c2'), (e2'), (f1'), (g2'), (h1'), (i1'), (l2'), (m2'), (n2'), (o2'), (p2'), (q2'), (r2'), (s2'), (t2'), (u2'), (v2'), wherein $R^{1'}$ is selected from A1), A2'), A3'), A4'), $R^{1a}$ is selected from A5) or A6), $R^{2a}$ is selected from B5) or B6) and $R^{2'}$ is selected from B1), B2'), B3'), B4') and Y, Y' and $R^{4a'}$ are as above defined, can be obtained 1a-i) by reacting a compound of formula (IIIa)

$$P^2\text{—}X_2 \qquad \text{(IIIa)}$$

wherein $P^2$ is as above defined, $X_2$ is a radical having the following meaning (a2") —C(O)—CH($R^{1'}$)—NH$_2$ (a4") —C(O)—CH($R^{1a}$—H)—NHR$^{4a'}$ wherein $R^{1'}$ is selected from A1), A2'), A3'), A4'), $R^{1a}$ is selected from A5) or A6) and $R^{4a'}$ is as defined above (b2") —C(O)—CH$_2$—CH($R^{2'}$)—NH$_2$, (b4") —C(O)—CH$_2$—CH($R^{2a}$—H)—NHR$^{4a'}$ wherein $R^{2'}$ is selected from B1), B2'), B3'), B4'), $R^{2a}$ is selected from B5) or B6) and $R^{4a'}$ is as defined above, (c2") —C(O)—(CH$_2$)$_b$—NH$_2$,

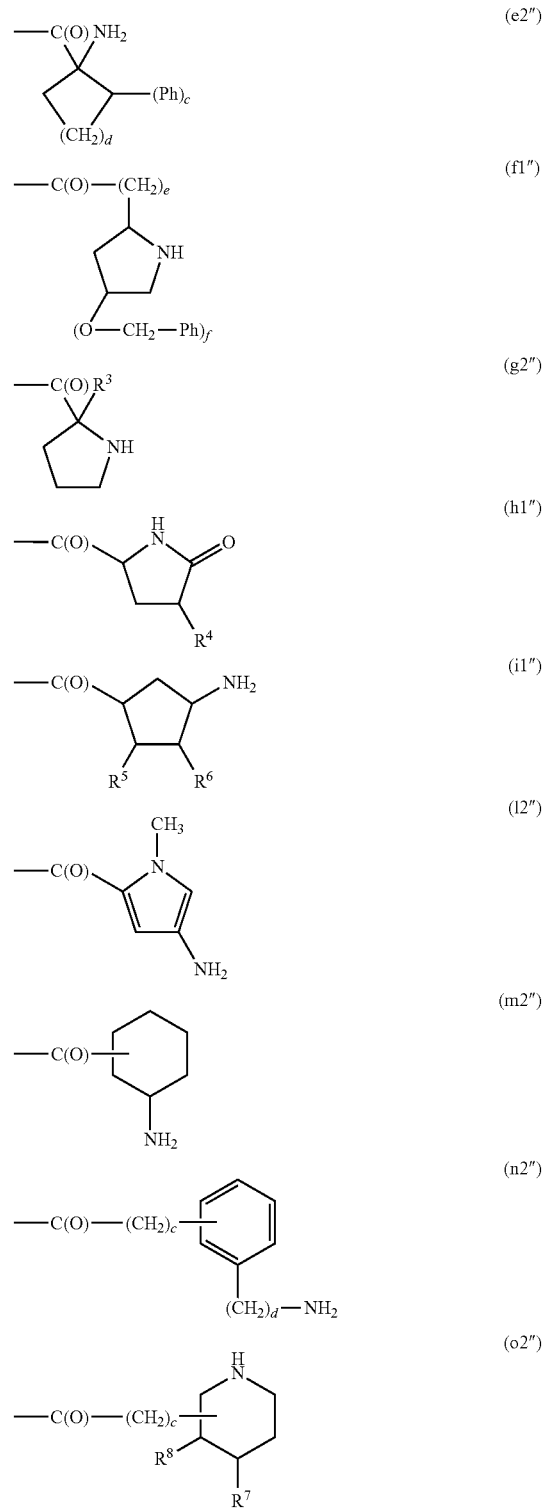

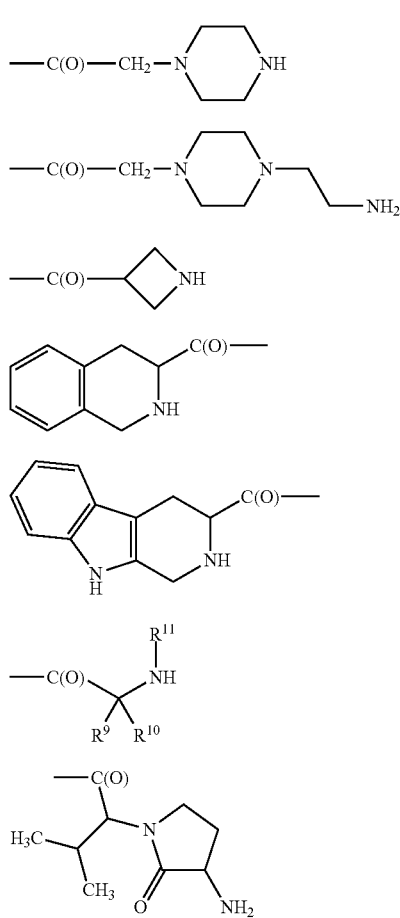

wherein $R^3$, $R^4$, $R^5$, $R^6$, $R^7$, $R^8$, $R^9$, $R^{10}$, $R^{11}$, b, c, d, e and f are as above defined;
with a compound of formula (IVa)

$$W_1\text{—(O)C-}y\text{-Q} \tag{IVa}$$

wherein $W_1$ is OH or O—$R_a$, and $R_a$ and Q are as above defined, y is the radical Y when $X_2$ is selected from (a2'), (b2'), (c2'), (e2'), (f1'), (g2'), (h1'), (i1'), (l2'), (m2'), (n2'), (o2'), (p2'), (q2'), (r2'), (s2'), (t2'), (u2'), (v2'), and y is the radical Y' when $X_2$ is selected from (a4') or (b4'), wherein Y and Y' are as defined above, and 1a-ii) when Q is $Z_2$, by converting the compound obtained in the step 1a-i) into nitro derivative by reaction with a nitrate source as above described and 1a-iii) optionally deprotecting the compounds obtained in step 1a-i) or 1a-ii) as above described.

The reaction of a compound of formula (IIIa) wherein $P^2$ and $X_2$ are as above defined, with a compound of formula (IVa) wherein $W_1$ is OH, y, Q are as above defined, may be carried out as described in 1-i-1) or in presence of other known condensing reagents such as O-(7-azabenzotriazol-1-yl)-N,N,N',N'-tetramethyluronium hexafluorophosphate (HATU).

The reaction of a compound of formula (IIIa) wherein $P^2$ and $X_2$ are as above defined, with a compound of formula (IVa) wherein $W_1$ is O—$R_a$, y, Q are as above defined, may be carried as described in 1-i-2).

The compounds of formula (IIIa) are commercially available or can be obtained as known in the literature.

The compounds of formula (IVa) wherein $W_1$ is OH, y and Q are as above defined, can be obtained from the corresponding alcohols of formula HOOC-y-OH (IVb) by reaction with nitric acid and acetic anhydride in a temperature range from −50° C. to 0° C. or from the corresponding derivatives of formula HOOC-y-$Z_2$ (IVc) wherein $Z_2$ is as above defined, by reaction with a nitrate source as above described. Alternatively the reaction with $AgNO_3$ can be performed under microwave irradiation in solvents such acetonitrile or THF at temperatures in the range between about 100-180° C. for time range about 1-60 min.

The compounds of formula (IVb) are commercially available.

The compounds of formula (IVc) are commercially available or can be obtained as known in the literature.

The compounds of formula (IVa) wherein $W_1$ is O—$R_a$, y, Q are as above defined, can be obtained from the corresponding acids of formula (IVa) wherein $W_1$ is OH as known in the literature.

The compounds of formula (Ia) wherein W=Cl or O—$R_a$, $X_1$ is selected from (a2'), (a4'), (b2'), (b4'), (c2'), (e2'), (f1'), (g2'), (h1'), (i1'), (l2'), (m2'), (n2'), (o2'), (p2'), (q2'), (r2'), (s2'), (t2'), (u2'), (v2'), wherein $R^1$ is selected from A1), A2'), A3'), A4'), $R^{1a}$ is selected from A5) or A6), $R^{ea}$ is selected from B5) or B6) and $R^{2'}$ is selected from B1), B2'), B3'), B4'), and wherein Y, Y' and Q are as above defined and T' and T" are C(O), can be obtained from the corresponding acids (Ia) wherein W is —OH as known in the literature.

1b) The compounds of formula (Ia) wherein W is —OH, $X_1$ is the radical selected from (a2'), (a4'), (b2'), (b4') (c2'), (e2'), (f1'), (g2'), (h1'), (i1'), (l2'), (m2'), (n2'), (o2'), (p2'), (q2'), (r2'), (s2'), (t2'), (u2'), (v2'), wherein $R^{1'}$ is selected from A1), A2'), A3'), A4'), $R^{1a}$ is selected from A5) or A6), $R^{2a}$ is selected from B5) or B6) and $R^{2'}$ is selected from B1), B2'), B3'), B4'), Y and Y' are as above defined, T' and T" are C(O)—X", wherein X" is —O— or —S— can be obtained 1b-i) by reacting a compound of formula (IIIa)

$$P^2\text{—}X_2 \tag{IIIa}$$

wherein $P^2$ and $X_2$ are as defined above, with a compound of formula (IVd)

$$R_a\text{—O—C(O)—X"-}y\text{-Q} \tag{IVd}$$

wherein R, X" and Q are as above defined, y is the radical Y when $X_2$ is selected from (a2'), (b2'), (c2'), (e2'), (f1'), (g2'), (h1'), (i1'), (l2'), (m2'), (n2'), (o2'), (p2'), (q2'), (r2'), (s2'), (t2'), (u2'), (v2'), and y is the radical Y' when $X_2$ is selected from (a4') or (b4'), wherein Y and Y' are as above defined, and 1b-ii) when Q is $Z_2$, by converting the compound obtained in the step 1b-i) into nitro derivative by reaction with a nitrate source as above described and 1b-iii) optionally deprotecting the compounds obtained in step 1b-i) or 1b-ii) as above described.

The reaction of a compound of formula (IIIc) wherein $P^2$ and $X_2$ are as above defined, with a compound of formula (IVd) wherein $R_a$, X", y and Q are as above defined, may be carried out as described in 1-i-2)

The compounds of formula (IVd) wherein $R_a$, X", y, Q are as above defined, can be obtained from the compounds of formula HX"-y-Q (IVe) wherein X", y, Q are as above defined, as known in literature.

The compound of formula (IVe) are commercially available or are known in literature.

The compounds of formula (Ia) wherein W is —Cl or O—R, $X_1$ is selected from (a2'), (a4'), (b2'), (b4'), (c2'), (e2'), (f1'), (g2'), (h1'), (i1'), (l2'), (m2'), (n2'), (o2'), (p2'), (q2'), (r2'), (s2'), (t2'), (u2'), (v2'), wherein $R^{1'}$ is selected from A1), A2'), A3'), A4'), $R^{1a}$ is selected from A5) or A6), $R^{ea}$ is selected from B5) or B6) and $R^{2'}$ is selected from B1), B2'), B3'), B4'), Y, Y' and Q are as above defined, T' and T" are C(O)—X" wherein X" is O or S, can be obtained from the corresponding acids (Ia) wherein W is —OH as known in the literature.

1c) The compounds of formula (Ia) wherein W is —OH and $X_1$ is a radical selected from (a8') or (b8'), wherein $R^{1a}$ is selected from A5) or A6), $R^{2a}$ is selected from B5) or B6), Q is as above defined, T' and T" are C(O), Y and Y' are the same and are as above defined, can be obtained 1c-i) by reacting a compound of formula (IIIb),

  (IIIb)

wherein $P^2$ is above defined, $X_3$ is the radical of formula
(a8") —C(O)—CH($R^{1a}$—H)—NH$_2$
(b8") —C(O)—CH$_2$—CH($R^{2a}$—H)—NH$_2$
wherein $R^{1a}$ is selected from A5) or A6), $R^{2a}$ is selected from B5) or B6), with a compound of formula (IVa)

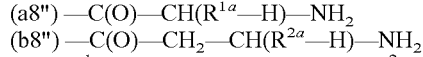  (IVa)

wherein $W_1$ and Q are as above defined, wherein y is the radical Y or Y', wherein Y and Y' are as above defined, and 1c-ii) when Q is $Z_2$, by converting the compound obtained in the step 1c-i) into nitro derivative by reaction with a nitrate source as above described and 1c-iii) optionally deprotecting the compounds obtained in step 1c-i) or 1c-ii) as above described.

The reaction of a compound of formula (IIIb) wherein $P^2$ and $X_3$ are as above defined, with a compound of formula (IVa) wherein $W_1$ is OH, y and Q are as above defined, may be carried out as described in 1a-i) using a ratio (IIIb)/(IVa) 1:2.

The reaction of a compound of formula (IIIb) wherein $P^2$ and $X_3$ are as above defined, with a compound of formula (IVa) wherein $W_1$ is $OR_a$, y and Q are as above defined, may be carried out as described in 1-i-2) using a ratio (IIIb)/(IVa) 1:2.

The compounds of formula (IIIb) are commercially available or can be obtained as known in the literature.

The compounds of formula (Ia) wherein W is —Cl or O—$R_a$, $X_1$ is the radical selected from (a8') or (b8') wherein $R^{1a}$ is selected from A5) or A6), $R^{2a}$ is selected from 35) or 36) and wherein Y, Y' and Q are as above defined and T' and T" are C(O), can be obtained from the corresponding acids (Ia) wherein W is —OH as known in the literature.

1d) The compounds of formula (Ia) wherein W is —OH, $X_1$ is the radical selected from (a8') or (b8'), wherein $R^{1a}$ is selected from A5) or A6), $R^{2a}$ is selected from B5) or B6), Q, Y and Y' are as above defined, T' is C(O) or C(O)—X" wherein X" is as above defined, T" is C(O), can be obtained 1d-i) by reacting a compound of formula (Ib)

  (Ib)

wherein $P^2$ is as above defined, $X_3$', is the radical of formula
(a8''') —C(O)—CH($R^{1a}$—H)—NH-(T'-Y-Q))
(b8''') —C(O)—CH$_2$—CH($R^{2a}$—H)—NH-(T'-Y-Q)
wherein $R^{1a}$ is selected from A5) or A6), $R^{2a}$ is selected from 35) or B6), with a compound of formula (IVa)

  (IVa)

wherein $W_1$ and Q are as above defined, wherein y is the radical Y', wherein Y' is as above defined, and 1d-ii) when Q is $Z_2$, by converting the compound obtained in the step 1d-i) into nitro derivative by reaction with a nitrate source as above described and 1d-iii) optionally deprotecting the compounds obtained in step 1d-i) or 1d-ii) as above described.

The reaction of a compound of formula (Ib) wherein $P^2$ and $X_3$', are as above defined, with a compound of formula (IVa) wherein $W_1$ is OH, y and Q are as above defined, may be carried out as described in 1a-i).

The reaction of a compound of formula (Ib) wherein $P^2$ and $X_3$', are as above defined, with a compound of formula (IVa) wherein $W_1$ is $OR_a$, y and Q are as above defined may be carried out as described in 1-i-2).

The compounds of formula (Ib) wherein T' is C(O), $P^2$ and $X_3$', are as above defined, are obtained as described in 1a).

The compounds of formula (Ib) wherein T' is C(O)—X", $P^2$ and $X_3$', are as above defined, are obtained as described in 1b).

The compounds of formula (Ia) wherein W is —Cl or O—$R_a$', $X_1$ is the radical selected from (a8') or (b8') wherein $R^{1a}$ is selected from A5) or A6), $R^{2a}$ is selected from B5) or B6) and wherein Q, Y and Y' are as above defined, T' is C(O) or C(O)—X" wherein X" is as above defined, T" is C(O), can be obtained from the corresponding acids (Ia) wherein W is —OH as known in literature.

1e) The compounds of formula (Ia) wherein W is —OH, $X_1$ is the radical selected from (a8') or (b8'), wherein $R^{1a}$ is selected from A5) or A6), $R^{2a}$ is selected from B5) or B6), Q is as above defined, Y and Y' are the same and are as above defined, T' and T" are C(O)—X"— wherein X" is as above defined, can be obtained 1e-i) by reacting a compound of formula (IIIb)

  (IIIb)

wherein $P^2$ and $X_3$ are as above defined, with a compound of formula (IVd)

  (IVd)

wherein $R_a$ and Q are as above defined, wherein y is the radical Y', wherein Y' is as above defined, and 1e-ii) when Q is $Z_2$, by converting the compound obtained in the step 1e-i) into nitro derivative by reaction with a nitrate source as above described and 1e-iii) optionally deprotecting the compounds obtained in step 1e-i) or 1e-ii) as above described.

The reaction of a compound of formula (IIIb) wherein $P^2$ and $X_3$ are as above defined, with a compound of formula (IVd) wherein $R_a$, y and Q are as above defined, may be carried out as described in 1-i-2) using a ratio (IIIb)/(IVd) 1:2.

The compounds of formula (Ia) wherein W is —Cl or O—R, $X_1$ is the radical selected from (a8') or (b8') wherein $R^{1a}$ is selected from A5) or A6), $R^{2a}$ is selected from B5) or B6) and wherein Y and Y', Q is as above defined and T' and T" are C(O)—X"— wherein X" is as above defined, can be obtained from the corresponding acids (Ia) wherein W is —OH as known in literature.

1f) The compounds of formula (Ia) wherein W is —OH, $X_1$ is selected from (a8') or (b8'), wherein $R^{1a}$ is selected from A5) or A6), $R^{2a}$ is selected from B5) or B6), Q, Y and Y' are as above defined, T' is C(O) or C(O)—X" wherein X" is as above defined, T" is C(O)—X", can be obtained 1f-i) by reacting a compound of formula (Ib)

  (Ib)

wherein $X_3$' and $P^2$ are as above defined, with a compound of formula (IVd)

  (IVd)

wherein $W_1$ and Q are as above defined, y is the radical Y', wherein Y' is as above defined, and 1f-ii) when Q is $Z_2$, by converting the compound obtained in the step 1f-i) into nitro derivative by reaction with a nitrate source as above described and 1f-iii) optionally deprotecting the compounds obtained in step 1f-i) or 1f-ii) as above described.

The reaction of a compound of formula (Ib) wherein $P^2$ and $X_3$, are as above defined, with a compound of formula (IVd) wherein $W_1$ is OH, y and Q are as above defined, may be carried out as described in 1a-i).

The reaction of a compound of formula (Ib) wherein $P^2$ and $X_3$, are as above defined, with a compound of formula (IVd) wherein $W_1$ is $OR_a$, y and Q are as above defined may be carried out as described in 1-i-2).

The compounds of formula (Ib) wherein T' is C(O), $P^2$ and $X_3$, are as above defined, are obtained as described in 1a).

The compounds of formula (Ib) wherein T' is C(O)—X", $P^2$ and $X_3$, are as above defined, are obtained as described in 1b).

The compounds of formula (Ia) wherein W is —Cl or O—$R_a$', $X_1$ is a radical selected from (a8') or (b8') wherein $R^{1a}$ is A5) or A6), $R^{2a}$ is B5) or B6) and wherein Q, Y and Y' are as above defined, T' is C(O) or C(O)—X" and T" is C(O)—X, wherein X" is as above defined, can be obtained from the corresponding acids (Ia) wherein W is —OH as known in literature.

1g) The compounds of formula (Ia) wherein W is —OH, $X_1$ is a radical is selected from (a8') or (b8'), wherein $R^{1a}$ is selected from A5), A6), $R^{2a}$ is selected from B5), B6), Q, Y and Y' are as above defined, T' is C(O) or C(O)—X" wherein X" is as above defined, T" is C(O)—NR' wherein R' is above defined, can be obtained 1g-i) by reacting a compound of formula (Ib)

wherein $P^2$ and $X_3$, are as above defined, with a compound of formula

wherein $R_a$, R' and Q are as above defined, y is the radical Y', wherein Y' is as above defined, and 1g-ii) when Q is $Z_2$, by converting the compound obtained in the step 1g-i) into nitro derivative by reaction with a nitrate source as above described and 1g-iii) optionally deprotecting the compounds obtained in step 1g-i) or 1g-ii) as above described.

The reaction of a compound of formula (Ib) wherein $P^2$ and $X_3$, are as above defined, with a compound of formula (IVf) wherein $R_a$, R', y, Q are as above defined, may be carried out as described in 1-i-2).

The compounds of formula (Ib) wherein T' is C(O), wherein $P^2$ and $X_3$, are as above defined, are obtained as described in 1a-i), 1a-ii).

The compounds of formula (Ib) wherein T' is C(O)—X", wherein $P^2$ and $X_3$' are as above defined, are obtained as described in 1b-i), 1b-ii).

The compounds of formula (IVf) wherein R', y and Q are as above defined, can be obtained from the compounds of formula HR'N-y-Q (IVg) by reaction with a chloroformate as known in the literature.

The compounds of formula (IVg) wherein y is as above defined and Q is $Z_2$ is commercially available, the compounds of formula (IVg) wherein y is as above defined and Q is —$ONO_2$ may be obtained from the compound of formula

wherein $P^3$ is as above defined by deprotection of amino group as known in literature. The compounds of formula (IVh) wherein $P^3$, y are as above defined may be obtained from the alcohol

by reacting with tetraalkylammonium nitrate as already described for analogous compounds. The compounds of formula (IVi) are commercially available or known in literature. Alternatively the compounds of formula (IVh) wherein $P^3$, y are as above defined may be obtained from the corresponding compounds of formula

wherein $P^3$, y, $Z_2$ are as above defined, by reaction with a nitrate source as above described.

The compounds of formula (Ia) wherein W is —Cl or O—$R_a$, $X_1$ is a radical selected from (a8') or (b8') wherein R selected from A5) or A6), $R^{2a}$ is selected from B5) or B6) and wherein Y, Y' and Q are as above defined and T' is C(O) or C(O)—X", T" is C(O)—NR'—, wherein X" and R' are as above defined, can be obtained from the corresponding acids (Ia) wherein W is —OH as known in literature.

1h) The compounds of formula (Ia) wherein W is —OH, $X_1$ is a radical selected from (a8') or (b8'), wherein $R^{1a}$ is selected from A7), $R^{2a}$ is selected from B7), Q, Y and Y' are as above defined, T' is C(O) or C(O)—X", T" is X" wherein X" is above defined, can be obtained 1 h-i) by reacting a compound of formula (Ie),

wherein $P^2$ is defined above, $X_5$ is the radical of formula
(a8") —C(O)—CH($R^{1a}$—OH)—NH-(T'-Y-Q)
(b8") —C(O)—$CH_2$—CH($R^{2a}$—OH)—NH-(T'-Y-Q)
wherein $R^{1a}$ is selected from A7), $R^{2a}$ is selected from B7), with a compound of formula (IVe)

wherein X" and Q are as above defined, y is the radical Y', wherein Y' is as above defined, and 1 h-ii) when Q is $Z_2$, by converting the compound obtained in the step 1h-i) into nitro derivative by reaction with a nitrate source as above described and 1h-iii) optionally deprotecting the compounds obtained in step 1h-i) or 1 h-ii) as above described.

The reaction of a compound of formula (Ie) wherein $P^2$ and $X_5$ are as above defined, with a compound of formula (IVe) wherein y, X" and Q are as above defined, may be carried out as described in 1-i-1).

The compounds of formula (Ie) wherein T' is C(O), wherein $P^2$ and $X_5$ are as above defined, are obtained as described in 1a-i), 1a-ii).

The compounds of formula (Ie) wherein T' is C(O)—X", wherein $P^2$ and $X_5$ are as above defined, are obtained as described in 1b-i), 1b-ii).

The compounds of formula (Ia) wherein W is —Cl or O—$R_a$, $X_1$ is a radical selected from (a8') or (b8') wherein $R^{1a}$ is selected from A7), $R^{2a}$ is selected from B7) and wherein Y, Y' and Q are as above defined, T' is C(O) or C(O)—X", and T" is X" wherein X" is as above defined, can be obtained from the corresponding acids (Ia) wherein W is —OH as known in literature.

1i) The compounds of formula (Ia) wherein W is —OH, $X_1$ is a radical selected from (a8') or (b8'), wherein $R^{1a}$ is selected from A7), $R^{2a}$ is selected from B7), Q, Y and Y' are as above defined, T' is C(O) or C(O)—X" wherein X" is as above defined, T" is —NR' wherein R' is above defined, can be obtained 1i-i) by reacting a compound of formula (Ie),

wherein is $P^2$ and $X_5$ are defined above, with a compound of formula (IVg)

HR'N-y-Q    (IVg)

wherein R' and Q are as above defined, y is the radical Y', wherein Y' is as above defined, and 1i-ii) when Q is $Z_2$, by converting the compound obtained in the step 1l-i) into nitro derivative by reaction with a nitrate source such above described and 1i-iii) optionally deprotecting the compounds obtained in step 1i-i) or 1i-ii) as above described.

The reaction of a compound of formula (Ie) wherein $P^2$ and $X_5$ are as above defined, with a compound of formula (IVg) wherein R', y and Q are as above defined, may be carried out as described in 1a-i).

The compounds of formula (Ia) wherein W is —Cl or O—$R_a$, $X_1$ is the radical selected from (a8') or (b8') wherein R selected from A7), $R^{2a}$ is selected from B7) and wherein Y, Y' and Q are as above defined, T' is C(O) or C(O)—X" wherein X" is as above defined, and T" is —NR' wherein R' is as above defined can be obtained from the corresponding acids (Ia) wherein W is —OH as known in literature 1l) The compounds of formula (Ia) wherein W is —OH, $X_1$ is a radical selected from (a8') or (b8'), wherein $R^{1a}$ is selected from A7), $R^{2a}$ is selected from B7), Q, Y and Y' are as above defined, T' is C(O) or C(O)—X" wherein X" is as above defined, T" is —O—CH(R')—O—C(O)—, wherein R' is as above defined, can be obtained 1l-i) by reacting a compound of formula (Ie), $P^2$—$X_5$    (Ie)

wherein is $P^2$ and $X_5$ are defined above, with a compound of formula (IVm)

Hal-CH(R')—O—(O)C-y-Q    (IVm)

wherein R' and Q are as above defined, Hal is an halogen atom, y is the radical Y', wherein Y' is as above defined, and 1l-ii) when Q is $Z_2$, by converting the compound obtained in the step 1l-i) into nitro derivative by reaction with a nitrate source such above described and 1l-iii) optionally deprotecting the compounds obtained in step 1l-i) or 1l-ii) as above described.

The reaction of a compound of formula (Ie) wherein $P^5$ and $X_5$ are as above defined, with a compound of formula (IVm) wherein y, Q, R' are as above defined may be carried out in the presence of a inorganic or organic base in an aprotic polar/non-polar solvent such as DMF, THF or CH$_2$Cl$_2$ at temperatures range between 0° to 100° C. or in a double phase system H$_2$O/Et$_2$O at temperatures range between 20° to 40° C.

The compounds of formula (IVm) wherein y, Q, R' are as above defined, Hal is an halogen atom may be obtained by reacting a compound R'—CH$_2$—CHO, commercially available, with a compound of formula Hal-(O)C-y-Q    (IVn), wherein y and Q are as above defined, Hal is a chlorine atom and ZnCl$_2$ as known in literature.

The compounds of formula (IVn) may be obtained as known in literature.

The compounds of formula (Ia) wherein W is —Cl or O—$R_a$, $X_1$, is a radical selected from (a8') or (b8') wherein $R^{1a}$ is selected from A7), $R^{2a}$ is selected from B7) and wherein Y, Y', and Q are as above defined, T' is C(O) or C(O)—X" wherein X" is as above defined, and T" is —O—CH(R')—O—C(O)— wherein R' is as above defined can be obtained from the corresponding acids (Ia) wherein W is —OH as known in literature.

1m) The compounds of formula (Ia) wherein W is —OH, $X_1$ is a radical selected from (a8') or (b8'), wherein $R^{1a}$ is selected from A7), $R^{2a}$ is B7), Q, Y and Y' are as above defined, T' is C(O) or C(O)—X" wherein X" is as above defined, T" is —O—CH(R')—O—C(O)O—, wherein R' is as above defined, can be obtained 1m-i) by reacting a compound of formula (Ie), $P^2$—$X_5$    (Ie)

wherein is $P^2$ and $X_5$ are defined above, with a compound of formula (IVo)

Hal-OH(R')—O—(O)C—O-y-Q    (IVo)

wherein R' and Q are as above defined, y is the radical Y', wherein Y' is as above defined, Hal is an halogen atom, and 1l-ii) when Q is $Z_2$, by converting the compound obtained in the step 1l-i) into nitro derivative by reaction with a nitrate source such above described and 1l-iii) optionally deprotecting the compounds obtained in step 1l-i) or 1l-ii) as above described.

The reaction of a compound of formula (Ie) wherein $P^2$ and $X_5$ are as above defined, with a compound of formula (IVo) wherein y, R', Q, Hal are as above defined may be carried out as described in 1l-i).

The compounds of formula (IVo) wherein y, R', Q are as above defined, may be obtained by reacting the compounds of formula Hal-(R')CH—OC(O)Hal, wherein Hal is as above defined, commercially available, with a compound of formula HO-y-Q    (IVe)

wherein y, Q are as above defined, in the presence of a inorganic or organic base in an aprotic polar or in an aprotic non-polar solvent such as DMF, THF or CH$_2$Cl$_2$ at temperatures range between 0° to 65° C.

The compounds of formula (Ia) wherein W is —Cl or O—$R_a$, $X_1$ is a radical selected from (a8') or (b8') wherein $R^{1a}$ selected from A7), $R^{2a}$ selected from B7) and wherein Y, Y' and Q are as above defined, T' is C(O) or C(O)—X" wherein X" is as above defined, and T" is —O—CH(R')—O—C(O)O—, may be obtained from the corresponding acids (Ia) wherein W is —OH as known in literature.

1n) The compounds of formula (Ia) wherein W is —OH, $X_2$ is a radical selected from (a4') or (b4'), wherein $R^{1a}$ is selected from A7), $R^{2a}$ is selected from B7), Y', Q and $R^{4a'}$ are as above defined and T" is X" wherein X" is as above defined, can be obtained 1n-i) by reacting a compound of formula (IIIc)

$P^2$—$X_{5'}$    (IIIc)

wherein $P^2$ is defined above, $X_{5'}$ is
(a4") —C(O)—CH($R^{1a}$—OH)—NHR$^{4a'}$
(b4") —C(O)—CH$_2$—CH($R^{2a}$—OH)—NHR$^{4a'}$
wherein $R^{1a}$ is selected from A7), $R^{2a}$ is selected from B7) and $P^3$ is as above defined,
with a compound of formula (IVe)

HX"-y-Q    (IVe)

wherein X" and Q are as above defined, y is the radical Y', wherein Y' is as above defined, and 1n-ii) when Q is $Z_2$, by converting the compound obtained in the step 1n-i) into nitro derivative by reaction with a nitrate source as above described and 1n-iii) optionally deprotecting the compounds obtained in step 1n-i) or 1n-ii) as above described.

The reaction of a compound of formula (IIIc) wherein $X_y$ and $P^2$ are as above defined, with a compound of formula (IVe) wherein X", y, Q are as above defined may be carried out as described in 1-i-1).

The compounds of formula (IIIc) wherein $X_{5'}$ and $P^2$ are as above defined, are commercially available or can be obtained as known in the literature.

The compounds of formula (Ia) wherein W is —Cl or O—$R_a$, $X_1$ is a radical selected from (a4') or (b4'), wherein $R^{1a}$ is selected from A7), $R^{2a}$ is selected from B7), Y' and Q are as above defined, T" is X", wherein X" is as above defined, can be obtained from the corresponding acids (Ia) wherein W is —OH as known in literature.

The compounds of formula (Ia) wherein W is —OH, $X_1$ is a radical selected from (a4') or (b4'), wherein $R^{1a}$ is selected from A7), $R^{2a}$ is selected from B7), Y', Q and $R^{4a'}$ are as above defined and T" is —NR' wherein R' is as above defined, can be obtained 1o-i) by reacting a compound of formula (IIIc)

wherein $P^2$ and $X_{y'}$ are as above defined, with a compound of formula (IVg)

wherein R' and Q are as above defined, y is the radical Y', and
1o-ii) when Q is $Z_2$, by converting the compound obtained in the step 1o-i) into nitro derivative by reaction with a nitrate source as above described and
1o-iii) optionally deprotecting the compounds obtained in step 1o-i) or 1o-ii) as above described.

The reaction of a compound of formula (IIIc) wherein $X_{5'}$ and $P^2$ are as above defined, with a compound of formula (IVg) wherein R', y and Q are as above defined may be carried out as described in 1a-i).

The compounds of formula (Ia) wherein W is —Cl or —$OR_a$, $X_1$ is a radical selected from (a4') or (b4'), wherein $R^{1a}$ is selected from A7), $R^{2a}$ is selected from B7) and wherein Y', Q are as above defined and T" is —NR' wherein R' is as above defined, can be obtained may be obtained from the corresponding acids (Ia) wherein W=—OH as known in literature.

1p) The compounds of formula (Ia) wherein W is —OH, $X_1$ is a radical selected from (a4') or (b4'), wherein $R^{1a}$ is selected from A7), $R^{2a}$ is selected from B7), Y', Q and $R^{4a'}$ are as above defined and T" is —O—CH(R')—O—C(O), wherein R' is as above defined, can be obtained 1p-i) by reacting a compound of formula (IIIc)

wherein $P^2$ and $X_{y'}$ are as above defined, with a compound of formula (IVm)

wherein R' and Q are as above defined, y is the radical Y', wherein Y' is as above defined, Hal is an halogen atom and
1p-ii) when Q is $Z_2$, by converting the compound obtained in the step 1p-i) into nitro derivative by reaction with a nitrate source as above described and
1p-iii) optionally deprotecting the compounds obtained in step 1p-i) or 1p-ii) as above described.

The reaction of a compound of formula (IIIc) wherein $P^2$ and $X_{y'}$ are as above defined, with a compound of formula (IVm) wherein R', y, Q, Hal are as above defined, may be carried out as described in 1l-1).

The compounds of formula (Ia) wherein W is —$C_1$ or $OR_a$, $X_1$ is a radical selected from (a4') or (b4'), wherein $R^{1a}$ is selected from A7), $R^{2a}$ is selected from B7) and wherein Y and Q are as above defined and T" is the group —O—CH(R')—O—C(O), wherein R' is as above defined, can be obtained from the corresponding acids (Ia) wherein W=—OH as known in literature.

The compounds of formula (Ia) wherein W is —OH, $X_1$ is a radical selected from (a4') or (b4'), wherein $R^{1a}$ is selected from A7), $R^{2a}$ is selected from B7), Y', Q and $R^{4a'}$ are as above defined and T" is —O—CH($R^1$)—O—C(O)—O—, wherein R' is as above defined, can be obtained 1q-i) by reacting a compound of formula (IIIc)

wherein $P^2$ and $X_{y'}$ are as above defined, with a compound of formula (IVo)

wherein R' and Q are as above defined, y is the radical Y', wherein Y' is as above defined, Hal is an halogen atom and
1q-ii) when Q is $Z_2$, by converting the compound obtained in the step 1q-i) into nitro derivative by reaction with a nitrate source as above described and
1q-iii) optionally deprotecting the compounds obtained in step 1q-i) or 1q-ii) as above described.

The reaction of a compound of formula (IIIc) wherein $P^2$ and $X_{y'}$ are as above defined, with a compound of formula (IVo) wherein R', y, Q, Hal are as above defined, may be carried out as described in 1l-1).

The compounds of formula (Ia) wherein W is —Cl or $OR_a$, $X_1$ is a radical selected from (a4') or (b4'), wherein $R^{1a}$ is selected from A7), $R^{2a}$ is selected from B7) and wherein Y, Q, are as above defined and T" is the group —O—CH(R')—O—C(O)—O—, wherein R' is as above defined, can be obtained may be obtained from the corresponding acids (Ia) wherein W=—OH as known in literature.

2) The compound of general formula (I) as above defined wherein a is equal to 1, the radical $R_x$ is the radical selected from (a2), (a4), (a8), (b2), (b4), (b8), (c2), (e2), (f1), (g2), (h1), (i1), (l2), (m2), (n2), (o2), (p2), (q2), (r2), (s2), (t2), (u2), (v2), Z is —CH(R')—O— wherein R' is selected from H or straight or branched $C_1$-$C_4$ alkyl, can be obtained:
2-i) by reacting a compound of formula (IIa)

wherein R is as above defined with a compound of formula (If)

wherein Hal is an halogen atom, R' and $X_1$ are as above defined and
2-ii) when Q is $Z_2$, by converting the compound obtained in the step 2-i) into nitro derivative by reaction with a nitrate source as above described and
2-iii) optionally deprotecting the compounds obtained in step 2-i) or 2-ii) as above described.

The reaction of a compound of formula (If) wherein) $X_1$ and R' are as above defined, with a compound of formula (IIa) wherein R is as above defined, may be carried out as described in 1l-i).

The compounds of formula (If) are obtained by reacting a compound R'—CHO, wherein R' is as above defined with compounds of formula (Ia)

wherein W is a chlorine atom, $X_1$ is as above defined, and $ZnCl_2$ as known in literature.

3) The compound of general formula (I) as above defined wherein a is equal to 1, the radical $R_x$ is selected from (a1), (a3), (a7), (b1), (b3), (b7), (c1), (e1), (f2), (g1), (h2), (i2), (l1), (m1), (n1), (o1), (p1), (q1), (r1), (s1), (t1), (u1), (v1), Z is C(O), can be obtained 3-i) by reacting a compound of formula $$R—C(O)—O—R_a \quad \text{(IIb)}$$

wherein R and $R_a$ are as above defined, with a compound of formula (Ig)

$$H—X_2 \quad \text{(Ig)}$$

wherein $X_2$ is a radical having the following meanings:
- (a1') —HN—CH($R^{1'}$)—C(O)-(T-Y-Q)
- (a3') —HN—CH($R^{1a}$-T"-Y'-Q)-COOR$^{3a'}$
- (a7') —HN—OH($R^{1a}$-T"-Y'-Q)-C(O)-(T-Y-Q)
- (b1') —HN—CH($R^{2'}$)—CH$_2$C(O)-(T-Y-Q)
- (b3') —HN—CH($R^{2a}$-T"-Y'-Q)-CH$_2$COOR$^{3a'}$
- (b7') —HN—CH($R^{2a}$-T"-Y'-Q)-CH$_2$—C(O)-(T-Y-Q)

wherein $R^{1'}$, $R^{1a}$, $R^{2'}$, $R^{2a}$ are as above defined
$R^{3a'}$ is selected from $P^2$, —OR$^{5a}$ or

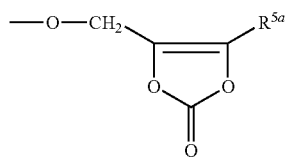

wherein $R^{5a}$ is as above defined;

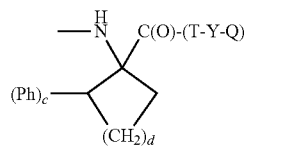 (e1')

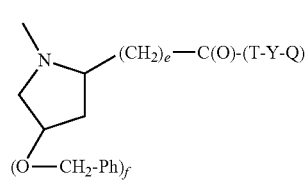 (f2')

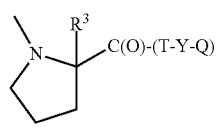 (g1')

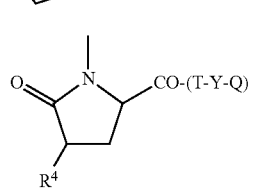 (h2')

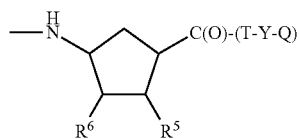 (i2')

-continued

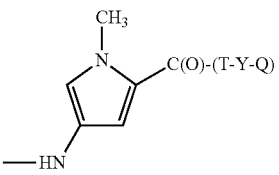 (l1')

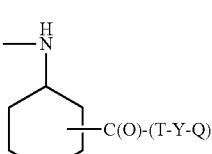 (m1')

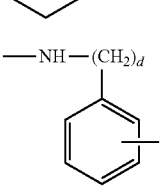 (n1')

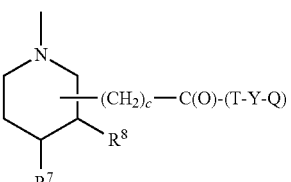 (o1')

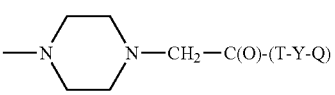 (p1')

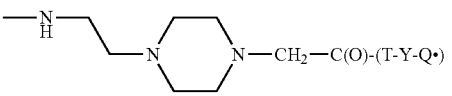 (q1')

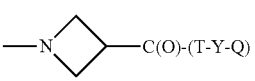 (r1')

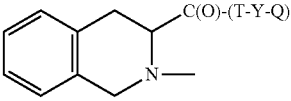 (s1')

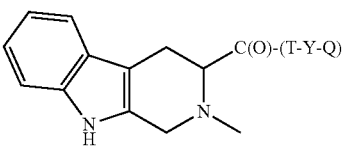 (t1')

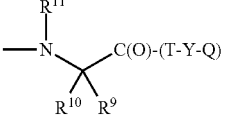 (u1')

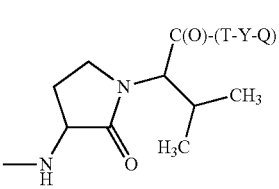 (v1')

wherein T, T", Y and Y' are as above defined, 3-ii) when Q is $Z_2$, by converting the compound obtained in the step 3-i) into nitro derivative by reaction with a nitrate source such above described and 3-iii) optionally deprotecting the compounds obtained in step 3-i) or 3-ii) as above described.

The reaction of a compound of formula (IIb) wherein R and $R_a$ are as above defined, with a compound of formula (Ig) wherein X, is as above defined, may be carried out as described in 1-i-2).

The compounds of formula $R-C(O)-O-R_a$ (IIb) wherein R and $R_a$ are as above defined, are obtained from the compounds R—H (IIa) by reaction with the compounds of formula $Cl-C(O)-O-R_a$ wherein $R_a$ is as above defined, as known in literature.

3a) The compounds of formula (Ig) wherein $X_2$ is selected from (a1'), (a3'), (b1'), (b3'), (c1'), (e1'), (f2'), (g1'), (h2'), (i2'), (l1'), (m1'), (n1'), (o1'), (p1'), (q1'), (r1'), (s1'), (t1'), (u1'), (v1'), wherein $R^{1'}$ is selected from A1), A2'), A3'), A4'), $R^{1a}$ is selected from A7), $R^{2a}$ is selected from B7) and $R^{2'}$ is selected from B1), B2'), B3'), B4'), Y and Y' are as above defined, T and T" are X" wherein X" is as above defined may be obtained 3a-i) by reacting a compound of formula (IIIe),

  (IIIe)

wherein $P^3$ is as above defined, $X_6$ is a radical having the following meanings:

(a1") —HN—CH($R^{1'}$)—C(O)—OH (a3") —HN—CH($R^{1a}$—OH)—COOR$^{1a'}$ (b1") —HN—CH($R^{2'}$)—CH$_2$O(O)—OH (b3") —HN—OH($R^{2a}$—OH)—CH$_2$COOR$^{3a'}$ wherein $R^{1'}$ is selected from A1), A2'), A3'), A4'), $R^{1a}$ is selected from A7), $R^{2a}$ is selected from B7) and $R^{2'}$ is selected from B1), B2'), B3'), B4'), and $R^{3'}$ is defined above (c1") —HN—(CH$_2$)$_b$—C(O)—OH;

 (e1")

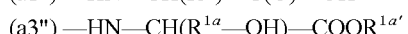 (f2")

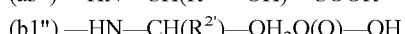 (g1")

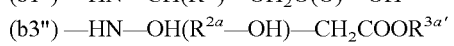 (h2")

 (i2")

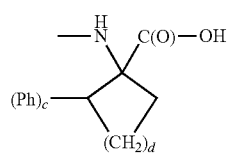 (l1")

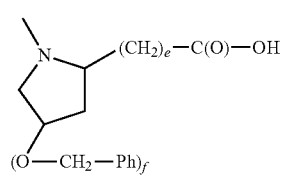 (m1")

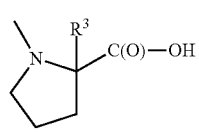 (n1")

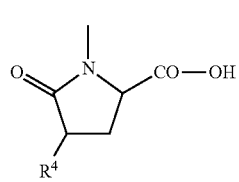 (o1")

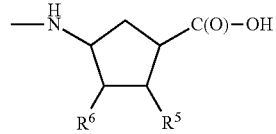 (p1")

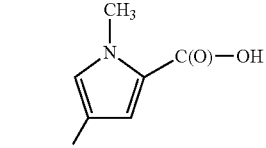 (q1")

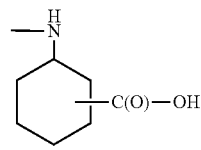 (r1")

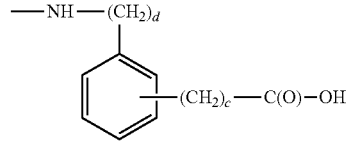 (s1")

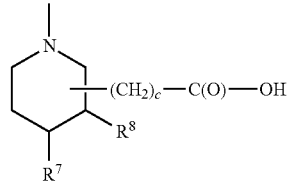 (t1")

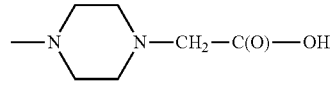 (u1")

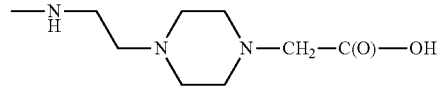
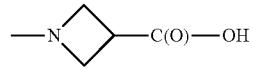
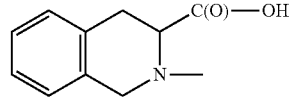
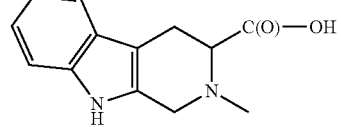
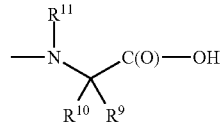

-continued

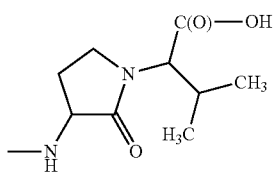
(v1″)

with a compound of formula (IVe)

HX″-y-Q     (IVe)

wherein Q and X″ are as above defined y is the radical Y when X$_6$ is selected from (a1′), (b1′), (c1′), (e1′), (f2′), (g1′), (h2′), (i2′), (l1′), (m1′), (n1′), (o1′), (p1′), (q1′), (r1′), (s1′), (t1′), (u1′) and (v1′), y is the radical Y′ when X$_6$ is selected from (a3′) and (b3′), wherein Y and Y′ are as defined above, and 3a-ii) when Q is Z$_2$, by converting the compound obtained in the step 3a-i) into nitro derivative by reaction with a nitrate source as above described and 3a-iii) optionally deprotecting the compounds obtained in step 3a-i) or 3a-ii) as above described.

The reaction of a compound of formula (IIIe) wherein P$^3$ and X$_6$ are as above defined, with a compound of formula (IVe), wherein y, Q and X″ are as above defined, may be carried out as described in 1-i-1).

The compounds of formula (IIIe) are commercially available or can be obtained as known in the literature.

3b) The compounds of formula (Ig) wherein X$_2$ is selected from (a1′), (a3′), (b1′), (b3′), (c1′), (e1′), (f2′), (g1′), (h2′), (i2′), (l1′), (m1′), (n1′), (o1′), (p1′), (q1′), (r1′), (S1′), (t1′), (u1′), (v1′), wherein is selected from A1), A2′), A3′), A4′), R$^{1a}$ is selected from A7), R$^{2a}$ is selected from B7) and R$^{2′}$ is selected from B1), B2′), B3′), B4′), and R$^{3a′}$, Y and Y′ are as above defined, T and T″ are —NR′ wherein R′ is as above defined may be obtained 3b-i) by reacting a compound of formula (IIIe), P$^3$—X$_6$     (IIIe)

wherein P$^3$ and X$_6$ are as above defined, with a compound of formula

HR′N-y-Q     (IVg)

wherein R′ and Q are as above defined, y is the radical Y when X$_6$ is selected from (a1′), (b1′), (c1′), (e1′), (f2′), (g1′), (h2′), (i2′), (l1′), (m1′), (n1′), (o1′), (p1′), (q1′), (r1′), (s1′), (t1′), (u1′) and (v1′), y is the radical Y′ when X$_6$ is selected from (a3′) and (b3′), wherein Y and Y′ are as defined above, and 3b-ii) when Q is Z$_2$, by converting the compound obtained in the step 3b-i) into nitro derivative by reaction with a nitrate source as above described and 3b-iii) optionally deprotecting the compounds obtained in step 3b-i) or 3b-ii) as above described.

The reaction of a compound of formula (IIIe) wherein P$^3$ and X$_6$ are as above defined, with a compound of formula (IVg) wherein R′, y, Q are as above defined, may be carried out 1a-i).

3c) The compounds of formula (Ig) wherein X$_2$ is selected from (a1′), (a3′), (b1′), (b3′), (c1′), (e1′), (f2′), (g1′), (h2′), (i2′), (l1′), (m1′), (n1′), (o1′), (p1′), (q1′), (r1′), (s1′), (t1′), (u1′), (v1′), wherein R$^{1′}$ is selected from A1), A2′), A3′), A4′), R$^{1a}$ is selected from A7), R$^{2a}$ is selected from B7) and R$^{2′}$ is selected from B1), B2′), B3′), B4′), and R$^{3a′}$, Y and Y′ are as above defined, T and T″ are —O—CH(R′)—O—C(O)—, wherein R′ is as above defined, may be obtained 3c-i) by reacting a compound of formula (IIIe)

P$^3$—X$_6$     (IIIe)

wherein P$^3$, X$_6$ are as above defined with compounds of formula (IVm)

Hal-CH(R′)—O—(O)C-y-Q     (IVm)

wherein R′ and Q are as above defined, Hal is an halogen atom, y is the radical Y when X$_6$ is selected from (a1′), (b1′), (c1′), (e1′), (f2′), (g1′), (h2′), (i2′), (l1′), (m1′), (n1′), (o1′), (p1′), (q1′), (r1′), (s1′), (t1′), (u1′) and (v1′), y is the radical Y′ when X$_6$ is selected from (a3′) and (b3′), wherein Y and Y′ are as defined above, and 3c-ii) when Q is Z$_2$, by converting the compound obtained in the step 3c-i) into nitro derivative by reaction with a nitrate source as above described and 3c-iii) optionally deprotecting the compounds obtained in step 3c-i) or 3c-ii) as above described.

The reaction of a compound of formula (IIIe) wherein P$^3$ and X$_6$ are as above defined, with a compound of formula (IVm) wherein y, Q, R′ are as above defined, may be carried out as described in 1l-i)

3d) The compounds of formula (Ig) wherein X$_2$ is selected from (a1′), (a3′), (b1′), (b3′), (c1′), (e1′), (f2′), (g1′), (h2′), (i2′), (l1′), (m1′), (n1′), (o1′), (p1′), (q1′), (r1″), (s1′), (t1′), (u1′), (v1′), wherein is selected from A1), A2′), A3′), A4′), R$^{1a}$ is selected from A7), R$^{ea}$ is selected from B7) and R$^{2′}$ is selected from B1), B2′), B3′), B4′), and R$^{3a′}$, Y and Y′ are as above defined, T and T″ are —O—CH(R′)—O—C(O)O— wherein R′ is as above defined may be obtained 3d-i) by reacting a compound of formula (IIIe)

P$^3$—X$_6$     (IIIe)

wherein P$^3$ and X$_6$ are as above defined, with compounds of formula (IVo)

Hal-CH(R′)—O—(O)C—O-y-Q     (IVo)

wherein R′ and Q are as above defined, Hal is an halogen atom y is the radical Y when X$_6$ is selected from (a1′), (b1′), (c1′), (e1′), (f2′), (g1′), (h2′), (i2′), (l1′), (m1′), (n1′), (o1′), (p1′), (q1′), (r1′), (s1′), (t1′), (u1′) and (v1′), y is the radical Y′ when X$_6$ is selected from (a3′) and (b3′), wherein Y and Y′ are as defined above, and 3d-ii) when Q is Z$_2$, by converting the compound obtained in the step 3d-i) into nitro derivative by reaction with a nitrate source as above described and 3d-iii) optionally deprotecting the compounds obtained in step 3d-i) or 3d-ii) as above described.

The reaction of a compound of formula (IIIe) wherein P$^3$ and X$_6$ are as above defined, with a compound of formula (IVo) wherein y, Q, R′ are as above defined, may be carried out as described in 1l-i).

3e) The compounds of formula (Ig) wherein X$_2$ is selected from (a7′) or (b7′) wherein R$^{1a}$ is selected from A5) or A6), R$^{1b}$ is selected from B5) or B6) T″ is —C(O)—, T is —X″, —NR′, —O—CH(R′)—O—C(O)— or —O—CH(R′)—O—C(O)O— wherein X″ and R′, Y and Y′ are as above defined, may be obtained 3e-i) by reacting a compound of formula (Ih)

P$^3$—X$_7$     (Ih)

wherein P$^3$ is as above defined and X$_7$ is the radical having the following meaning (a7″) —HN—CH(R$^{1a}$—H)—C(O)-(T-Y-Q)
(b7″) —HN—CH(R$^{2a}$—H)—CH$_2$—C(O)-(T-Y-Q)

wherein R$^{1a}$ is selected from A5) or A6), R$^{2a}$ is selected from B5) or B6), with compounds of formula (IVa)

W$_1$—C(O)-y-Q     (IVa)

wherein $W_1$ and Q are as above defined, y is the radical Y', wherein Y' is as above defined, and 3e-ii) when Q is $Z_{2f}$ by converting the compound obtained in the step 3e-i) into nitro derivative by reaction with a nitrate source as above described and 3e-iii) optionally deprotecting the compounds obtained in step 3e-i) or 3e-ii) as above described.

The reaction of a compound of formula (Ih) wherein $P^3$ and $X_7$ are as above defined, with a compound of formula (IVa) wherein y, Q, $W_1$ are as above defined may be carried out as described in 1-1-i), 1-i-2), 1-i-3) and 1a-i).

The compounds of formula (Ih) wherein $P^3$ and $X_7$ are as above defined, T is —X" are obtained as described in 3a).

The compounds of formula (Ih) wherein $P^3$ and $X_7$ are as above defined, T is —NR' are obtained as described in 3b).

The compounds of formula (Ih) wherein $P^3$ and $X_7$ are as above defined, T is —O—CH(R')—O—C(O)— are obtained as described in 3c).

The compounds of formula (Ih) wherein $P^3$ and $X_7$ are as above defined, T is —O—CH(R')—O—C(O)O— are obtained as described in 3d).

3f) The compounds of formula (Ig) wherein $X_2$ is selected from (a7') or (b7') wherein $R^{1a}$ is selected from A5) or A6), $R^{1b}$ is selected from B5) or B6) T" is —C(O)—X", T is —X", —NR', —O—CH(R')—O—C(O)— or —O—CH(R')—O—C(O)O— wherein X" and R', Y and Y' are as above defined, may be obtained 3f-i) by reacting a compound of formula (Ih)

P³—X₇ (Ih)

wherein $P^3$ and $X_7$ are as above defined with compounds of formula (IVd)

$R_a$—O—C(O)—X"-y-Q (IVd)

wherein $R_a$, X" and Q are as above defined, y is the radical Y', wherein Y' is as above defined, and 3f-ii) when Q is $Z_{2f}$ by converting the compound obtained in the step 3f-i) into nitro derivative by reaction with a nitrate source as above described and 3f-iii) optionally deprotecting the compounds obtained in step 3e-i) or 3f-ii) as above described.

The reaction of a compound of formula (Ih) wherein $P^3$ and $X_7$ are as above defined, with a compound of formula (IVd) wherein y, Q, $R_a$ are as above defined, may be carried out as described in 1-i-2).

3g) The compounds of formula (Ig) wherein $X_2$ is selected from (a7') or (b7') wherein $R^{1a}$ is selected from A5), A6), $R^{1b}$ is selected from B5), B6), T" is —C(O)—NR', T is X", NR', —O—CH(R')—O—C(O)— or —O—CH(R')—O—C(O)O— wherein X" and R', Y and Y' are as above defined, may be obtained 3g-i) by reacting a compound of formula (Ih)

P³—X₇ (Ih)

wherein $P^3$ and $X_7$ are as above defined, with compounds of formula (IVf)

$R_a$—O—C(O)—NR'-y-Q (IVf)

wherein $R_a$ and Q are as above defined, y is the radical Y', wherein Y' is as above defined, and 3g-ii) when Q is $Z_{2f}$ by converting the compound obtained in the step 3g-i) into nitro derivative by reaction with a nitrate source as above described and 3g-iii) optionally deprotecting the compounds obtained in step 3g-i) or 3g-ii) as above described.

The reaction of a compound of formula (Ih) wherein $P^3$ and $X_7$ are as above defined, with a compound of formula (IVf) wherein y, Q, $R_a$ and R' are as above defined may be carried out as described in 1-i-2).

The compounds of formula (Ih) wherein $P^3$ and $X_7$ are as above defined, T is —X" are obtained as described in 3a).

The compounds of formula (Ih) wherein $P^3$ and $X_7$ are as above defined, T is —NR' are obtained as described in 3b).

The compounds of formula (Ih) wherein $P^3$ and $X_7$ are as above defined, T is —O—CH(R')—O—C(O)— are obtained as described in 3c).

The compounds of formula (II) wherein $P^3$ and $X_7$ are as above defined, T is —O—CH(R')—O—C(O)O— are obtained as described in 3d).

3h) The compounds of formula (Ig) wherein $X_2$ is selected from (a7') or (b7') wherein $R^{1a}$ is selected from A7), $R^{1b}$ is selected from B7), T" is —X", T is —X", —NR', —O—CH(R')—O—C(O)— or —O CH(R')—O—C(O)O— wherein X" and R', Y and Y' are as above defined, may be obtained 3h-i) by reacting a compound of formula (Iv)

P³—X₈ (IV)

wherein $P^3$ is as above defined and $X_8$ is the radical having the following meaning (a7") —HN—CH($R^u$—H)—C(O)-(T-Y-Q)

(b7") —HN—CH($R^{2a}$—H)—CH₂—C(O)-(T-Y-Q)

wherein $R^{1a}$ is selected from A7), $R^{1b}$ is selected from B7), with compounds of formula (IVe)

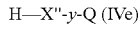

H—X"-y-Q (IVe)

wherein X" and Q are as above defined, y is the radical Y', wherein Y' is as above defined, and 3h-ii) when Q is $Z_2$, by converting the compound obtained in the step 3h-i) into nitro derivative by reaction with a nitrate source as above described and 3h-iii) optionally deprotecting the compounds obtained in step 3h-i) or 3h-ii) as above described.

The reaction of a compound of formula (Iv) wherein $P^3$ and $X_8$ are as above defined, with a compound of formula (IVe) wherein y, Q, X" are as above defined, may be carried out as described in 1-i-1), 1-i-2) and 1a-1).

The compounds of formula (Iv) wherein $P^3$ and $X_8$ are as above defined, T is —X" are obtained as described in 3a).

The compounds of formula (Iv) wherein $P^3$ and $X_8$ are as above defined, T is —NR' are obtained as described in 3b).

The compounds of formula (Iv) wherein $P^3$ and $X_8$ are as above defined, T is —O—CH(R')—O—C(O)— are obtained as described in 3c).

The compounds of formula (Iv) wherein $P^3$ and $X_8$ are as above defined, T is —O—CH(R')—O—C(O)O— are obtained as described in 3d).

3i) The compounds of formula (Ig) wherein $X_2$ is selected from (a7') or (b7') wherein $R^{1a}$ is selected from A7), $R^{1b}$ is selected from B7), T" is NR', T is —X", —NR', —O—CH(R')—O—C(O)— or —O—CH(R')—O—C(O)O— wherein X" and R', Y and Y' are as above defined, may be obtained 3i-i) by reacting a compound of formula (Iv)

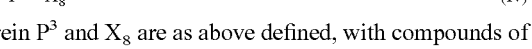

P³—X₈ (Iv)

wherein $P^3$ and $X_8$ are as above defined, with compounds of formula (IVg)

H—NR'-y-Q (IVg)

wherein R' and Q are as above defined, y is the radical Y', wherein Y' is as above defined, and 3i-ii) when Q is $Z_2$, by converting the compound obtained in the step 3i-i) into nitro derivative by reaction with a nitrate source as above described and 3i-iii) optionally deprotecting the compounds obtained in step 3i-i) or 3i-ii) as above described.

The reaction of a compound of formula (Iv) wherein $P^3$ and $X_8$ are as above defined, with a compound of formula (IVg) wherein y, Q, R' are as above defined, may be carried out as described in 1a-i).

3l) The compounds of formula (Ig) wherein $X_2$ is selected from (a7') or (b7') wherein R selected from A7), $R^{1b}$ is selected from B7), T" is —O—CH(R')—O—C(O)—, T is X", NR', —O—CH(R')—O—C(O)— or —O—CH(R')—O—C(O)O— wherein X" and R', Y and Y' are as above defined, may be obtained 3l-i) by reacting a compound of formula (Iv)

$$P^3—X_8 \quad (Iv)$$

wherein $P^3$ and $X_8$ are as above defined with compounds of formula (IVm)

$$Hal-OH(R')—O—(O)C\text{-}y\text{-}Q \quad (IVm)$$

wherein R' and Q are as above defined, y is the radical Y', wherein Y' is as above defined, Hal is an halogen atom and 3l-ii) when Q is $Z_2$, by converting the compound obtained in the step 3i-i) into nitro derivative by reaction with a nitrate source as above described and 3l-iii) optionally deprotecting the compounds obtained in step 3l-i) or 3l-ii) as above described.

The reaction of a compound of formula (Iv) wherein $P^3$ and $X_8$ are as above defined, with a compound of formula (IVm) wherein y, Q, R' are as above defined, may be carried out as described in 1l-i).

3m) The compounds of formula (Ig) wherein $X_2$ is selected from (a7') or (b7') wherein $R^{1a}$ is selected from A7), $R^{1b}$ is selected from B7), T" is —O—CH(R')—O—C(O)O—, T is X", NR', —O—CH(R')—O—C(O)— or —O—CH(R')—O—C(O)O— wherein X" and R', Y and Y' are as above defined, may be obtained 3m-i) by reacting a compound of formula (Iv)

$$P^3—X_8 \quad (Iv)$$

wherein $P^3$ and $X_8$ are as above defined with compounds of formula (IVo)

$$Hal-CH(R')—O—(O)C—O\text{-}y\text{-}Q \quad (IVo)$$

wherein R' and Q are as above defined, y is the radical Y', wherein Y' is as above defined, Hal is an halogen atom and 3m-ii) when Q is $Z_2$, by converting the compound obtained in the step 3m-i) into nitro derivative by reaction with a nitrate source as above described and 3m-iii) optionally deprotecting the compounds obtained in step 3i-i) or 3m-ii) as above described.

The reaction of a compound of formula (Iv) wherein $P^3$ and $X_8$ are as above defined, with a compound of formula (IVo) wherein y, Q, R' are as above defined, may be carried out as described in 1l-i).

3n) The compounds of formula (Ig) wherein $X_2$ is selected from (a3') or (b3'), wherein $R^{1a}$ is selected from A5) or A6), $R^{2a}$ is selected from B5) or B6), Y' is as above defined, T" is C(O) may be obtained 3n-i) by reacting a compound of formula (IIIf), $$P^3—X_9 \quad (IIIf)$$

wherein $P^3$ is as above defined, $X_9$ is a radical having the following meaning (a3") —HN—CH($R^{1a}$—H)—COOR$^{3a'}$
(b3") —HN—CH($R^{2a}$—H)—CH$_2$COOR$^{3a'}$ wherein R selected from A5 or A6) and $R^{2a}$ is selected from B5) or B6), wherein $R^{3a'}$ is as above defined, with compounds of formula (IVa)

$$W_1—C(O)\text{-}y\text{-}Q \quad (IVa)$$

wherein $W_1$ and Q are as above defined, y is the radical Y', wherein Y' is as above defined, and 3n-ii) when Q is $Z_2$, by converting the compound obtained in the step 3n-i) into nitro derivative by reaction with a nitrate source as above described and 3n-iii) optionally deprotecting the compounds obtained in step 3n-i) or 3n-ii) as above described.

The reaction of a compound of formula (IIIf) wherein $P^3$ and $X_9$ are as above defined, with a compound of formula (IVa) wherein $W_1$, y, Q are as above defined, may be carried out as described in 1-i-1), 1-i-2), 1a-1).

The compounds of formula (IIIf) wherein $P^3$ and $X_9$ are as above defined, is commercially available or obtained as known in literature.

3o) The compounds of formula (Ig) wherein $X_2$ is selected from (a3') or (b3'), wherein $R^{1a}$ is selected from A5) or A6), $R^{2a}$ is selected from B5) or B6), Y' is as above defined, T" is C(O)—X" wherein X" is as above defined, can be obtained 3o-i) by reacting a compound of formula (IIIf)

$$P^3—X_9 \quad (IIIf)$$

wherein $P^3$ and $X_9$ are as above defined with compounds of formula (IVd)

$$R_a—O—C(O)—X"\text{-}y\text{-}Q \quad (IVd)$$

wherein $R_a$, X", Q are as above defined, y is the radical Y', wherein Y' is as above defined, and 3o-ii) when Q is $Z_2$, by converting the compound obtained in the step 3o-i) into nitro derivative by reaction with a nitrate source as above described and 3o-iii) optionally deprotecting the compounds obtained in step 3o-i) or 3o-ii) as above described.

The reaction of a compound of formula (IIIf) wherein $P^3$ and $X_9$ are as above defined, with a compound of formula (IVd) wherein $R_a$, X", y, Q are as above defined, may be carried out as described in 1-i-2).

3p) The compounds of formula (Ig) wherein $X_2$ is selected from (a3') or (b3'), wherein $R^{1a}$ is selected from A5) or A6), $R^{2a}$ is selected from B5) or B6), Y' is as above defined, T" is C(O)—NR' wherein R' is as above defined, can be obtained 3p-i) by reacting a compound of formula (IIIg), $$P^3—X_9 \quad (IIIf)$$

wherein $P^3$ and $X_9$ are as above defined, with compounds of formula (IVf)

$$R_a—O—(O)C—NR'\text{-}y\text{-}Q \quad (IVf)$$

wherein $R_a$, R' and Q are as above defined, y is the radical Y', wherein Y' is as above defined, and 3p-ii) when Q is $Z_2$, by converting the compound obtained in the step 3p-i) into nitro derivative by reaction with a nitrate source as above described and 3p-iii) optionally deprotecting the compounds obtained in step 3p-i) or 3p-ii) as above described.

The reaction of a compound of formula (IIIf) wherein $P^3$ and $X_9$ are as above defined, with a compound of formula (IVf) wherein $R_a$, R', y, Q are as above defined, may be carried out as described in 1-i-2).

4) The compound of general formula (I) as above defined wherein a is equal to 1, the radical $R_x$ is selected from (d1), (d2), (d3), (d4), (d7), (d8), Z is C(O), can be obtained 4-i) by reacting a compound of formula (IIb)

$$R—C(O)—O—R_a \quad (IIb)$$

wherein R and $R_a$ are as above defined, with a compound of formula (Im)

$$H—X_{12} \quad (Im)$$

wherein $X_{12}$ is the radical $R_x$ having the following meaning
- (d1') —HN—CH($R^{12'}$)—CH$_2$—O-(T"-Y-Q)
- (d2') —O—OH$_2$—CH($R^{12'}$)—NH-(T'-Y-Q)
- (d3') —HN—CH($R^{12a}$-T"-Y'-Q)-CH$_2$OH
- (d4') —O—CH$_2$—CH($R^{12a}$-T"-Y'-Q)-NHR$^{4a}$
- (d7') —HN—CH($R^{12a}$-T"-Y'-Q)-CH$_2$—O-(T"-Y-Q)
- (d8')    —O—OH$_2$—CH($R^{12a}$-T"-Y'-Q)-NH-(T'-Y-Q)

wherein $R^{12'}$ is
D1),
D2') —CH$_2$—OP$^1$, —CH(CH$_3$)—OP$^1$, —CH$_2$—[(C$_6$H$_4$)-4-OP$^1$], —CH$_2$—[(C$_6$H$_3$)-(3,5-diiodo)-4-OP$^1$], —CH$_2$—[(C$_6$H$_3$)-3-nitro-4-OP$^1$];
D3') —CH$_2$—NHR"", —(CH$_2$—NHR"", —(CH$_2$)$_3$—NHR"", —(CH$_2$)$_4$—NHR"", wherein R"" is as above defined;
D4') —CH$_2$—C(O)R"", —(CH$_2$)$_2$—C(O)R"", —(CH$_2$)$_4$—C(O)R"", wherein R"" is as above defined;
wherein $R^{12a}$ is as above defined; and 4-i) when Q is $Z_2$, by converting the compound obtained in the step 4-i) into nitro derivative by reaction with a nitrate source as above described and 4-iii) optionally deprotecting the compounds obtained in step 4-i) or 4-ii) as above described.

The reaction of a compound of formula (IIb) wherein R and $R_a$ are as above defined, with a compound of formula (Im) wherein $X_{12}$ is as above defined, may be carried out as described in 1-i-2).

4a) The compound of formula (Im) wherein $X_{12}$ is selected from (d1'), (d2'), (d3') or (d4') wherein $R^{12'}$ is selected from D1), D2'), D3') or D4') and $R^{12a}$ is selected from D5) or D6), Y and Y' are as above defined, T' and T" and T'" are C(O) can be obtained 4a-i) by reacting a compound of formula (IIIi),

$$P^4X_{13} \qquad (IIIi)$$

wherein $P^4$ is $P^3$ or $P^1$ as above defined and $X_{13}$ is a radical having the following meaning
- (d1") —HN—CH($R^{12'}$)—CH$_2$—OH
- (d2") —O—CH$_2$—CH($R^{12'}$)—NH$_2$
- (d3") —HN—CH($R^{12a}$—H)—CH$_2$OP$^1$
- (d4") —O—CH$_2$—CH($R^{12a}$—H)—NHR$^{4a'}$ wherein $R^{12'}$ is D1), D2'), D3') or D4'), $R^{12a}$ is D5) or D6), $R^{4a'}$ and $P^1$ are as above defined, with a compound of formula (IVa)

$$W_1—(O)C-y-Q \qquad (IVa)$$

wherein Q and $W_1$ are as above defined, y is the radical Y when $X_{13}$ is selected from (d1') or (d2'), y is the radical Y' when $X_{13}$ is selected from (d3') or (d4'), wherein Y and Y' are as above defined, and 4a-ii) when Q is $Z_2$, by converting the compound obtained in the step 4a-i) into nitro derivative by reaction with a nitrate source as above described and 4a-iii) optionally deprotecting the compounds obtained in step 4a-i) or 4a-ii) as above described.

The reaction of a compound of formula (IIIi) wherein $X_{13}$ and $P^4$ are as above defined, with a compound of formula (IVa) wherein $W_1$, y and Q are as above defined, may be carried out as described in 1-i-1) and 1-i-2).

The compounds of formula (IIIi) wherein $X_{23}$ and $P^4$ are as above described, are commercially available or known in literature.

4b) The compound of formula (Im) wherein $X_{12}$ is selected from (d1'), (d2'), (d3') or (d4') wherein $R^{12'}$ is selected from D1), D2'), D3') or D4') and $R^{12a}$ is selected from D5) or D6), Y and Y' are as above defined, T' and T" and T'" are C(O)—X", wherein X" is as above defined, can be obtained 4b-i) by reacting a compound of formula (IIIi),

$$P^4—X_{13} \qquad (IIIi)$$

wherein $P^4$ and $X_{13}$ are defined above, with a compound of formula (IVd)

$$R_a—O—(O)C—X"-y-Q \qquad (IVd)$$

wherein Q, $R_a$ and X" are as above defined, y is the radical Y when $X_{13}$ is selected from (d1') or (d2'), y is the radical Y' when $X_{13}$ is selected from (d3') or (d4'), wherein Y and Y' are as above defined, and 4b-ii) when Q is $Z_2$, by converting the compound obtained in the step 4b-i) into nitro derivative by reaction with a nitrate source as above described and 4b-iii) optionally deprotecting the compounds obtained in step 4b-i) or 4b-ii) as above described.

The reaction of a compound of formula (IIIi) wherein $X_{13}$ and $P^4$ are as above defined, with a compound of formula (IVd) wherein y, Q, $R_a$ and X" are as above defined, may be carried out as described in 1-i-2).

4c) The compound of formula (Im) wherein $X_{12}$ is selected from (d7') or (d8') wherein $R^{12a}$ is selected from D5) or D6), Y' and Y are as above defined, T' and T" and T'" are C(O), can be obtained 4c-i) by reacting a compound of formula (IIIl),

$$P^4—X_{14} \qquad (IIIl)$$

wherein $P^4$ is $P^1$ or $P^3$, $X_{14}$ is the radical having the following meaning
- (d7") —HN—CH($R^{12a}$—H)—CH$_2$—OH
- (d8") —O—CH$_2$—CH($R^{12a}$—H)—NH$_2$ wherein $R^{12a}$ is selected from D5) or D6), with a compound of formula (IVa)

$$W_1—(O)C-y-Q \qquad (IVa)$$

wherein $W_1$ and Q are as above defined, y is the radical Y', wherein Y' is as above defined, and 4c-ii) when Q is $Z_2$, by converting the compound obtained in the step 4c-i) into nitro derivative by reaction with a nitrate source as above described and 4c-iii) optionally deprotecting the compounds obtained in step 4c-i) or 4c-ii) as above described.

The reaction of a compound of formula (IIII) wherein $P^4$ and $X_{14}$ are as above defined, with a compound of formula (IVa) wherein $W_1$ is OH, y and Q are as above defined, may be carried out as described in 1-i-1) using a ratio (IIII)/(IVa) 1:2.

The reaction of a compound of formula (IIII) wherein $P^4$ and $X_{14}$ are as above defined, with a compound of formula (IVa) wherein $W_1$ is $OR_a$, y and Q are as above defined, may be carried out as described in 1-i-2) using a ratio (IIII)/(IVa) 1:2.

The compounds of formula (IIII) wherein $P^4$ and $X_{14}$ are as above described, are commercially available or known in literature.

4d) The compound of formula (Im) wherein $X_{12}$ is selected from (d7') or (d8') wherein $R^{12a}$ is selected from D5) or D6), Q, Y and Y' are as above defined, T', T" and T'" are C(O), can be obtained 4d-i) by reacting a compound of formula (In)

$$P^4—X_{15} \qquad (In)$$

wherein $P^4$ is defined above and $X_{L5}$ is the radical having the following meaning
- (d7") —HN—CH($R^{12a}$—H)—CH$_2$—O-(T"-Y-Q)
- (d8") —O—OH$_2$—CH($R^{12a}$—H)—NH-(T'-Y-4)

wherein $R^{12a}$ is selected from D5) or D6), Y, Q, T' and T" are as above defined, with a compound of formula (IVa)

$$W_1—(O)C-y-Q \qquad (IVa)$$

wherein $W_1$, y and Q' are as above defined, y is the radical Y', wherein Y' is as above defined, and 4d-ii) when Q is $Z_2$, by converting the compound obtained in the step 4d-i) into nitro derivative by reaction with a nitrate source as above described and 4d-iii) optionally deprotecting the compounds obtained in step 4d-i) or 4d-ii) as above described.

The reaction of a compound of formula (In) wherein $P^4$ and $X_{15}$ it) are as above defined, with a compound of formula (IVa) wherein $W_1$ is OH, y and Q are as above defined, may be carried out as described in 1-i-1).

The reaction of a compound of formula (In) wherein $P^4$ and $X_{15}$ are as above defined, with a compound of formula (IVa) wherein $W_1$ is $OR_a$, y and Q are as above defined, may be carried out as described in 1-i-2).

The compounds of formula (In) wherein $P^4$ and $X_n$ are as above defined, T' and T''' are —C(O)— can by obtained as described in 4a).

4e) The compound of formula (Im) wherein $X_{12}$ is selected from (d7') or (d8') wherein $R^{12a}$ is selected from D5) or D6), Q, Y and Y' are as above defined, T'' is C(O)—X'' wherein X'' is as above defined, T' and T''' are C(O), can be obtained 4e-i) by reacting a compound of formula (In)

$$P^4—X_{15} \quad (In)$$

wherein $P^4$ and $X_{15}$ are defined above, with a compound of formula (IVa)

$$W_1—(O)C-y-Q \quad (IVa)$$

wherein $W_1$, y and Q are as above defined, y is the radical Y', wherein Y' is as above defined, and 4e-ii) when Q is $Z_2$, by converting the compound obtained in the step 1e-i) into nitro derivative by reaction with a nitrate source as above described and 4e-iii) optionally deprotecting the compounds obtained in step 4e-i) or 4e-ii) as above described.

The reaction of a compound of formula (In) wherein $P^4$ and $X_{15}$ are as above defined, with a compound of formula (IVa) wherein $W_1$ is OH, y and Q are as above defined, can by carried out as described in 1-i-1).

The reaction of a compound of formula (In) wherein $P^4$ and $X_{15}$ are as above defined, with a compound of formula (IVa) wherein $W_1$ is $OR_a$, y and Q are as above defined, can by carried out as described in 1-i-2).

The compounds of formula (In) wherein $P^4$ and $X_{15}$ are as above defined can by obtained as described in 4b).

4f) The compound of formula (Im) wherein $X_{12}$ is selected from (d7') or (d8') wherein $R^{12a}$ is selected from D5) or D6), Y and Y' are the same and are as above defined, T', T'' and T''' are C(O)—X'' wherein X'' is as above defined, can be obtained 4f-i) by reacting a compound of formula (IIII), $$P^4—X_{14} \quad (IIII)$$

wherein $P^4$ and $X_{19}$ are as above defined, with a compound of formula (IVd)

$$R_a—O—C(O)—X''-y-Q \quad (IVd)$$

wherein $R_a$, X'' and Q are as above defined, y is the radical Y', wherein Y' is as above defined, and 4f-ii) when Q is $Z_2$, by converting the compound obtained in the step 4f-i) into nitro derivative by reaction with a nitrate source as above described and 4f-iii) optionally deprotecting the compounds obtained in step 4f-i) or 4f-ii) as above described.

The reaction of a compound of formula (IIII) wherein $P^4$ and $X_{14}$ are as above defined, with a compound of formula (IVd) wherein $R_a$, X'', y and Q are as above defined, may be carried out as described in 1-i-2) using a ratio (IIII)/(IVd) 1:2.

4g) The compound of formula (Im) wherein $X_{12}$ is selected from (d7') or (d8') wherein $R^{12a}$ is selected from D5) or D6), Q, Y and Y' are as above defined, T'' is C(O)—X'', T' and T''' are C(O) or C(O)—X'', wherein X'' is as above defined, can be obtained 4g-i) by reacting a compound of formula (In)

$$P^4—X_{15} \quad (In)$$

wherein $P^4$ and $X_{15}$ are as above defined, with a compound of formula (IVd)

$$R_a—O—C(O)—X''-y-Q \quad (IVd)$$

wherein $R_a$, X'' and Q are as above defined, y is the radical Y', wherein Y' is as above defined, and 4g-ii) when Q is $Z_2$, by converting the compound obtained in the step 4g-i) into nitro derivative by reaction with a nitrate source as above described and 4g-iii) optionally deprotecting the compounds obtained in step 4g-i) or 4g-ii) as above described.

The reaction of a compound of formula (In) wherein $P^4$ and $X_{15}$ are as above defined, with a compound of formula (IVd) wherein $R_a$, X'', y and Q are as above defined, may be carried out as described in 1-i-2).

The compounds of formula (In) wherein T' or T'' are C(O), $P^4$ and $X_{15}$ are as above defined are obtained as described in 4a-i), 4a-ii).

The compounds of formula (In) wherein T' or T'' are C(O)—X'', wherein $P^4$ and $X_{15}$ are as above defined are obtained as described in 4b-i), 4b-ii).

4h) The compound of formula (Im) wherein $X_{12}$ is selected from (d7') or (d8') wherein $R^{12a}$ is selected from D5) or D6), Q, Y and Y' are as above defined, T'' is C(O)—NR'—, T' and T''' are C(O) or C(O)—X'', wherein X'' is as above defined, can be obtained 4h-i) by reacting a compound of formula (In)

$$P^4—X_{15} \quad (In)$$

wherein $P^4$ and $X_{15}$ are as above defined, with a compound of formula $$R_a—O—(O)C—NR'-y-Q \quad (IVf)$$

wherein $R_a$, R' and Q are as above defined, y is the radical Y', wherein Y' is as above defined, and 4h-ii) when Q is $Z_2$, by converting the compound obtained in the step 4h-i) into nitro derivative by reaction with a nitrate source as above described and 4h-iii) optionally deprotecting the compounds obtained in step 4h-i) or 4h-ii) as above described.

The reaction of a compound of formula (In) $P^4$ and $X_{15}$ are as above defined, with a compound of formula (IVf) wherein $R_a$, R', y, Q are as above defined, may be carried out as described in 1-i-2).

The compounds of formula (In) wherein T' or T'' are C(O), wherein $P^4$ and $X_{15}$ are as above defined, are obtained as described in 4a-i), 4a-ii).

The compounds of formula (In) wherein T' or T'' are C(O)—X'', wherein $P^4$ and $X_{15}$ are as above defined, are obtained as described in 4b-i), 4b-ii).

4i) The compound of formula (Im) wherein $X_{12}$ is selected from (d7') or (d8') wherein $R^{12a}$ is selected from D7), Q, Y and Y' are as above defined, T'' is X'', wherein X'' is as above defined, T' and T'' are C(O) or C(O)—X'', wherein X'' is as above defined, can be obtained 4i-i) by reacting a compound of formula (Ir), $$P^4X_{16} \quad (Ir)$$

(d7'') —HN—CH($R^{12a}$—OH)—CH$_2$—O-(T'''-Y-Q)
(d8'') —O—CH$_2$—CH($R^{12a}$—OH)—NH-(T'-Y-Q)
wherein $P^4$ is as above defined, $R^{12a}$ is selected from D7), with a compound of formula (IVe)

$$HX''\text{-}y\text{-}Q \quad (IVe)$$

wherein Y', X'' and Q are as above defined, y is the radical Y', wherein Y' is as above defined, and
4i-ii) when Q is $Z_2$, by converting the compound obtained in the step 4i-i) into nitro derivative by reaction with a nitrate source as above described and
4i-iii) optionally deprotecting the compounds obtained in step 4i-i) or 4i-ii) as above described.

The reaction of a compound of formula (Ir) wherein $P^4$ and $X_{16}$ are as above defined with a compound of formula (IVe) wherein y, X'' and Q are as above defined, may be carried out as described in 1-i-1).

The compounds of formula (Ir) wherein T' or T'' are C(O), and $X_{16}$ are as above defined are obtained as described in 4a-i), 4a-ii).

The compounds of formula (Ir) wherein T' or T'' are C(O)—X'', $P^4$ and $X_{16}$ are as above defined, are obtained as described in 4b-i), 4b-ii).

4l) The compound of formula (Im) wherein $X_{12}$ is selected from (d7') or (d8') wherein $R^{12a}$ is selected from D7), Q, Y and Y' are as above defined, T'' is —NR' wherein R' is as above defined, T' and T'' are C(O) or C(O)—X'', wherein X'' is as above defined, can be obtained
4l-i) by reacting a compound of formula (Ir), $$P^4\text{—}X_{16} \quad (Ir)$$

wherein $P^4$ and $X_{16}$ are as above defined and $R^{12a}$ is selected from D7), with a compound of formula $$HR'N\text{-}y\text{-}Q \quad (IVg)$$

wherein R' and Q are as above defined, y is the radical Y', wherein Y' is as above defined, and
4l-ii) when Q is $Z_{2f}$ by converting the compound obtained in the step 4l-i) into nitro derivative by reaction with a nitrate source such above described and
4l-iii) optionally deprotecting the compounds obtained in step 4l-i) or 4l-ii) as above described.

The reaction of a compound of formula (Ir) $P^4$ and $X_{16}$ are as above defined, with a compound of formula (IVg) wherein R', y, Q are as above defined, may be carried out as described in 1-i-1).

4m) The compound of formula (Im) wherein $X_{12}$ is selected from (d7') or (d8') wherein $R^{12'}$ is selected from D7), Q, Y and Y' are as above defined, T'' is —O—CH(R')—O—C(O)—, wherein R' is as above defined, T' and T'' are C(O) or C(O)—X'', wherein X'' is as above defined, can be obtained
4m-i) by reacting a compound of formula (Ir), $$P^4\text{—}X_{16} \quad (Ir)$$

wherein $P^4$ and $X_{16}$ are as above defined and $R^{12'}$ is selected from D7), with a compound of formula (IVm)

$$Hal\text{-}OH(R')\text{—}O\text{—}(O)C\text{-}y\text{-}Q \quad (IVm)$$

wherein R' and Q are as above defined, Hal is an halogen atom, y is the radical Y', wherein Y' is as above defined, and
4m-ii) when Q is $Z_2$, by converting the compound obtained in the step 4m-i) into nitro derivative by reaction with a nitrate source such above described and
4m-iii) optionally deprotecting the compounds obtained in step 4m-i) or 1m-ii) as above described.

The reaction of a compound of formula (Ir) wherein $P^4$ and $X_{16}$ are as above defined, with a compound of formula (IVm) wherein y, Q, R' are as above defined, may be carried out as described in 1l-i).

4n) The compound of formula (Im) wherein $X_{12}$ is selected from (d7') or (d8') wherein $R^{12a}$ is selected from D7), Q, Y and Y' are as above defined, T'' is —O—CH(R')—O—C(O)—O—, wherein R' is as above defined, T' and T''' are C(O) or C(O)—X'', wherein X'' is as above defined, can be obtained
4n-i) by reacting a compound of formula (Ir), $$P^4\text{—}X_{16} \quad (Ir)$$

wherein $P^4$ and $X_{16}$ are as above defined and $R^{12a}$ is selected from D7), with a compounds of formula (IVo)

$$Hal\text{-}CH(R')\text{—}O\text{—}(O)C\text{—}O\text{-}y\text{-}Q \quad (IVo)$$

wherein R and Q' are as above defined, Hal is an halogen atom, y is the radical Y', wherein Y' is as above defined, and
4n-ii) when Q is $Z_2$, by converting the compound obtained in the step 4n-i) into nitro derivative by reaction with a nitrate source as above described and
4n-iii) optionally deprotecting the compounds obtained in step 4n-i) or 4n-ii) as above described.

The reaction of a compound of formula (Ir) wherein $P^4$ and $X_{16}$ are as above defined, with a compound of formula (IVo) wherein y, R', Q, Hal are as above defined, may be carried out as described in 1l-i).

4o) The compound of formula (Im) wherein $X_{12}$ is (selected from d3') or (d4') wherein $R^{12a}$ is selected from D7), Y' is as above defined, T'' is X'', wherein X'' is defined above, can be obtained
4o-i) by reacting a compound of formula (IIIm), $$P^4\text{—}X_{17} \quad (IIIm)$$

wherein $P^4$ is defined above and $X_{17}$ is the radical
(d3'') —HN—CH($R^{12a}$—H)—CH$_2$OP$^1$
(d4'') —O—CH$_2$—CH($R^{12a}$—H)—NHR$^{4a'}$
wherein $R^{12a}$ is selected from D7), wherein $P^1$ and $R^{4a'}$ are as above defined, with a compound of formula (IVe)

$$HX''\text{-}y\text{-}Q \quad (IVe)$$

wherein X'' and Q are as above defined, y is the radical Y', wherein Y' is as above defined, and
4o-ii) when Q is $Z_{2f}$ by converting the compound obtained in the step 4o-i) into nitro derivative by reaction with a nitrate source as above described and
4o-iii) optionally deprotecting the compounds obtained in step 4o-i) or 4o-ii) as above described.

The reaction of a compound of formula (IIIm) wherein $P^4$ and $X_{17}$ are as above defined with a compound of formula (IVe) wherein y, X'' and Q are as above defined, may be carried out as described in 1-i-1).

The compounds of formula (IIIm), wherein $P^4$ and $X_{17}$ are as above defined, are commercially available or obtained as known in literature.

4p) The compound of formula (Im) wherein $X_{12}$ is selected from (d3') or (d4') wherein $R^{12a}$ is selected from D7), Y' is as above defined, T'' is —NR' wherein R' is as above defined, can be obtained
4p-i) by reacting a compound of formula (IIIm), $$P^4\text{—}X_{17} \quad (IIIm)$$

wherein $P^4$ and $X_{17}$ are as defined above, wherein $R^{12a}$ is selected from D7), with a compound of formula $$HR'N\text{-}y\text{-}Q \quad (IVg)$$

wherein R' and Q are as above defined, y is the radical Y', wherein Y' is as above defined, and 4p-ii) when Q is $Z_2$, by converting the compound obtained in the step 4p-i) into nitro derivative by reaction with a nitrate source such above described and 4p-iii) optionally deprotecting the compounds obtained in step 4p-i) or 4p-ii) as above described.

The reaction of a compound of formula (IIIm) wherein $P^4$ and $X_{17}$ are as above defined, with a compound of formula (IVg) wherein R', y, Q are as above defined, may be carried out as described in 1a-i).

4q) The compound of formula (Im) wherein $X_{12}$ is selected from (d3') or (d4') wherein $R^{12a}$ is selected from D7), Y' is as above defined, T" is —O—CH(R')—O—C(O)— wherein R' is as above defined, can be obtained 4q-i) by reacting a compound of formula (IIIm), $$P^4\text{—}X_{17} \tag{IIIm}$$

wherein $P^4$ and $X_{17}$ are as defined above, wherein $R^{12a}$ is selected from D7), with a compound of formula (IVm)

$$\text{Hal-CH(R')—O—(O)C-}y\text{-Q} \tag{IVm}$$

wherein R' and Q are as above defined, Hal is an halogen atom, y is the radical Y', wherein Y' is as above defined, and 4q-ii) when Q is $Z_2$, by converting the compound obtained in the step 4q-i) into nitro derivative by reaction with a nitrate source such above described and 4q-iii) optionally deprotecting the compounds obtained in step 4q-i) or 4q-ii) as above described.

The reaction of a compound of formula (IIIm) wherein $P^4$ and $X_{17}$ are as above defined, with a compound of formula (IVm) wherein R', y, Q are as above defined, may be carried out as described in 1l-i).

4r) The compound of formula (Im) wherein $X_{12}$ is selected from (d3') or (d4') wherein $R^{12a}$ is selected from D7), Y' is as above defined, T" is —O—CH(R')—O—C(O)—O— wherein R' is as above defined, can be obtained 4r-i) by reacting a compound of formula (IIIm), $$P^4\text{—}X_{17} \tag{IIIm}$$

wherein $P^4$ and $X_{17}$ are as defined above, wherein $R^{12a}$ is selected from D7), with a compound of formula (IVo)

$$\text{Hal-CH(R')—O—(O)C—O-}y\text{-Q} \tag{IVo}$$

wherein R' and Q are as above defined, Hal is an halogen atom, y is the radical Y', wherein Y' is as above defined, and 4r-ii) when Q is $Z_2$, by converting the compound obtained in the step 4r-i) into nitro derivative by reaction with a nitrate source as above described and 4r-iii) optionally deprotecting the compounds obtained in step 4r-i) or 4r-ii) as above described.

The reaction of a compound of formula (IIIm) wherein $P^4$ and $X_{17}$ are as above defined, with a compound of formula (IVo) wherein y, R', Q, Hal are as above defined, may be carried out as described in 1l-i).

5) The compound of general formula (I) as above defined wherein a is equal to 0, $R_x$ is a radical selected from (d5), (d6), (d9) or (d10), wherein $R^{12b}$ is selected from D10) can be obtained 5-i) by reacting a compound of formula (IIa)

$$R\text{—}H \tag{IIa}$$

wherein R is as above defined, with a compound of formula (Is)

$$W\text{—}X_{18} \tag{Is}$$

wherein W is as above defined, $X_{18}$ is the radical having the following meanings (d5') —$R^{12b}$—CH(NHR$^{4a}$)—CH$_2$—O-(T'''-Y-Q)
(d6') —$R^{12b}$—CH(CH$_2$OH)—NH-(T'-Y-Q)
(d9') —$R^{12b}$—CH(NH-T'''-Y'-Q)-CH$_2$—O-(T'-Y-Q)
(d10') —$R^{12b}$—CH(CH$_2$—O-T''-Q)-NH-(T'-Y-Q)

wherein $R^{12b}$ is selected from D10), T', T''', Y, Y' and Q are as above defined and 5-ii) when Q is $Z_2$, by converting the compound obtained in the step 5-i) into nitro derivative by reaction with a nitrate source as above described and 5-iii) optionally deprotecting the compounds obtained in step 5-i) or 5-ii) as above described.

The reaction of a compound of formula (IIa) wherein R is as above defined, with a compound of formula (Is) wherein W and $X_{18}$ are as above defined may be carried out as described in 1).

5a) The compounds of formula (Is) wherein $X_{18}$ is a radical of formula (d5') or (d6'), wherein $R^{12b}$ is selected from D10), T' and T'' are C(O) can be obtained 5a-i) by reacting a compound of formula (IIIn), $$P^2\text{—}X_{19} \tag{IIIn}$$

wherein $P^2$ is as above defined, $X_{19}$ is the radical having the following meanings (d5'') —$R^{12b}$—CH(NHP$^3$)—CH$_2$—OH
(d6'') —$R^{12b}$—CH(CH$_2$OP$^1$)—NH$_2$ wherein $P^1$ and $P^3$ are as above defined and $R^{12b}$ is selected from D10), with a compound of formula (IVa)

$$W_1\text{—}C(O)\text{-}y\text{-Q} \tag{IVa}$$

wherein $W_1$, y, Q are as above defined, y is the radical Y, wherein Y is as above defined, and 5a-ii) when Q is $Z_2$, by converting the compound obtained in the step 5a-i) into nitro derivative by reaction with a nitrate source as above described and 5a-i) optionally deprotecting the compounds obtained in step 5a-i) or 5a-ii) as above described.

The reaction of a compound of formula (IIIn) wherein $P^2$ and $X_{19}$ are as above defined, with a compound of formula (IVa) $W_1$, y, and Q are as above defined may be carried out as described in 1-i-1), 1-i-2), 1-i-3) and 1a-1).

The compounds of formula (IIIn), wherein $P^2$ and $X_{19}$ are as above defined, are commercially available or obtained as known in literature.

5b) The compounds of formula (Is) wherein $X_{18}$ is a radical of formula (d5') or (d6'), wherein $R^{12b}$ is selected from D10), T' and T''' are C(O)—X'', wherein X'' is defined above, can be obtained 5b-i) by reacting a compound of formula (IIIn), $$P^2\text{—}X_{19} \tag{IIIn}$$

wherein $P^2$ and $X_{19}$ are as above defined, with a compound of formula (IVd)

$$R_a\text{—O—C(O)—X''-}y\text{-Q} \tag{IVd}$$

wherein $R_a$ and Q, X'' are as above defined, y is the radical Y, wherein Y is as above defined, and 5b-ii) when Q is $Z_{2f}$ by converting the compound obtained in the step 5b-i) into nitro derivative by reaction with a nitrate source as above described and 5b-iii) optionally deprotecting the compounds obtained in step 5b-i) or 5b-ii) as above described.

The reaction of a compound of formula (IIIn) wherein $P^2$ and $X_{19}$ are as above defined, with a compound of formula (IVd) $R_a$, y, Q, X'' are as above defined may be carried out as described in 1-i-2).

5c) The compounds of formula (Is) wherein $X_{18}$ is a radical of formula (d9'), wherein $R^{12b}$ is selected from D10), Y and Y' are as defined above, T' is C(O)— and T''' is C(O) or C(O)—X'', wherein X'' is defined above, can be obtained 5c-i) by reacting a compound of formula (It), $$P^2\text{—}X_{20} \tag{It}$$

wherein $P^2$ is as above defined and $X_{20}$ is the radical having the following meanings (d9''') —$R^{12b}$—CH(NH$_2$)—CH$_2$—O-(T'''-Y-Q)

wherein $R^{12b}$ is selected from D10), T'', Y and Q are as above defined, with a compound of formula (IVa)

$$W_1—C(O)\text{-}y\text{-}Q \qquad\qquad (IVa)$$

wherein $W_1$ and Q are as above defined, y is the radical Y', wherein Y' is as above defined, and 5c-ii) when Q is $Z_2$, by converting the compound obtained in the step 5c-i) into nitro derivative by reaction with a nitrate source as above described and 5c-iii) optionally deprotecting the compounds obtained in step 5c-i) or 5c-ii) as above described.

The reaction of a compound of formula (It) wherein $P^2$ and $X_{20}$ are as above defined, with a compound of formula (IVa) wherein $W_1$, y, 4 are as above defined, may be carried out as described in 1-i-1), 1-i-2), 1-i-3) and 1a-1).

5d) The compounds of formula (Is) wherein $X_{18}$ is a radical of formula (d9'), wherein $R^{12b}$ is selected from D10), T' is C(O)—X'' and T'' is C(O)— or C(O)—X'', wherein X'' is defined above, can be obtained 5d-i) by reacting a compound of formula (It'), $$P^2—X_{20'} \qquad\qquad (It')$$

wherein $P^2$ and $X_{20'}$ are as above defined, with a compound of formula (IVd)

$$R_a—O—C(O)—X''\text{-}y\text{-}Q \qquad\qquad (IVd)$$

wherein $R_a$ and Q, X'' are as above defined, y is the radical Y', wherein Y' is as above defined, and 5d-ii) when Q is $Z_2$, by converting the compound obtained in the step 5d-i) into nitro derivative by reaction with a nitrate source as above described and 5d-iii) optionally deprotecting the compounds obtained in step 5d-i) or 5d-ii) as above described.

The reaction of a compound of formula (It') wherein $P^2$ and $X_{20'}$ are as above defined, with a compound of formula (IVd) $R_a$, y, X'' are as above defined may be carried out as described in 1-i-2).

5e) The compounds of formula (Is) wherein $X_{18}$ is the radical of formula (d10'), wherein $R^{12b}$ is selected from D10), Y and Y' are as defined above, T'' is C(O)— and T' is C(O) or C(O)—X'', wherein X'' is defined above, can be obtained 5e-i) by reacting a compound of formula (It), $$P^2—X_{20} \qquad\qquad (It)$$

wherein $P^2$ is as above defined and $X_{20}$ is the radical having the following meaning (d10'') —$R^{12b}$—CH(CH$_2$—OH)—NH-(T'-Y-Q) wherein $R^{12b}$ is selected from D10), T', Y and Q are as above defined, with a compound of formula (IVa)

$$W_1—C(O)\text{-}y\text{-}Q \qquad\qquad (IVa)$$

wherein $W_1$ and Q are as above defined, y is the radical Y', wherein Y' is as above defined, and 5e-ii) when Q is $Z_2$, by converting the compound obtained in the step 5e-i) into nitro derivative by reaction with a nitrate source as above described and 5e-iii) optionally deprotecting the compounds obtained in step 5e-i) or 5e-ii) as above described.

The reaction of a compound of formula (It) wherein $P^2$ and $X_{20}$ are as above defined, with a compound of formula (IVa) wherein $W_1$, y, Q are as above defined, may be carried out as described in 1-i-1), 1-i-2), 1-i-3) and 1a-1).

5f) The compounds of formula (Is) wherein $X_{18}$ is the radical of formula (d10'), wherein $R^{12b}$ is selected from D10), T'' is C(O)—X'' and T' is C(O)— or C(O)—X'', wherein X'' is defined above, can be obtained 5f-i) by reacting a compound of formula (It'), $$P^2—X_{20'} \qquad\qquad (It')$$

wherein $P^2$ and $X_{20'}$ are as above defined, with a compound of formula (IVd)

$$R_a—O—C(O)—X''\text{-}y\text{-}Q \qquad\qquad (IVd)$$

wherein $R_a$ and Q, X'' are as above defined, y is the radical Y', wherein Y' is as above defined, and 5f-ii) when Q is $Z_2$, by converting the compound obtained in the step 5f-i) into nitro derivative by reaction with a nitrate source as above described and 5f-iii) optionally deprotecting the compounds obtained in step 5f-i) or 5f-ii) as above described.

The reaction of a compound of formula (It') wherein $P^2$ and $X_{20'}$ are as above defined, with a compound of formula (IVd) $R_a$, y, Q, X'' are as above defined may be carried out as described in 1-i-2).

6) The compounds of general formula (I) as above defined wherein a is equal to 1, $R_x$ is a radical selected from (d5), (d6), (d9) or (d10), wherein $R^{12b}$ is selected from D10), Z is —CH(R')—O—, wherein R' is defined above, can be obtained 6-i) by reacting a compound of formula (IIa)

$$R—OH \qquad\qquad (IIa)$$

wherein R is as above defined with a compound of formula (Iu)

$$\text{Hal-CH(R')—O—}X_{21} \qquad\qquad (Iu)$$

wherein Hal is an halogen atom, R' is as above defined and $X_{21}$ is a radical selected from (d5'), (d6'), (d9') or (d10'), wherein $R^{12b}$ is selected from D10), and 6-ii) when Q is $Z_{2f}$ by converting the compound obtained in the step 6-i) into nitro derivative by reaction with a nitrate source as above described and 6-iii) optionally deprotecting the compounds obtained in step 6-i) or 6-ii) as above described.

The reaction of a compound of formula (Iu) wherein Hal, $X_n$ and R' are as above defined, with a compound of formula (IIa) wherein R is as above defined, may be carried out as described in 1l-i).

The compounds of formula (Iu) are obtained by reacting a compound R'—CHO, wherein R' is as above defined with compounds of formula (IIIo)

$$W—X_{22} \qquad\qquad (IIIo)$$

wherein W is a chlorine atom, $X_{22}$ is the radical having the following meanings (d5''') —$R^{12b}$—CH(NHP$^3$)—CH$_2$—O-(T'''-Y-Q)
(d6''') —$R^{12b}$—CH(CH$_2$OP$^1$)—NH-(T'-Y-Q)
(d9''') —$R^{12b}$—CH(NH-T'-Y'-Q)-CH$_2$—O-(T'''-Y-Q)
(d10''') —$R^{12b}$—CH(CH$_2$—O-T'''-Y'-Q)-NH-(T'-Y-Q)

wherein $R^{12b}$, P$^3$, P$^1$, T', T'', Y', Y and Q are as above defined, and ZnCl$_2$ as known in literature.

The compounds of formula (IIIo), wherein W and $X_{22}$ are as above defined, may be carried out as described in 5).

7) The compounds of general formula (I) as above defined wherein a is equal to 1, $R_x$ is a radical selected from (d5), (d6), (d9) or (d10), wherein $R^{12b}$ is selected from D8) or D9), Z is —C(O)—, can be obtained 7-i) by reacting a compound of formula (IIb)

$$R—C(O)—O—R_a, \qquad\qquad (IIb)$$

wherein R and $R_a$ are as above defined with a compound of formula (Iv)

$$H—X_{23} \qquad\qquad (Iv)$$

wherein $X_{23}$ is a radical selected from (d5'), (d6'), (d9') or (d10'), wherein $R^{12b}$ is selected from D8) or D9), and 7-ii) when Q is $Z_2$, by converting the compound obtained in the step 7-i) into nitro derivative by reaction with a nitrate source as above described and 7-iii) optionally deprotecting the compounds obtained in step 7-i) or 7-ii) as above described.

The reaction of a compound of formula (Iv) wherein $X_{23}$ and is as above defined, with a compound of formula (IIb) wherein R is as above defined, may be carried out as described in 11-i).

8) The compound of general formula (I) as above defined wherein a is equal to 0, $R_x$ is a radical selected from (a5), (a6), (a9) or (a10), (b5), (b6), (b9) or (MO) wherein $R^{1b}$ is selected from A10) and $R^{2b}$ is selected from B10), can be obtained 8-i) by reacting a compound of formula (IIa)

R—H (IIa)

wherein R is as above defined, with a compound of formula (Iz)

W—$X_{24}$ (Iz)

wherein W is as above defined, $X_{24}$ is the radical $R_x$ having the following meanings
- (a5') —$R^{1b}$—CH(NHR$^{4a}$)—C(O)-(T-Y-Q)
- (a6') —$R^{1b}$—CH(COOR$^{3a}$)NH-(T'-Y-Q)
- (a9') —$R^{1b}$—CH(NH-T'-Y'-Q)-C(O)-(T-Y-Q)
- (a10') —$R^{1b}$—CH(C(O)-T'-Q)-NH-(T-Y-Q)
- (b5') —$R^{2b}$—CH(NHR$^{4a}$)—CH$_2$C(O)-(T-Y-Q)
- (b6') —$R^{2b}$—CH(CH$_2$COOR$^{3a}$)NH-(T'-Y-Q)
- (b9') —$R^{2b}$—CH(NH-T'-Y'-Q)-CH$_2$C(O)-(T-Y-Q)
- (b10') —$R^{2b}$—CH(CH$_2$C(O)-T'-Y'-Q)-NH-(T-Y-Q)

wherein $R^{1b}$ is selected from A10), $R^{2b}$ is selected from B10), T,

T', Y and Q are as above defined and 8-ii) when Q is $Z_2$, by converting the compound obtained in the step 8-i) into nitro derivative by reaction with a nitrate source as above described and 8-iii) optionally deprotecting the compounds obtained in step 8-i) or 8-ii) as above described.

The reaction of a compound of formula (IIa) wherein R is as above defined, with a compound of formula (Iv) wherein W and $X_{24}$ are as above defined may be carried out as described in 1).

8a) The compounds of formula (Iz) wherein $X_{24}$ is a radical of formula (a5'), (a6'), (b5') or (b6'), wherein $R^{1b}$ is selected from A10) and $R^{2b}$ is selected from B10), T and T' are C(O) can be obtained 8a-i) by reacting a compound of formula (IIIq),

P$^2$—$X_{25}$ (IIIq)

wherein P$^2$ is as above defined, $X_{25}$ is the radical having the following meanings
- (a5") —$R^{1b}$—CH(NHP$^3$)—C(O)—OH
- (a6") —$R^{1b}$—CH(COOP$^2$)—NH$_2$
- (b5") —$R^{2b}$—CH(NHP$^3$)—CH$_2$C(O)—OH
- (b6") —$R^{2b}$—CH(CH$_2$COOP$^2$)NH$_2$ wherein P$^2$ and P$^3$ are as above defined and $R^{1b}$ is selected from A10), $R^{2b}$ is selected from B10), with a compound of formula III (IVa)

W$_1$—C(O)-y-Q (IVa)

wherein W$_1$, and Q are as above defined, y is the radical Y, wherein Y is as above defined, and 8a-ii) when Q is $Z_2$, by converting the compound obtained in the step 8a-i) into nitro derivative by reaction with a nitrate source as above described and 8a-iii) optionally deprotecting the compounds obtained in step 8a-i) or 8a-ii) as above described.

The reaction of a compound of formula (IIIq) wherein P$^2$ and $X_{25}$ are as above defined, with a compound of formula (IVa) W$_1$, Y, and Q are as above defined may be carried out as described in 1-i-1), 1-i-2), 1-i-3) and 1a-1).

The compounds of formula (IIIq), wherein P$^2$ and $X_{25}$ are as above defined, are commercially available or obtained as known in literature.

8b) The compounds of formula (Iz) wherein $X_{24}$ is the radical of formula (a5'), (a6'), (b5') or (b6'), wherein $R^{1b}$ is selected from A10) and $R^{2b}$ is selected from B10), T and T' are C(O)—X", wherein X" is defined above, can be obtained 8b-i) by reacting a compound of formula (IIIq),

P$^2$—$X_{25}$ (IIIq)

wherein P$^2$ and $X_{25}$ are as above defined, with a compound of formula (IVd)

R$_a$—O—C(O)—X"-y-Q (IVd)

wherein R$_a$, Q and X" are as above defined, y is the radical Y, wherein Y is as above defined, and 8b-ii) when Q is $Z_2$, by converting the compound obtained in the step 8b-i) into nitro derivative by reaction with a nitrate source as above described and 8b-iii) optionally deprotecting the compounds obtained in step 8b-i) or 8b-ii) as above described.

The reaction of a compound of formula (IIIq) wherein P$^2$ and $X_{25}$ are as above defined, with a compound of formula (IVd) R$_a$, y, Q, X" are as above defined may be carried out as described in 1-i-2).

8c) The compounds of formula (Iz) wherein $X_{24}$ is the radical of formula (a9') or (b9') wherein $R^{1b}$ is selected from A10), and $R^{2b}$ is selected from B10) Y and Y' are as defined above, T is C(O)— or C(O)—X", wherein X" is defined above and T' is C(O) can be obtained 8c-i) by reacting a compound of formula (Iy),

P$^2$—$X_{26}$ (Iy)

wherein P$^2$ is as above defined and $X_{26}$ is the radical having the following meanings
- (a9") —$R^{1b}$—CH(NH$_2$)—C(O)-(T-Y-Q)
- (b9") —$R^{2b}$—CH(NH$_2$)—CH$_2$C(O)-(T-Y-Q)

wherein $R^{1b}$ is selected from A10) and $R^{2b}$ is selected from B10), with a compound of formula (IVa)

W$_1$—C(O)-y-Q (IVa)

wherein W$_1$ and Q are as above defined, y is the radical Y', wherein Y' is as above defined, and 8c-ii) when Q is $Z_2$, by converting the compound obtained in the step 8c-i) into nitro derivative by reaction with a nitrate source as above described and 8c-iii) optionally deprotecting the compounds obtained in step 8c-i) or 8c-ii) as above described.

The reaction of a compound of formula (Iy) wherein P$^2$ and $X_{26}$ are as above defined, with a compound of formula (IVa) wherein W$_1$, y, Q are as above defined, may be carried out as described in 1-i-1), 1-i-2), 1-i-3) and 1a-1).

8d) The compounds of formula (Iz) wherein $X_{24}$ is the radical of formula (a9') or (b9') wherein $R^{1b}$ is selected from A10), $R^{2b}$ is selected from B10), Y and Y' are as defined above, T is C(O)— or C(O)—X", wherein X" is defined above and T' is C(O)—X" can be obtained 8d-i) by reacting a compound of formula (Iy),

P$^2$—$X_{26}$ (Iy)

wherein P$^2$ and $X_{26}$ are as above defined, with a compound of formula (IVd)

R$_a$—O—C(O)—X"-y-Q (IVd)

wherein $R_a$ and X" are as above defined, y is the radical Y', wherein Y' is as above defined, and 8d-ii) when Q is $Z_2$, by converting the compound obtained in the step 8d-i) into nitro derivative by reaction with a nitrate source as above described and 8d-iii) optionally deprotecting the compounds obtained in step 8d-i) or 8d-ii) as above described.

The reaction of a compound of formula (Iy) wherein $P^2$ and $X_{20}$ are as above defined, with a compound of formula (IVd) $R_a$, y, Q, X" are as above defined may be carried out as described in 1-i-2).

8e) The compounds of formula (Iz) wherein $X_{24}$ is the radical of formula (a10') or (b10') wherein $R^{1b}$ is selected from A10), and $R^{2b}$ is selected from in B10) Y and Y' are as defined above, T is C(O)— or C(O)—X", wherein X" is defined above and T' is C(O) can be obtained 8e-i) by reacting a compound of formula)(Iy'),

wherein $P^2$ is as above defined and $X_{26'}$ is the radical having the following meanings (a10") —$R^{1b}$—CH(C(O)—OH)—NH-(T-Y-Q)
(b10") —$R^{2b}$—CH(CH$_2$C(O)—OH)—NH-(T-Y-Q)

wherein $R^{1b}$ is selected from selected from A10) and $R^{2b}$ is B10), with a compound of formula (IVa)

wherein $W_1$ and Q are as above defined, y is the radical Y', wherein Y' is as above defined, and 8e-ii) when Q is $Z_2$, by converting the compound obtained in the step 8e-i) into nitro derivative by reaction with a nitrate source as above described and 8e-iii) optionally deprotecting the compounds obtained in step 8e-i) or 8e-ii) as above described.

The reaction of a compound of formula (Iy') wherein $P^2$ and $X_{26'}$ are as above defined, with a compound of formula (IVa) wherein $W_1$, y, Q are as above defined, may be carried out as described in 1-i-1), 1-i-2), 1-i-3) and 1a-1).

8f) The compounds of formula (Iz) wherein $X_{24}$ is the radical of formula (a10') or (b10') wherein $R^{1b}$ is selected from A10), and $R^{2b}$ is selected from B10), Y and Y' are as defined above, T is C(O)— or C(O)—X", wherein X" is defined above and T' is C(O)—X" can be obtained 8f-i) by reacting a compound of formula (Iy'),

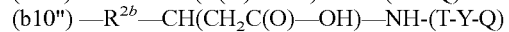

wherein $P^2$ and $X_{26'}$ are as above defined, with a compound of formula (IVd)

wherein $R_a$ and X" are as above defined, y is the radical Y', wherein Y' is as above defined, and 8f-ii) when Q is $Z_{2f}$ by converting the compound obtained in the step 8f-i) into nitro derivative by reaction with a nitrate source as above described and 8f-iii) optionally deprotecting the compounds obtained in step 8f-i) or 8f-ii) as above described.

The reaction of a compound of formula (Iy') wherein $P^2$ and $X_{26'}$ are as above defined, with a compound of formula (IVd) $R_a$, y, Q, X" are as above defined may be carried out as described in 1-i-2).

9) The compounds of general formula (I) as above defined wherein a is equal to 1, $R_x$ is a radical selected from (a5), (a6), (a9) or (a10), (b5), (b6), (b9) or (b10) wherein $R^{1b}$ is selected from A8) or A9), $R^{2b}$ is selected from B8) or B9), Z is —C(O)—, can be obtained 9-i) by reacting a compound of formula (IIb)

wherein R and $R_a$ are as above defined with a compound of formula (Ix)

wherein $X_{27}$ is the radical selected from (a5'), (a6'), (a9'), (a10'), (b5'), (b6'), (b9') or (b10'), wherein $R^{2b}$ is selected from A8) or A9), $R^{2b}$ is selected from B8) or B9), and 9-ii) when Q is $Z_2$, by converting the compound obtained in the step 9-i) into nitro derivative by reaction with a nitrate source as above described and 9-iii) optionally deprotecting the compounds obtained in step 9-i) or 9-ii) as above described.

The reaction of a compound of formula (Ix) wherein $X_{27}$ and is as above defined, with a compound of formula (IIb) wherein R is as above defined, may be carried out as described in 11-i).

Example 1

Synthesis of (11β,16β)-9-Chloro-11,17-dihydroxy-16-methyl-21-[1-oxo-((2-(4-(nitrooxy)butyloxy-carbonylamino)acetyl)]-pregna-1,4-diene-3,20-dione

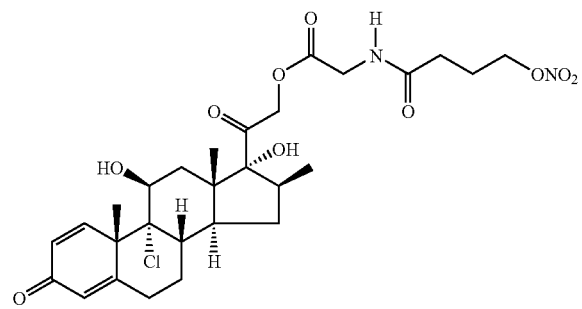

(11β,16β)-9-Chloro-11,17-dihydroxy-16-methyl-21-[1-oxo-2-((tert-butylcarbonylamino)acetyl)]-pregna-1,4-diene-3,20-dione

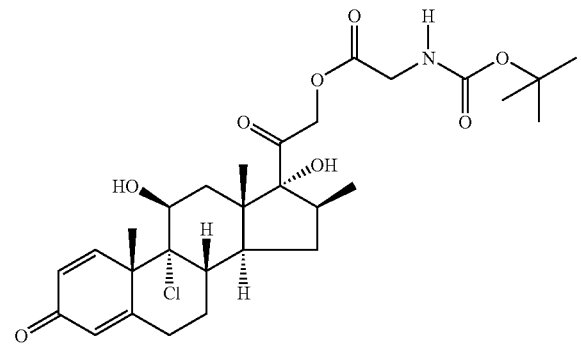

To solution of beclomethasone (0.6 g, 1.46 mmol) in acetone (35 ml), N-Boc-glycine (0.334 g, 1.90 mmol) and DMAP (cat. amount) were added. The reaction was cooled at 0° C. and EDAC (0.365 g, 1.90 mmol) was added. The reaction was stirred at room temperature for 2 hours. The solvent was evaporated under vacuum. The residue was treated with water (50 ml) and methylene chloride (50×3 ml), the organic layers were dried over sodium sulfate and concentrated under reduced pressure. The residue was purified by flash chromatography, eluent n-hexane/ethyl acetate 6/4. The product (0.8 g) was obtained.

(11β,16β)-9-Chloro-11,17-dihydroxy-16-methyl-21-[1-oxo-2-((carbonylamino)acetyl)]-pregna-1,4-diene-3,20-dione Hydrochloride

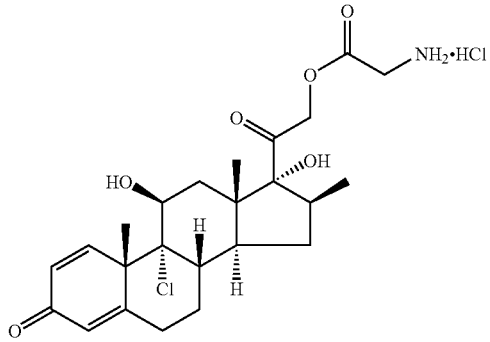

A solution of compound A (0.8 g, 0.41 mmol) in methylene chloride (70 ml) was stirred at room temperature. HCl gas was buddle in the solution for 1 hour. The solvent was evaporated under reduced pressure. The product was used in the next step without any purification.

(11β,16β)-9-Chloro-11,17-dihydroxy-16-methyl-21-[1-oxo-(2-((4-(nitrooxy)butyoxy-carbonylamino)acetyl)]-pregna-1,4-diene-3,20-diene To a solution of B) (0.75 g, 1.46 mmol) in methylene chloride (40 ml), 4-nitrooxybutyrric acid pentafluorophenyl ester (0.41 g, 1.46 mmol), DMAP (cat. amount) and triethylamine (0.3 ml, 2.19 mmol) were added. The reaction was stirred at room temperature for 24 hours. The solution was treated with a 5% solution of $H_3PO_4$ (50 ml). The organic layer was dried over sodium sulfate and concentrated under reduced pressure. The residue was purified by flash chromatography, (Biotage System, column FLASH 40+M™ KP-Sil) eluent:gradient n-hexane/ethyl acetate 1/1 (130 ml), to ethyl acetate 100% during 130 ml, ethyl acetate 100% (130 ml). The product (0.62 g) was obtained as white powder.

$^1$H-NMR: (DMSO), δ: 8.42 (1H, t); 7.30 (1H, d); 6.22 (1H, dd); 5.98 (1H, s); 5.46 (1H, d); 5.42 (2H, s); 5.05 (1H, d); 4.84 (1H, d); 4.5 (2H, t); 4.34 (1H, sb); 3.97 (2H, d); 2.71-2.57 (2H, m); 2.5-2.2 (6H, m); 2.0-1.7 (5H, m); 1.65-1.35 (5H, m); 1.25-0.97 (4H, m); 0.8 (3H, s).

Example 2

Synthesis of (11β,16β)-9-Fluoro-11,17-dihydroxy-16-methyl-21-[1-oxo-(2-((4-(nitrooxy)butyoxy-carbonylamino)acetyl)]-pregna-1,4-diene-3,20-dione

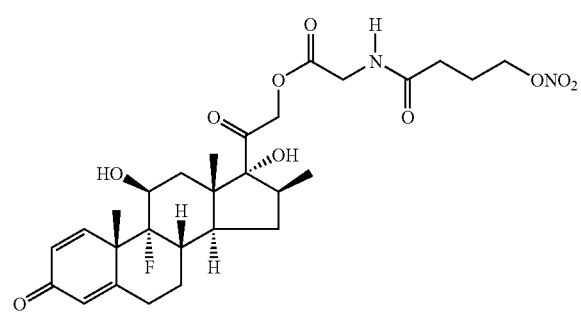

The compound was synthesized using the procedure described in example 1 starting from betamethasone, Boc-glycine and 4-nitrooxybutyric acid pentafluorophenol ester.

$^1$H-NMR: (DMSO), δ: 8.4 (1H, t); 7.28 (1H, d); 6.22 (1H, dd); 6.0 (1H, s); 5.30 (1H, d); 5.08 (1H, d); 4.83 (1H, d); 4.53 (2H, t); 4.15 (1H, bp); 3.95 (2H, d); 2.71-2.52 (1H, m); 2.51-2.4 (6H, m); 2.38-2.07 (2H, m); 2.03-1.75 (6H, m); 1.58-1.45 (4H, m), 1.11-0.8 (6H, m).

Example 3

Synthesis of (11β,16β)-9-Fluoro-11-hydroxy-16,17-(1-methylethylidenebis(oxy))-21-[1-oxo-(2-(4-(nitrooxy)butyoxy-carbonylamino)acetyl)]-pregna-1,4-diene-3,20-dione

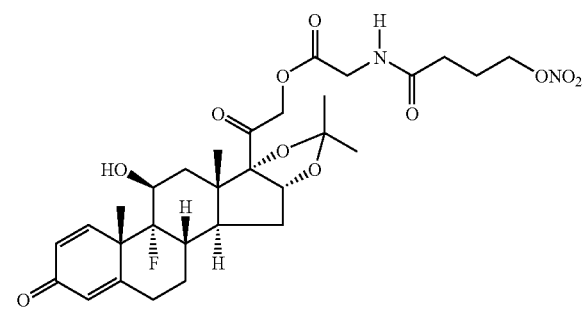

The compound was synthesized using the procedure described in example 1 starting from triamcinolone acetonide, Boc-glycine and 4-nitrooxybutyric acid pentafluorophenol ester.

$^1$H-NMR: (DMSO), δ: 8.43 (1H, t); 7.27 (1H, d); 6.21 (1H, dd); 6.0 (1H, s); 5.46 (1H, d); 5.18 (1H, d); 4.87-4.83 (1H, m); 4.74 (1H, d); 4.50 (1H, t); 4.18 (1H, sb); 3.98-3.96 (2H, m); 2.71-2.31 (5H, m); 2.30-2.2 (3H, m); 2.10-1.77 (6H, m); 1.75-1.42 (7H, m); 1.4-1.32 (4H, m); 1.12 (3H, s); 0.85 (3H, s).

Example 4

Synthesis of (6α,11β,16α)-6,9-difluoro-11-hydroxy-16,17-((1-methylethylidene)bis(oxy))-21-[1-oxo-(2-((4-(nitrooxy)butyoxy-carbonylamino)acetyl)]-pregna-1,4-diene-3,20-dione

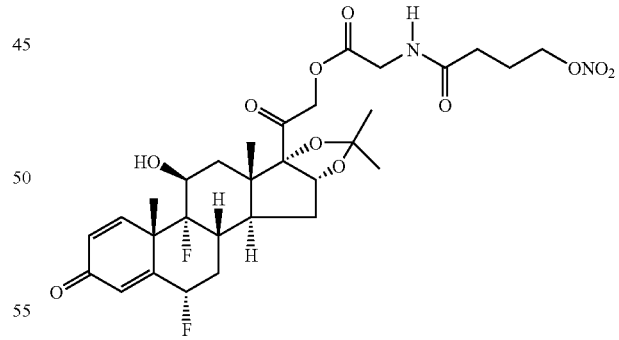

The compound was synthesized using the procedure described in example I starting from fluocinolone acetonide, Boc-glycine and 4-nitrooxybutyric acid pentafluorophenol ester.

$^1$H-NMR: (DMSO), δ: 8.43 (1H, t); 7.25 (1H, d); 6.28 (1H, dd); 6.09 (1H, s); 5.75-5.48 (2H, m); 5.18 (1H, d); 4.83 (1H, d); 4.78 (1H, d); 4.50 (2H, t); 4.18 (1H, sb); 3.9-3.8 (2H, m); 2.72-2.48 (4H, m); 2.25 (2H, t); 2.10-1.8 (3H, m); 1.78-1.65 (1H, m); 1.62-1.51 (2H, m); 1.48 (3H, s); 1.32 (3H, s); 1.10 (3H, s); 0.8 (3H, s).

Example 5

Synthesis of 4-(nitrooxy)butyl 2-acetamido-3-(4-((2-((9R,10S,11S,13S,16R,17S)-9-fluoro-11-hydroxy-16,17-((1-methylethylidene)bis(oxy))10,13-dimethyl-3-oxo-6,7,8,9,10,11,12,13,14,15,16,17-dodecahydro-3H-cyclopenta[a]phenanthren-17-yl)-2-oxoethoxy) carbonyloxy)phenyl)propanoate

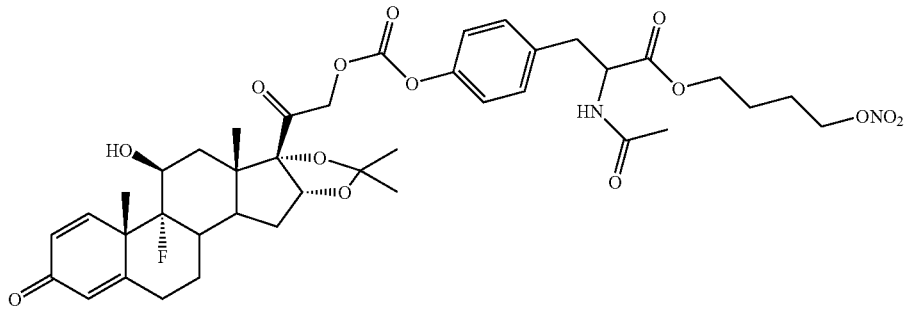

D) 4-(nitrooxy)butyl 2-(tert-butoxycarbonylamino)-3-(4-hydroxyphenyl)propanoate

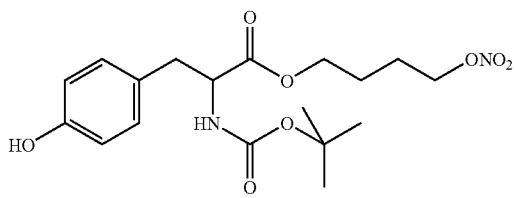

To a solution of Boc-(L)-tyrosine (5.0 g, 17.77 mmol) in N,N-dimethylformamide (40 ml) cesium carbonate (5.79 g, 17.77 mmol) was added. The reaction was cooled at 0° C. and a solution of 4-bromobutyl nitrate (17.77 mmol) in dichloromethane (20% w/w, 17.06 g) was added drop wise. The reaction was stirred at 0° C. for 20 minutes and then at room temperature for 22 hours. The mixture was poured into a 5% aqueous NaH$_2$PO$_4$ solution and extracted with diethyl ether (40×4 ml), the organic layers were dried over sodium sulfate and concentrated under reduced pressure. The residue was purified by flash chromatography, (Biotage System, column FLASH 65+M™ KP-Sil, eluent: gradient n-hexane/ethyl acetate 9/1 (500 ml), to n-hexane/ethyl acetate 1/1 during 4000 ml, n-hexane/ethyl acetate 1/1 (1000 ml)). The product (3.91 g) was obtained.

E) 4-(nitrooxy)butyl 2-amino-3-(4-hydroxyphenyl)propanoate

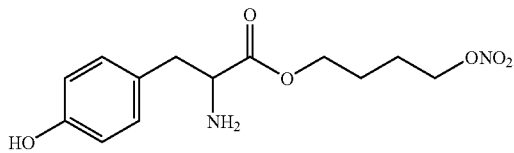

A solution of compound D (0.96 g, 2.41 mmol) in dichloromethane (20 ml) was stirred at room temperature. HCl gas was buddle in the solution for 3 hours. The mixture was diluted with dichloromethane (25 ml), washed with saturated aqueous sodium carbonate. The organic layer was dried over sodium sulfate and concentrated under reduced pressure. The product (0.71 g) was used in the next step without any purification.

F) 4-(nitrooxy)butyl 2-acetamido-3-(4-hydroxyphenyl)propanoate

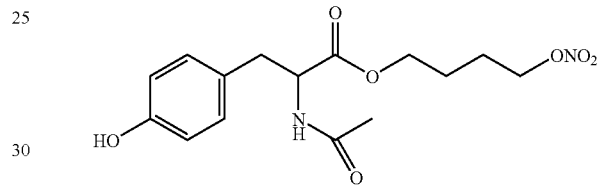

To a solution of compound E (0.63 g, 2.25 mmol) in dichloromethane (15 ml) triethylamine (0.31 ml, 2.25 mmol) was added. The reaction was cooled at 0° C. and acetyl chloride (0.17 ml, 2.48 mmol) was added drop wise. The reaction was stirred at 0° C. for 10 minutes and then at room temperature for 16 hours. The mixture was diluted with dichloromethane (25 ml), washed with water. The organic layer was dried over sodium sulfate and concentrated under reduced pressure. The residue was purified by flash chromatography, (Biotage System, column FLASH 25+M™ KP-Sil, eluent: gradient n-hexane/ethyl acetate 9/1 (100 ml), to n-hexane/ethyl acetate 2/8 during 1200 ml). The product (0.54 g) was obtained.

G) 4-(nitrooxy)butyl 2-acetamido-3-(4-((4-nitrophenoxy)carbonyloxy)phenyl)propanoate

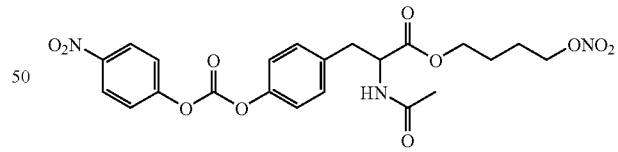

To a solution of compound F (0.54 g, 1.58 mmol) in dichloromethane (8 ml) pyridine (0.15 ml, 1.58 mmol) was added. The reaction was cooled at 0° C. and p-nitrophenylchloroformate (320 mg, 1.58 mmol) was added. The reaction was stirred at 0° C. for 15 minutes and then at room temperature for 48 hours. The mixture was diluted with dichloromethane (25 ml), washed with 1M aqueous HCl solution and then with saturated aqueous sodium carbonate. The organic layers was dried over sodium sulfate and concentrated under reduced pressure. The residue was purified by flash chromatography, (Biotage System, column FLASH 25+M™ KP-Sil, eluent: gradient n-hexane/ethyl acetate 9/1 (150 ml), to n-hexane/ethyl acetate 3/7 during 1200 ml, n-hexane/ethyl acetate 3/7 (600 ml)). The product (0.59 g) was obtained.

H) 4-(nitrooxy)butyl 2-acetamido-3-(4-((2-((9R,10S, 11S,13S,16R,17S)-9-fluoro-11-hydroxy-16,17-((1-methylethylidene)bis(oxy))10,13-dimethyl-3-oxo-6, 7,8,9,10,11,12,13,14,15,16,17-dodecahydro-3H-cyclopenta[a]phenanthren-17-yl)-2-oxoethoxy) phenyl)propanoate

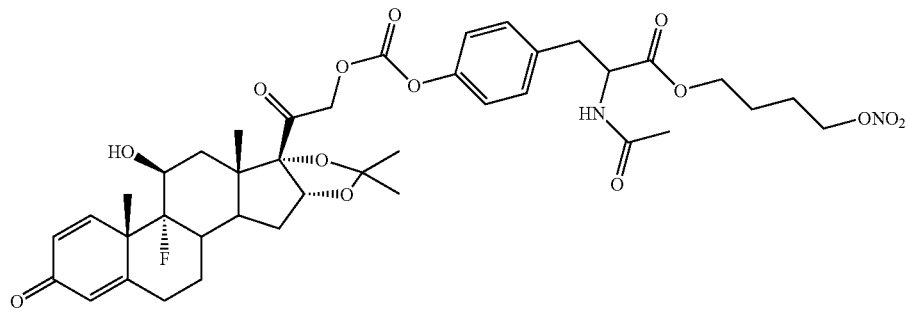

To a solution of compound G (0.55 g, 1.09 mmol) in dichloromethane (12 ml), scandium triflate (0.05 g, 0.11 mmol) and DMAP (0.26 g, 2.19 mmol) were added. The reaction was cooled at 0° C. and triamcinolone acetonide (0.47 g, 1.09 mmol) was added. The reaction was stirred at room temperature for 18 hours. The mixture was diluted with dichloromethane (24 ml), washed with 5% NaH$_2$PO$_4$ and then with saturated aqueous sodium carbonate. The organic layer was dried over sodium sulfate and concentrated under reduced pressure. The residue was purified by flash chromatography, (Biotage System, column FLASH 25+M™ KP-Sil, eluent: gradient n-hexane/ethyl acetate 9/1 (150 ml), to n-hexane/ethyl acetate 2/8 during 1200 ml, n-hexane/ethyl acetate 2/8 (800 ml)). The product (0.29 g) was obtained.

$^1$H-NMR: (DMSO), δ: 8.36 (1H, d); 7.37-7.32 (3H, m); 7.21-7.12 (2H, m); 6.23 (1H, dd); 6.02 (1H, s); 5.47 (1H, d); 5.31 (1H, d); 4.97-4.87 (2H, m); 4.59-4.48 (3H, m); 4.27-4.17 (1H, sb); 4.11-3.97 (2H, m); 3.10-2.90 (1H, m); 2.71-2.29 (4H, m); 2.10-1.75 (5H, m); 1.60-1.40 (7H, m); 1.38 (3H, s); 1.12 (3H, s); 0.80 (3H, s).

Example 6

Synthesis of (2S)-4-(nitrooxy)butyl 2-acetamido-3-(4-((2-((6S,9R,10S,11S,13S,16R,17S)-6,9-difluoro-11-hydroxy-16,17-((1-methylethylidene)bis(oxy))-10,13-dimethyl-3-oxo-6,7,8,9,10,11,12,13,14,15,16, 17-dodecahydro-3H-cyclopenta[a]phenanthren-17-yl)-2-oxoethoxy)carbonyloxy)phenyl)propanoate

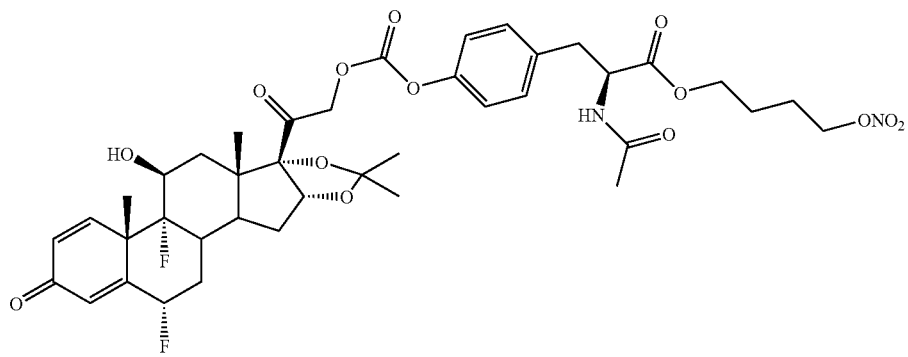

The compound was synthesized using the procedure described in example 5 starting from fluocinolone acetonide and compound G.

$^1$H-NMR: (DMSO), δ: 8.36 (1H, d); 7.28 (3H, m); 7.09 (2H, m); 6.30 (1H, dd); 6.11 (1H, d); 5.56 (1H, d); 5.31 (1H, d); 4.91 (2H, m); 4.50 (2H, t); 4.93 (1H, m); 4.25 (1H, m); 4.02 (3H, t); 2.96 (2H, m); 2.27 (1H, m); 2.01 (3H, m); 1.90-1.25 (17H, m); 1.15 (3H, s); 0.80 (3H, s).

Example 7

Synthesis of (2S)-4-(nitrooxy)butyl 2-amino-3-(4-((2-((9R,10S,11S,13S,16R,17S)-9-fluoro-11-hydroxy-16,17-((1-methylethylidene)bis(oxy))-10,13-dimethyl-3-oxo-6,7,8,9,10,11,12,13,14,15,16,17-dodecahydro-3H-cyclopenta[a]phenanthren-17-yl)-2-oxoethoxy)carbonyloxy)phenyl)propanoate Hydrochloride

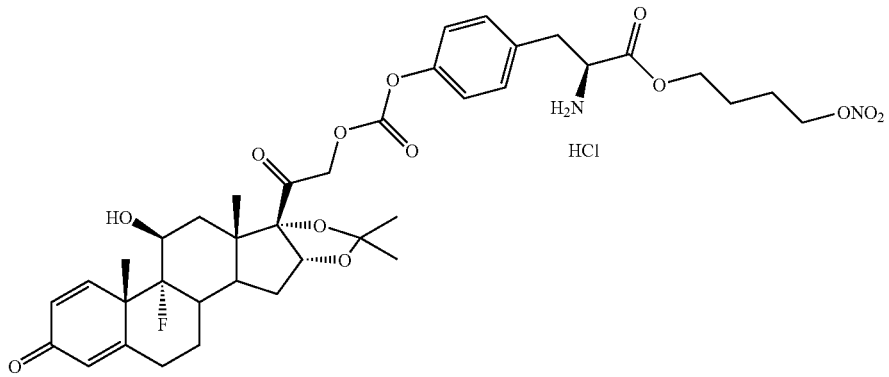

I) 4-hydroxybutyl 2-(tert-butoxycarbonylamino)-3-(4-((4-nitrophenoxy)carbonyloxy)phenyl)propanoate

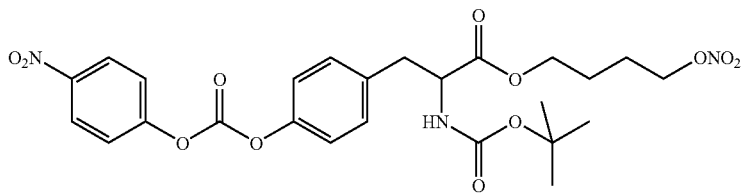

To a solution of compound D (1.97 g, 4.86 mmol) in dichloromethane (24 ml) pyridine (0.48 ml, 4.86 mmol) was added. The reaction was cooled at 0° C. and p-nitrophenylchloroformate (980 mg, 4.86 mmol) was added. The reaction was stirred at 0° C. for 10 minutes and then at room temperature for 21 hours. The mixture was diluted with dichloromethane (25 ml), washed with 1M aqueous HCl solution and then with saturated aqueous sodium carbonate. The organic layers was dried over sodium sulfate and concentrated under reduced pressure. The residue was purified by flash chromatography, (Biotage System, column FLASH 40+M™ KP-Sil, eluent: gradient n-hexane/ethyl acetate 98/2 (200 ml), to n-hexane/ethyl acetate 6/4 during 1600 ml, n-hexane/ethyl acetate 6/4 (300 ml)). The product (2.19 g) was obtained.

J) (2S)-4-(nitrooxy)butyl 2-(tert-butoxycarbonylamino)-3-(4-((2-((9R,10S,11S,13S,16R,17S)-9-fluoro-11-hydroxy-16,17-((1-methylethylidene)bis(oxy))-10,13-dimethyl-3-oxo-6,7,8,9,10,11,12,13,14,15,16,17-dodecahydro-3H-cyclopenta[a]phenanthren-17-yl)-2-oxoethoxy)carbonyloxy)phenyl)propanoate

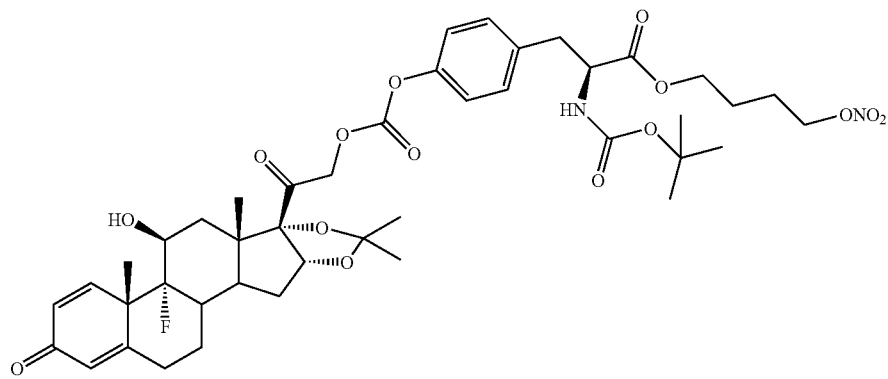

To a solution of compound I (1.35 g, 2.4 mmol) in dichloromethane (40 ml), scandium triflate (0.11 g, 0.24 mmol) and DMAP (0.57 g, 4.8 mmol) were added. The reaction was cooled at 0° C. and triamcinolone acetonide (1.25 g, 2.88 mmol) was added. The reaction was stirred at room temperature for 70 hours. The solvent was evaporated under reduced pressure. The residue was purified by flash chromatography, (Biotage System, column FLASH 40+M™ KP-Sil, eluent: gradient n-hexane/ethyl acetate 9/1 (200 ml), to n-hexane/ethyl acetate 3/7 during 1600 ml, n-hexane/ethyl acetate 3/7 (500 ml)). The product (0.98 g) was obtained.

K) (2S)-4-(nitrooxy)butyl-2-amino-3-(4-((2-((9R,10S,11S,13S,16R,17S)-9-fluoro-11-hydroxy-16,17-((1-methylethylidene)bis(oxy))-10,13-dimethyl-3-oxo-6,7,8,9,10,11,12,13,14,15,16,17-dodecahydro-3H-cyclopenta[a]phenanthren-17-yl)-2-oxoethoxy)carbonyloxy)phenyl)propanoate Hydrochloride

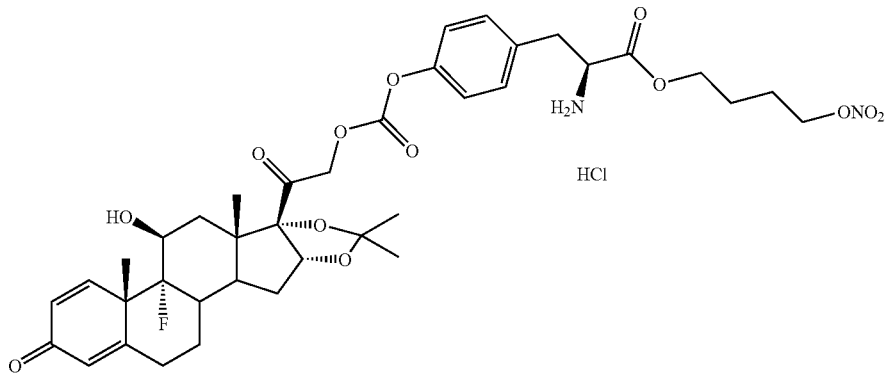

A solution of compound J (1.42 g, 1.65 mmol) in dichloromethane (28 ml) was stirred at room temperature. HCl gas was buddle in the solution for 15 minutes. The mixture was diluted with dichloromethane (35 ml), washed with saturated aqueous sodium carbonate. The organic layer was dried over sodium sulfate and concentrated under reduced pressure. The residue was purified by reverse-phase flash chromatography, (Biotage System, column FLASH 40+M™ KP-Sil, eluent: gradient water/acetonitrile 9/1 (150 ml), to water/acetonitrile 2/8 during 1400 ml, water/acetonitrile 2/8 (200 ml)). The free base of product M (0.67 g) was treated with a solution of HCl in diethyl ether. The hydrochloride salt of compound M was filtered and dried under vacuum. The product (0.57 g) was obtained.

$^1$H-NMR: (DMSO), δ: 8.57 (2H, m); 7.38-7.29 (3H, m); 7.22-7.19 (2H, m); 6.22 (1H, dd); 6.00 (1H, s); 5.54 (1H, d); 5.31 (1H, d); 4.88-4.84 (2H, m); 4.52-4.40 (2H, m); 4.25-4.20 (1H, sb); 4.16-4.09 (3H, m); 3.22-3.04 (1H, m); 2.71-2.29 (4H, m); 2.10-1.75 (5H, m); 1.60-1.34 (7H, m); 1.13 (3H, s); 0.82 (3H, s).

Example 8

Synthesis of (2S)-4-(nitrooxy)butyl 2-amino-3-(4-((2-((6S,9R,10S,11S,13S,16R,17S)-6,9-difluoro-11-hydroxy-16,17-((1-methylethylidene)bis(oxy))-10,13-dimethyl-3-oxo-6,7,8,9,10,11,12,13,14,15,16,17-dodecahydro-3H-cyclopenta[a]phenanthren-17-yl)-2-oxoethoxy)carbonyloxy)phenyl)propanoate Hydrochloride

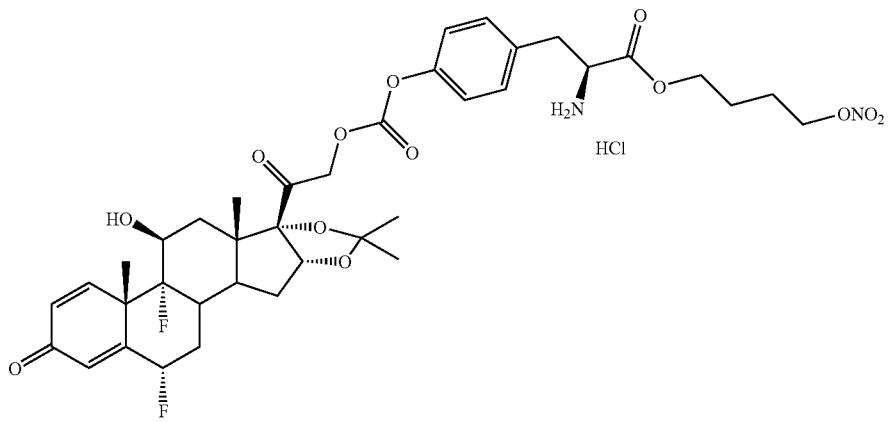

The compound was synthesized using the procedure described in example 7 starting from fluocinolone acetonide and compound ¹H-NMR: (DMSO), δ: 8.64 (2H, s); 7.41-7.35 (3H, m); 7.23 (2H, d); 6.30 (1H, dd); 6.11 (1H, s); 5.80-5.50 (2H, m); 5.40-5.27 (1H, m); 5.00-4.75 (2H, m); 4.53-4.45 (2H, m); 4.48-4.05 (4H, m); 3.31-3.03 (2H, m); 2.75-2.60 (1H, m); 2.27 (1H, sb); 2.11-1.98 (3H, m); 1.82-1.52 (5H, m); 1.50 (3H, s); 1.38 (3H, s); 1.10 (3H, s); 0.81 (3H, s).

Example 9

Synthesis of 2-((8S,9R,10S,11S,13S,14S,16R,17S)-9-fluoro-11-hydroxy-16,17-(1-methyl ethylidenebis(oxy))-10,13-dimethyl-3-oxo-6,7,8,9,10,11,12,13,14,15,16,17-dodecahydro-3H-cyclopenta[a]phenanthren-17-yl)-2-oxoethyl-2-(5-(nitrooxy)pentanamido)acetate

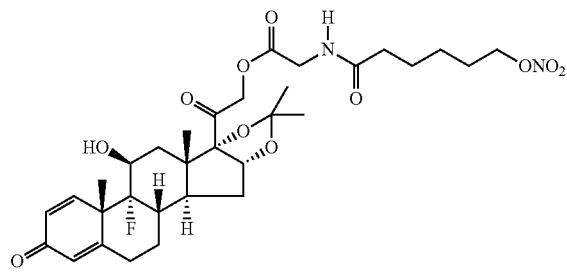

The compound was synthesized using the procedure described in example I starting from triamcinolone acetonide, Boc-glycine and 4-nitrooxybutyric acid pentafluorophenol ester.

¹H-NMR: (DMSO), δ: 7.29 (1H, d); 6.23 (1H, dd); 6.02 (1H, s); 5.48 (1H, d); 5.20 (1H, d); 4.86 (1H, m); 4.78 (1H, d); 4.50 (2H, t); 4.18 (1H, sb); 3.98-3.96 (2H, m); 2.71-2.25 (2H, m); 2.30 (5H, m); 1.75-1.42 (14H, m); 1.4-1.32 (4H, m); 1.12 (3H, s); 0.83 (3H, s).

Example 10

Synthesis of 2-((8S,9R,10S,11S,13S,14S,16S,17R)-9-fluoro-11,17-dihydroxy-10,13,16-trimethyl-3-oxo-6,7,8,9,10,11,12,13,14,15,16,17-dodecahydro-3H-cyclopenta[a]phenanthren-17-yl)-2-oxoethyl 2-(5-(nitrooxy)hexanamidoamido)acetate

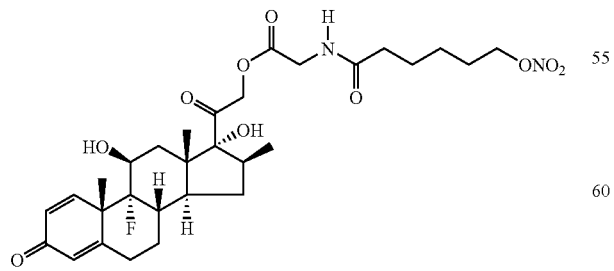

The compound was synthesized using the procedure described in example I starting from betamethasone, Boc-glycine and 6-nitrooxyhexanoic acid pentafluorophenol ester.

¹H-NMR: (DMSO), δ: 8.28 (1H, t); 7.27 (1H, d); 6.15 (1H, dd); 5.99 (1H, s); 5.35 (1H, s); 5.27 (1H, d); 4.99 (1H, d), 4.79 (1H, d); 4.48 (2H, t), 4.11 (1H, m); 3.91 (2H, d); 2.60 (1H, m); 2.50-2.30 (2H, m); 2.10 (4H, m); 2.00-1.80 (3H, m); 1.70-1.30 (11H, m); 1.00 (4H, d); 0.99 (3H, s).

Example 11

Synthesis of 2-((6S,8S,9R,10S,11S,13S,14S,16R,17S)-6,9-difluoro-11-hydroxy-16,17-dimethoxy-10,13-dimethyl-3-oxo-6,7,8,9,10,11,12,13,14,15,16,17-dodecahydro-3H-cyclopenta[a]phenanthren-17-yl)-2-oxoethyl 2-(6-nitrooxy hexanamido)acetate

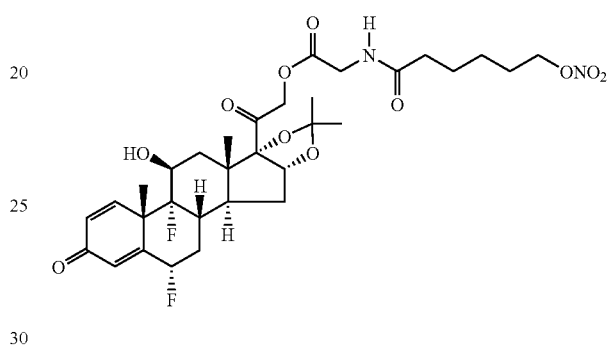

The compound was synthesized using the procedure described in example I starting from fluocinolone acetonide, Boc-glycine and 6-nitrooxyhexanoic acid pentafluorophenol ester.

¹H-NMR: (DMSO), δ: 8.32 (1H, t); 7.25 (1H, d); 6.28 (1H, dd); 6.09 (1H, s); 5.74-5.50 (2H, m); 5.18 (1H, d); 4.85 (1H, w d); 4.78 (1H, d); 4.48 (2E, t); 4.19 (18, sb); 3.94 (2H, m); 2.63-2.48 (1H, m); 2.25 (1H, t); 2.13 (2H, t); 2.10-1.93 (2H, m); 1.73-1.40 (11H, m); 1.30 (5H, m); 1.10 (3H, s); 0.8 (3H, s).

Example 12

Synthesis of 1-(2-((8S,9R,10S,11S,13S,14S,16R,17S)-9-fluoro-11-hydroxy-16,17-((1-methyl-ethylidene)bis(oxy))-10,13-dimethyl-3-oxo-6,7,8,9,10,11,12,13,14,15,16,17-dodecahydro-3H-cyclopenta[a]phenanthren-17-yl)-2-oxoethyl)-1-(4-(nitrooxy)butyl) 2-acetamido Pentanedioate

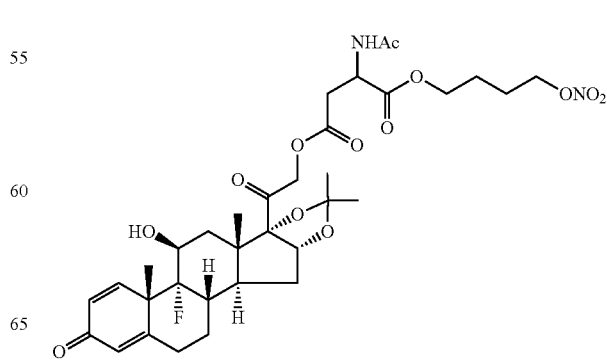

L) 2-acetamido-4-(2-((8S,9R,10S,11S,13S,14S,16R, 17S)-9-fluoro-11-hydroxy-16,17-((1-methylethylidene)bis(oxy))-10,13-dimethyl-3-oxo-6,7,8,9,10, 11,12,13,14,15,16,17-dodecahydro-3H-cyclopenta[a] phenanthren-17-yl)-2-oxoethoxy)-4-oxobutanoic Acid

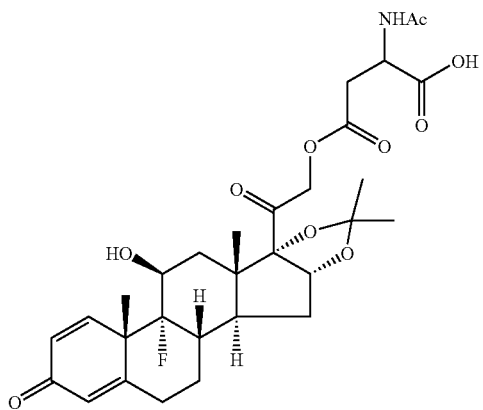

To a solution of triamcinolone acetonide (3.1 g, 7.13 mmol) in acetone (100 ml), N-acetyl aspartic acid (2.0 g, 11.42 mmol) and DMAP (cat. amount) were added. The reaction was cooled at 0° C. and EDAC (2.18 g, 11.42 mmol) was added. The reaction was stirred at room temperature for 24 hours. The solvent was evaporated under vacuum. The residue was purified by flash chromatography (Biotage System, column FLASH 65+M™ KP-Sil, eluent: gradient dichloromethane/methanol 95/5 (675 ml), to dichloromethane/methanol 9/1 during 3600 ml, dichloromethane/methanol 9/1 (900 ml)). The product (2.67 g) was obtained.

M) 1-(4-chlorobutyl) 4-(2-((8S,9R,10S,11S,13S,14S, 16R,17S)-9-fluoro-11-hydroxy-16,17-((1-methylethylidene)bis(oxy))-10,13-dimethyl-3-oxo-6,7,8,9,10, 11,12,13,14,15,16,17-dodecahydro-3H-cyclopenta[a] phenanthren-17-yl)-2-oxoethyl)-2-acetamido succinate

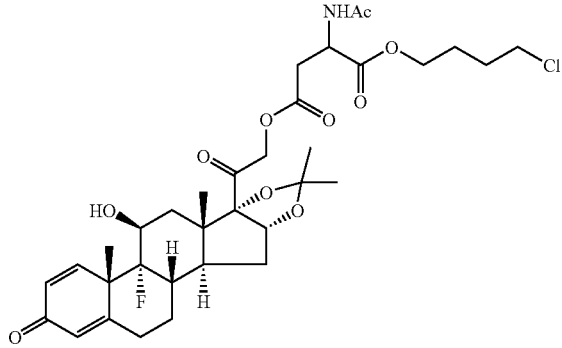

To a solution of compound L (0.6 g, 1.31 mmol) in dichloromethane (30 ml), 4-chlorobutanol (0.13 ml, 1.31 mmol) and DMAP (cat. amount) were added. The reaction was cooled at 0° C. and EDAC (0.25 g, 1.31 mmol) was added. The reaction was stirred at room temperature for 24 hours. The solvent was evaporated under vacuum. The residue was purified by flash chromatography (Biotage System, column FLASH 25+M™ KP-Sil, eluent: gradient n-hexane/ethyl acetate 6/4 (60 ml), to n-hexane/ethyl acetate 2/8 during 600 ml, to ethyl acetate during 60 ml, ethyl acetate (180 ml)). The product (0.65 g) was obtained.

N) 1-(4-iodobutyl) 4-(2-((8S,9R,10S,11S,13S,14S, 16R,17S)-9-fluoro-11-hydroxy-16,17-((1-methylethylidene)bis(oxy))-10,13-dimethyl-3-oxo-6,7,8,9,10, 11,12,13,14,15,16,17-dodecahydro-3H-cyclopenta[a] phenanthren-17-yl)-2-oxoethyl)-2-acetamido succinate

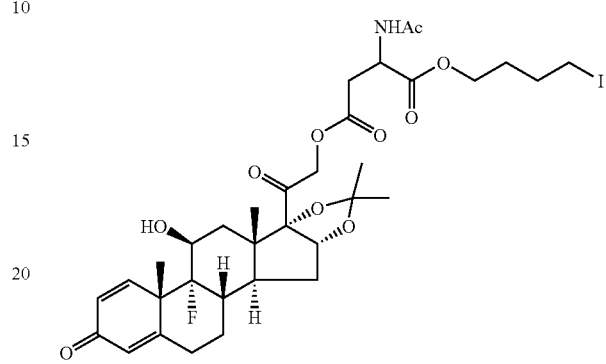

To a solution of compound M (0.55 g, 0.76 mmol) in acetonitrile (18 ml), sodium iodide (0.45 g, 3.06 mmol) was added. The reaction was heated to 120° C. for 60 minutes under microwave irradiation. The resulting mixture was cooled, filtered and the solvent was removed under reduced pressure to give a solid product which was used without further purification.

O) 1-(2-((8S,9R,10S,11S,13S,14S,16R,17S)-9-fluoro-11-hydroxy-16,17-((1-methylethylidene)bis (oxy))-10,13-dimethyl-3-oxo-6,7,8,9,10,11,12,13,14, 15,16,17-dodecahydro-3H-cyclopenta[a] phenanthren-17-yl)-2-oxoethyl)-1-(4-(nitrooxy) butyl)-2-acetamido Pentanedioate

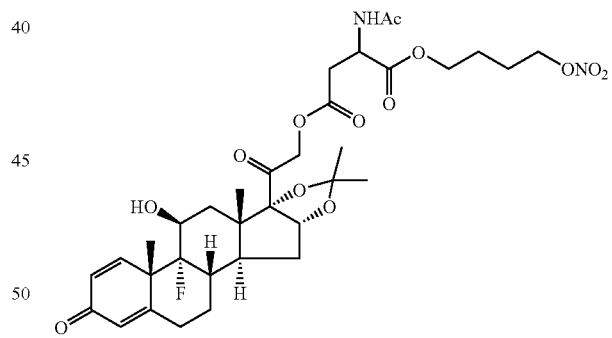

To a solution of compound N (0.60 g, 0.76 mmol) in acetonitrile (20 ml), silver nitrate (0.51 g, 3.06 mmol) was added. The reaction was heated to 120° C. for 5 minutes under microwave irradiation. The resulting mixture was cooled, filtered and the solvent was removed under reduced pressure. The residue was purified by flash chromatography (Biotage System, column FLASH 25+M™ KP-Sil, eluent: gradient n-hexane/ethyl acetate 4/6 (60 ml), to ethyl acetate 100% during 480 ml, ethyl acetate (120 ml)). The product (0.40 g) was obtained.

$^1$H-NMR: (DMSO): 8.45 (1H, d); 7.26 (1H, d); 6.22 (1H, dd); 6.00 (1H, s); 5.48 (1H, m); 5.12 (1H, dd), 4.84-4.76 (3H, m); 4.52 (2H, t); 4.20 (1H, m), 4.06 (2H, m); 2.87 (1H, dm); 2.75-2.48 (3H, m); 2.10-1.75 (4H, m); 1.82 (3H, s); 1.50-1.70 (7H, m); 1.47 (3H, s); 1.33 (4H, m); 1.15 (3H, s); 0.83 (3H, s).

Example 13

Synthesis of 2-((8S,9R,10S,11S,3S,14S,16S,17R)-9-fluoro-11,17-dihydroxy-10,13,16-trimethyl-3-oxo-6,7,8,9,10,11,12,13,14,15,16,17-dodecahydro-3H-cyclopenta[a]phenanthren-17-yl)-2-oxoethyl 3-(6-(nitrooxy)hexanamido) propanoate

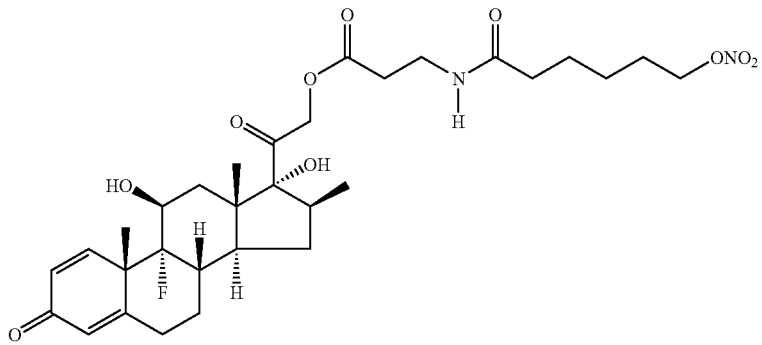

The compound was synthesized using the procedure described in example 1 starting from betamethasone, Boc-beta-alanine and 6-nitrooxyhexanoic acid pentafluorophenol ester.

$^1$H-NMR: (DMSO), δ: 7.88 (1H, t); 7.29 (1H, d); 6.22 (1H, dd); 6.01 (1H, s); 5.36 (1H, s); 5.31 (1H, d); 5.01 (1H, d); 4.84 (1H, d); 4.50 (2H, t); 4.15 (1H, sb); 3.48-3.25 (2H, m); 2.75-2.25 (7H, m); 2.20-2.00 (4H, m); 1.99-1.75 (4H, m); 1.71-1.61 (2H, m); 1.57-1.48 (5H, m); 1.42-1.27 (2H, m); 1.01 (3H, d); 0.90 (3H, s).

Example 14

Synthesis of 2-((8S,9R,10S,11S,13S,14S,16R,17S)-9-fluoro-11-hydroxy-16,17-dimethoxy-10,13-((1-methyl ethylidene)bis(oxy))-3-oxo-6,7,8,9,10,11,12,13,14,15,16,17-dodecahydro-3H-cyclopenta[a]phenanthren-17-yl)-2-oxoethyl-3-(6-(nitrooxy)hexanamido) Propanoate

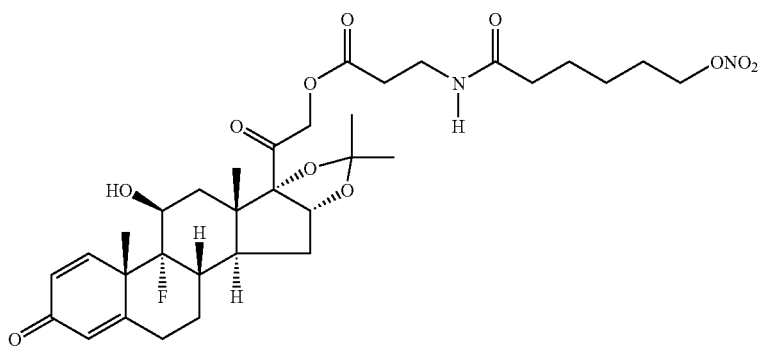

The compound was synthesized using the procedure described in example I starting from triamcinolone acetonide, Boc-beta- and 6-nitrooxyhexanoic acid pentafluorophenol ester.

$^1$H-NMR: (DMSO), δ: 8.31 (1H, t); 7.30 (1H, d); 6.24 (1H, dd); 6.01 (1H, s); 5.49 (1H, d); 5.25 (1H, d); 4.86 (1H, d); 4.75 (1H, d); 4.50 (2H, t); 4.19 (1H, sb); 3.93 (2H, m); 2.75-2.25 (2H, m); 2.15 (2H, t); 2.10-1.75 (3H, m); 1.75-1.45 (7H, m); 1.47 (3H, s); 1.40-1.20 (6H, m); 1.17 (5H, m); 0.80 (3H, s).

Example 15

Synthesis of 2-((6S,8S,9R,10S,11S,13S,14S,16R,17S)-6,9-difluoro-11-hydroxy-16,17-((1-methylethylidene)bis(oxy))-10,13-dimethyl-3-oxo-6,7,8,9,10,11,12,13,14,15,16,17-dodecahydro-3H-cyclopenta[a]phenanthren-17-yl)-2-oxoethyl-3-(6-(nitrooxy)hexanamido) Propanoate

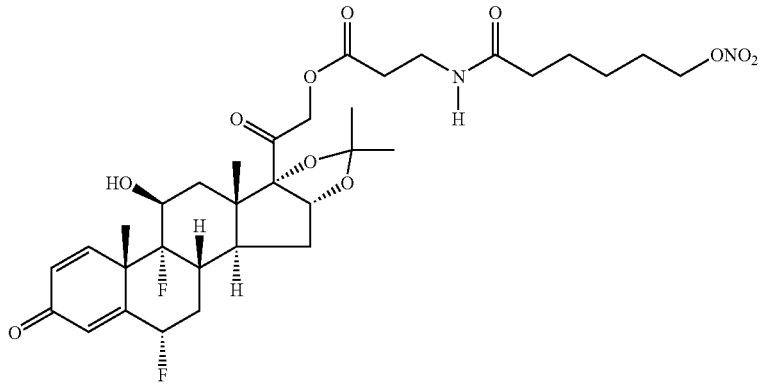

The compound was synthesized using the procedure described in example I starting from fluocinolone acetonide, Boc-beta-alanine and 6-nitrooxyhexanoic acid pentafluorophenol ester.

$^1$H-NMR: (DMSO), δ: 7.91 (1H, t); 7.27 (1H, d); 6.30 (1H, dd); 6.11 (1H, s); 5.75-5.50 (2H, m); 5.16 (1H, d); 4.85-4.90 (1H, m); 4.76 (1H, d); 4.61-4.48 (2H, t); 4.22 (1H, sb); 3.40-3.25 (3H, m); 2.70-2.50 (4H, m); 2.40-2.30 (1H, m); 2.15-1.93 (2H, m); 1.80-1.45 (10H, m); 1.41-1.28 (5H, m); 1.21 (3H, s); 0.82 (3H, s).

Example 16

Synthesis of 4-(2-((8S,9R,10S,11S,13S,14S,16R,17S)-9-fluoro-11-hydroxy-16,17-((1-methylethylidene)bis(oxy))-10,13-dimethyl-3-oxo-6,7,8,9,10,11,12,13,14,15,16,17-dodecahydro-3H-cyclopenta[a]phenanthren-17-yl)-2-oxoethyl)-1-(4-(nitrooxy)butyl)2-(6-(nitrooxy)hexanamido)succinate

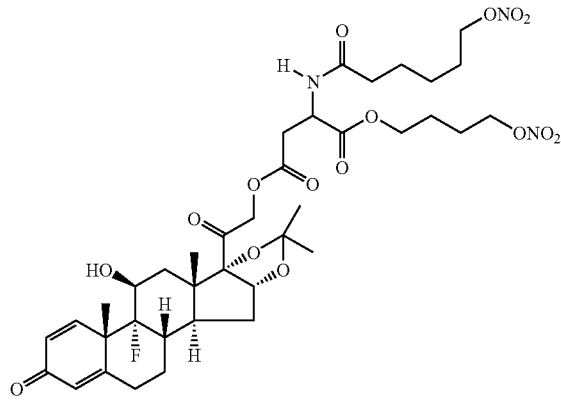

P) 1-allyl 4-(2-((8S,9R,10S,11S,13S,14S,16R,17S)-9-fluoro-11-m hydroxy-16,17-((1-methylethylidene)bis(oxy))-10,13-dimethyl-3-oxo-6,7,8,9,10,11,12,13,14,15,16,17-dodecahydro-3H-cyclopenta[a]phenanthren-17-yl)-2-oxoethyl)-2-(tert-butoxycarbonyl amino)succinate

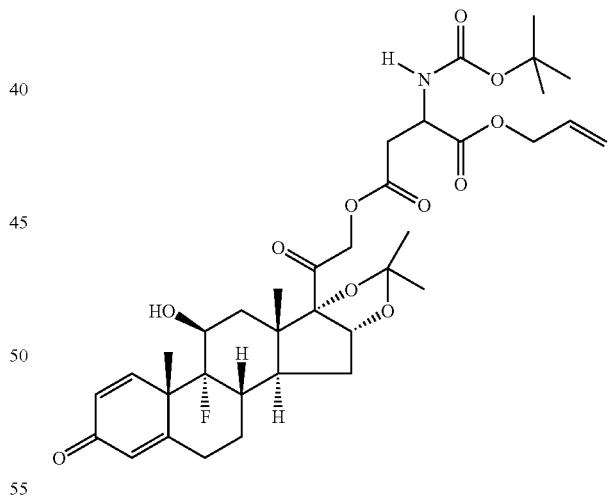

To a solution of triamcinolone acetonide (3.0 g, 6.9 mmol) in dichloromethane (100 ml), 4-(allyloxy)-3-(tert-butoxycarbonylamino)-4-oxobutanoic acid (1.88 g, 6.9 mmol) and DMAP (cat. amount) were added. The reaction was cooled at 0° C. and EDAC (1.7 g, 8.97 mmol) was added. The reaction was stirred at room temperature for 12 hours. The solvent was evaporated under vacuum. The residue was purified by flash chromatography (Biotage System, column FLASH 40+M™ KP-Sil, eluent: gradient n-hexane/ethyl acetate 8/2 (300 ml), to n-hexane/ethyl acetate 4/6 during 900 ml, n-hexane/ethyl acetate 4/6 (300 ml)). The product (4.16 g) was obtained.

Q) 1-allyl 4-(2-((8S,9R,10S,11S,13S,14S,16R,17S)-9-fluoro-11-hydroxy-16,17-((1-methylethylidene)bis(oxy))-10,13-dimethyl-3-oxo-6,7,8,9,10,11,12,13,14,15,16,17-dodecahydro-3H-cyclopenta[a]phenanthren-17-yl)-2-oxoethyl)-2-(amino)succinate Hydrochloride

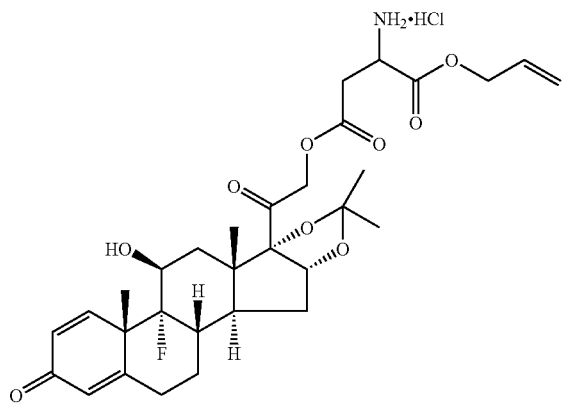

A solution of compound P (1.0 g, 1.45 mmol) in dichloromethane (28 ml) was stirred at room temperature. HCl gas was buddle in the solution for 15 minutes. The solvent evaporated under vacuum to give a solid product which was used without further purification.

R) 1-allyl 4-(2-((8S,9R,10S,11S,13S,14S,16R,17S)-9-fluoro-11-hydroxy-16,17-((1-methylethylidene)bis(oxy))-10,13-dimethyl-3-oxo-6,7,8,9,10,11,12,13,14,15,16,17-dodecahydro-3H-cyclopenta[a]phenanthren-17-yl)-2-oxoethyl)-2-(6-(nitrooxy)hexanamido) Succinate

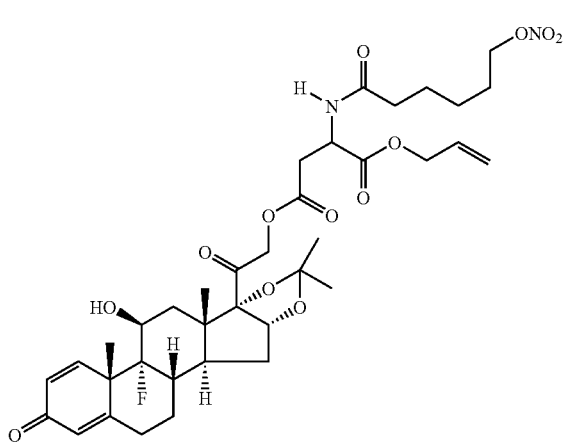

To a solution of compound Q (0.91 g, 1.45 mmol) in dichloromethane (100 ml), DMAP (0.26 g, 2.17 mmol) and 6-nitrooxyhexanoic acid pentafluorophenol ester (0.49 g, 1.45 mmol) were added. The reaction was stirred at room temperature for 12 hours. The solvent was evaporated under reduced pressure. The residue was purified by flash chromatography, (Biotage System, column FLASH 40+M™ KP-Sil, eluent: gradient n-hexane/ethyl acetate 1/1 (150 ml), to ethyl acetate during 900 ml, ethyl acetate (450 ml)). The product (0.64 g) was obtained.

S) 4-(2-((8S,9R,10S,11S,13S,14S,16R,17S)-9-fluoro-11-hydroxy-16,17-((1-methylethyl idene)bis(oxy))-10,13-dimethyl-3-oxo-6,7,8,9,10,11,12,13,14,15,16,17-dodecahydro-3H-cyclopenta[a]phenanthren-17-yl)-2-oxoethyl)-2-(6-(nitrooxy)hexanamido)-4-oxobutanoic Acid

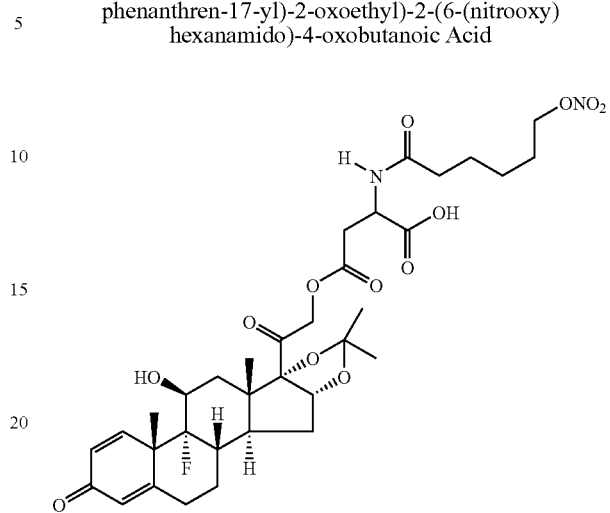

To a solution of compound R (0.58 g, 0.77 mmol) in dichloromethane (20 ml), 5,5-cimethyl-1,3-cyclohexanedione (0.13 g, 0.97 mmol), triphenylphosphine (0.30 g, 1.16 mmol) and tetrakis(triphenylphosphine)palladium (0.045 g, 0.039 mmol) were added. The reaction was stirred at room temperature for 12 hours. The solvent was evaporated under reduced pressure. The residue was purified by flash chromatography, (Biotage System, column FLASH 40+M™ KP-Sil, eluent: n-hexane/acetone/acetic acid 4/6/0.1%) The product (0.31 g) was obtained.

T) 4-(2-((8S,9R,10S,11S,13S,14S,16R,17S)-9-fluoro-11-hydroxy-16,17-((1-methylethylidene)bis(oxy))-10,13-dimethyl-3-oxo-6,7,8,9,10,11,12,13,14,15,16,17-dodecahydro-3H-cyclopenta[a]phenanthren-17-yl)-2-oxoethyl)-1-(4-(chloro)butyl)2-(6-(nitrooxy)hexanamido)succinate

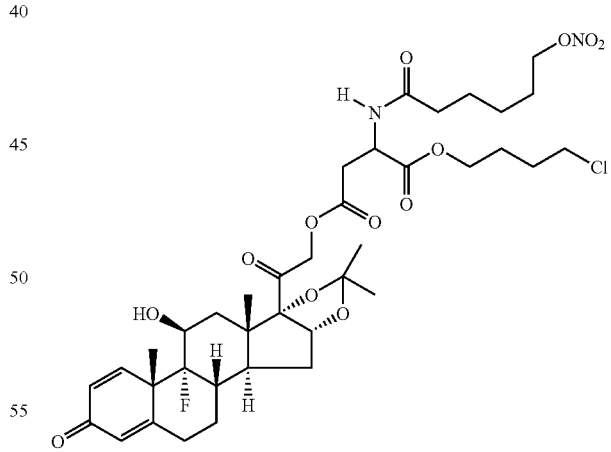

To a solution of compound S (0.33 g, 0.47 mmol) in dichloromethane (20 ml), 4-chlorobutanol (0.06 ml, 0.61 mmol) and DMAP (cat. amount) were added. The reaction was cooled at 0° C. and EDAC (0.12 g, 0.62 mmol) was added. The reaction was stirred at room temperature for 24 hours. The solvent was evaporated under vacuum. The residue was purified by flash chromatography (Biotage System, column FLASH 25+M™ KP-Sil, eluent: gradient n-hexane/ethyl acetate 6/4 (60 ml), to n-hexane/ethyl acetate 2/8 during 360 ml, n-hexane/ethyl acetate 2/8 (240 ml)). The product (0.25 g) was obtained.

U) 4-(2-((8S,9R,10S,11S,13S,14S,16R,17S)-9-fluoro-11-hydroxy-16,17-((1-methylethylidene)bis(oxy))-10,13-dimethyl-3-oxo-1-(4-(iodo)butyl) 2-(6-(nitrooxy)hexanamido)succinate

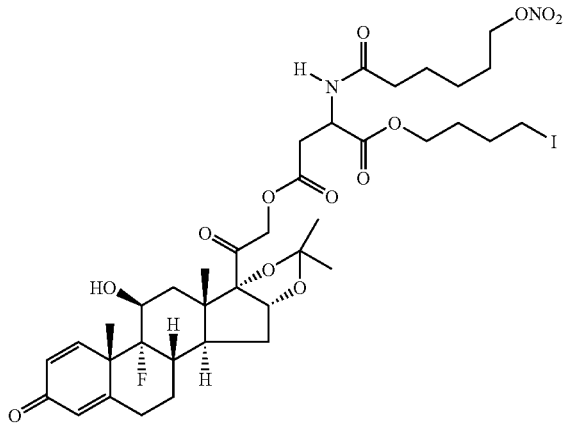

To a solution of compound T (0.25 g, 0.31 mmol) in acetonitrile (10 ml), sodium iodide (0.18 g, 1.25 mmol) was added. The reaction was heated to 120° C. for 60 minutes under microwave irradiation. The resulting mixture was cooled, filtered and the solvent was removed under reduced pressure to give a solid product which was used without further purification.

V) 4-(2-((8S,9R,10S,11S,13S,14S,16R,17S)-9-fluoro-11-hydroxy-16,17-((1-methylethylidene)bis(oxy))-10,13-dimethyl-3-oxo-6,7,8,9,10,11,12,13,14,15,16,17-dodecahydro-3H-cyclopenta[a]phenanthren-17-yl)-2-oxoethyl)-1-(4-(nitrooxy)butyl)2-(6-(nitrooxy)hexanamido)succinate

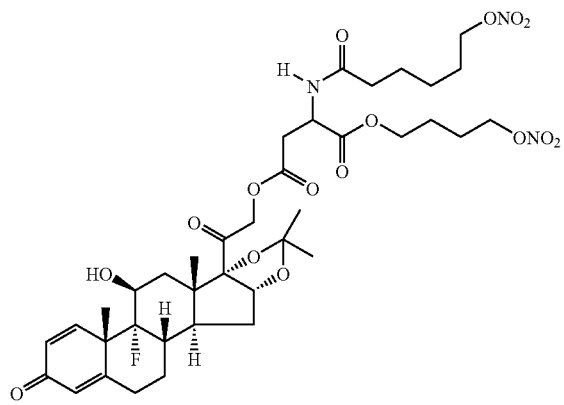

To a solution of compound U (0.27 g, 0.31 mmol) in acetonitrile (10 ml), silver nitrate (0.21 g, 1.24 mmol) was added. The reaction was heated to 120° C. for 5 minutes under microwave irradiation. The resulting mixture was cooled, filtered and the solvent was removed under reduced pressure. The residue was purified by flash chromatography (Biotage System, column FLASH 25+M™ KP-Sil, eluent: gradient n-hexane/acetone 8/2 (120 ml), to n-hexane/acetone 55/45 during 480 ml, n-hexane/acetone 55/45 (120 ml)). The product (0.13 g) was obtained.

$^{1}$H-NMR: (DMSO), δ: 7.18 (1H, d); 6.59 (1H, d); 6.32 (1H, dd); 6.13 (1H, s); 5.02-4.88 (4H, m); 4.51-4.40 (5H, m); 4.27-4.11 (2H, m); 3.05 (1H, dd); 2.90 (1H, dd); 2.68-2.30 (4H, m); 2.27 (2H, t); 2.27-2.00 (2H, m); 1.90-1.40 (18H, m); 1.21 (3H, s); 0.88 (3H, s).

Example 17

Synthesis of 1-(2,3-bis(nitrooxy)propyl)4-(2-((9R,10S,11S,13S,16R,17S)-9-fluoro-11-hydroxy-16,17-((1-methylethylidene)bis(oxy))-10,13-dimethyl-3-oxo-6,7,8,9,10,11,12,13,14,15,16,17-dodecahydro-3H-cyclopenta[a]phenanthren-17-yl)-2-oxoethyl)-2-aminosuccinate Hydrochloride

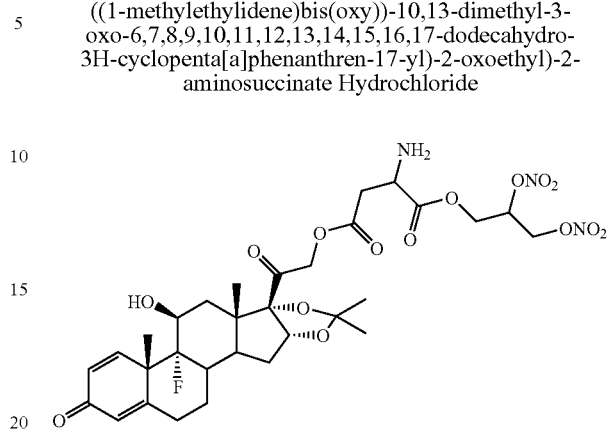

W) 1-allyl-4-(4-nitrophenyl)-2-(tert-butoxycarbonylamino) Succinate

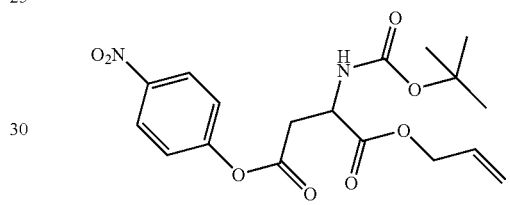

To a solution of 4-(allyloxy)-3-(tert-butoxycarbonylamino)-4-oxobutanoic acid (3.0 g, 11.0 mmol) in dichloromethane (50 ml), 4-nitrophenol (1.4 g, 11.0 mmol) and DMAP (cat. amount) were added. The reaction was cooled at 0° C. and EDAC (2.85 g, 15.0 mmol) was added. The reaction was stirred at room temperature for 12 hours. The solvent was evaporated under vacuum. The residue was purified by flash chromatography (Biotage System, column FLASH 65+M™ KP-Sil, eluent: gradient n-hexane/ethyl acetate 95/5 (450 ml), to n-hexane/ethyl acetate 6/4 during 4500 ml, n-hexane/ethyl acetate 6/4 (900 ml)). The product (1.5 g) was obtained.

X) 1-(2,3-bis(nitrooxy)propyl)4-(4-nitrophenyl)2-(tert-butoxycarbonylamino)succinate

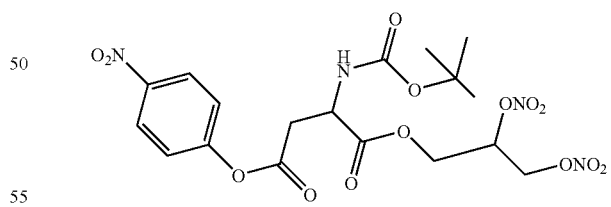

To a solution of compound W (1.5 g, 3.8 mmol) in acetonitrile (60 ml), silver nitrate (0.63 g, 3.8 mmol) was added. The reaction was cooled at −15° C. and iodine (0.96 g, 3.8 mmol) was added. The reaction was stirred at 0° C. for 1 hour. Silver nitrate (1.27 g, 7.6 mmol) was added and the mixture was stirred at 70° C. for 7 days adding silver nitrate (0.96 g, 3.8 mmol) every day. The solvent was evaporated under vacuum. The residue was purified by flash chromatography (Biotage System, column FLASH 65+M™ KP-Sil, eluent: gradient n-hexane/ethyl acetate 95/5 (450 ml), to n-hexane/ethyl acetate 6/4 during 4500 ml, n-hexane/ethyl acetate 6/4 (900 ml)). The product (0.54 g) was obtained.

Y) 1-(2,3-bis(nitrooxy)propyl)4-(2-((9R,10S,11S, 13S,16R,17S)-9-fluoro-11-hydroxy-16,17-((1-methylethylidene)bis(oxy))-10,13-dimethyl-3-oxo-6,7,8, 9,10,11,12,13,14,15,16,17-dodecahydro-3H-cyclopenta[a]phenanthren-17-yl)-2-oxoethyl)-2-(tert-butoxy carbonylamino)succinate

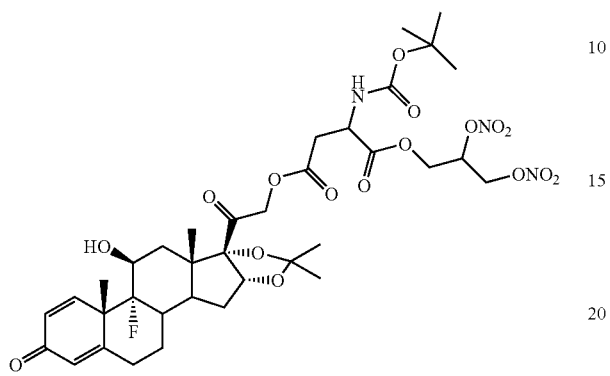

To a solution of triamcinolone acetonide (0.21 g, 0.5 mmol) in dichloromethane (13 ml), compound X (0.26 g, 0.5 mmol) and DMAP (0.06 g, 0.5 mmol)) were added. The reaction was stirred at room temperature for 12 hours. The solvent was evaporated under vacuum. The residue was purified by flash chromatography (Biotage System, SNAP Cartridge silica 100 g, eluent: gradient n-hexane/ethyl acetate 88/12 (150 ml), to ethyl acetate during 1500 ml, ethyl acetate (300 ml)). The product (0.4 g) was obtained.

Z) 1-(2,3-bis(nitrooxy)propyl)4-(2-((9R,10S,11S, 13S,16R,17S)-9-fluoro-11-hydroxy-16,17-((1-methylethylidene)bis(oxy))-10,13-dimethyl-3-oxo-6,7,8, 9,10,11,12,13,14,15,16,17-dodecahydro-3H-cyclopenta[a]phenanthren-17-yl)-2-oxoethyl)2-aminosuccinate Hydrochloride

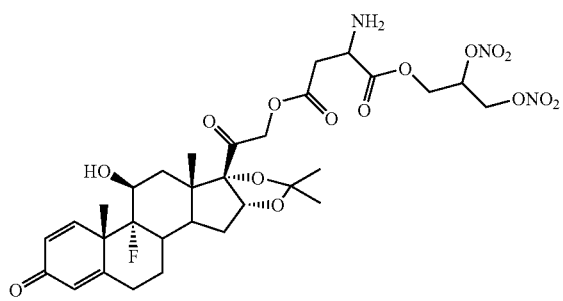

A solution of compound Y (0.4 g, 0.49 mmol) in dichloromethane (8 ml) was stirred at room temperature. HCl gas was buddle in the solution for 15 minutes. The solvent evaporated under vacuum. The residue was purified by reverse phase flash chromatography (Biotage column FLASH 25+M™, eluent: water/acetonitrile 1/1. The product (0.13 g) was obtained $^1$H-NMR: (DMSO), δ: 7.30 (1H, d); 6.23 (1H, dd); 6.02 (1H, s); 5.66 (1H, m); 5.49 (1H, m); 5.17 (1H, dd), 4.97 (1H, dd); 4.89-4.79 (3H, m); 4.48 (1H, dm); 4.38 (1H, dd), 4.20 (1H, m); 3.82 w (1H, m); 2.78 (1H, dm); 2.68-2.49 (7H, m); 2.10-1.75 (3H, m); 1.54 (1H, m); 1.49 (5H, m); 1.35 (4H, m); 1.15 (3H, s); 0.83 (3H, s).

The invention claimed is:

1. A compound of formula (I) and pharmaceutically acceptable salts or stereoisomers thereof $$R—(Z)_a—R_x \quad (I)$$

wherein R is a corticosteroid residue of formula (II):

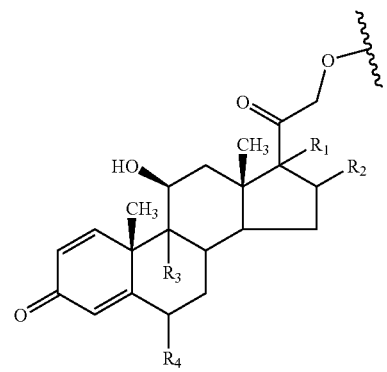

wherein:

$R_1$ and $R_2$ are taken together to form a group of formula (III)

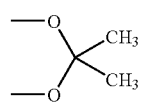

$R_3$ is F and $R_4$ is H, $R_1$, $R_2$ and $R_3$ are in position α;
wherein
a=0 and Z is absent,
$R_x$ is $$C(O)—CH(R^1)—NH-(T'—Y—ONO_2)$$

wherein
$R^1$ is H
T' is —C(O)—;
Y is selected from
a)
  a straight or branched $C_1$-$C_{10}$ alkylene,
  a straight or branched $C_1$-$C_{10}$ alkylene substituted with a —$ONO_2$ group.

2. A compound of formula (I) according to claim 1 and pharmaceutically acceptable salts or stereoisomers thereof selected from the group consisting of:

(3)

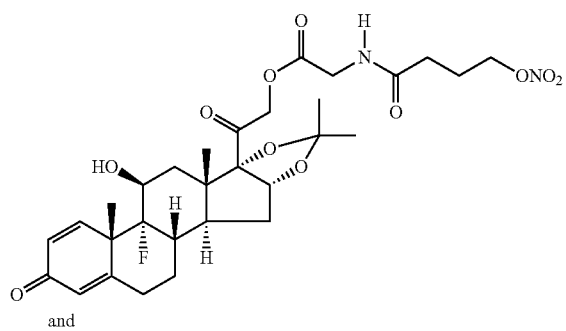

and

-continued (5)

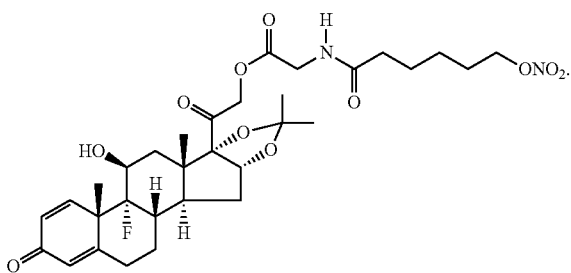

3. A medicament comprising a compound of formula (I) according to claim 1.

4. A method of treating an ocular disease comprising administering to a subject the compound of formula (I) according to claim 1, wherein the ocular disease is selected from the group consisting of: ocular hypertension, age-related macular degeneration, diabetic macular edema, diabetic retinopathy, hypertensive retinopathy and retinal vasculopathies.

5. A method of treating a respiratory disease, selected from asthma or chronic obstructive pulmonary disease (COPD), comprising administering to a subject the compound of formula (I) according to claim 1.

6. A method of treating a dermatological disease, comprising administering to a subject the compound of formula (I) according to claim 1, wherein the dermatological disease is selected from the group consisting of: dermatosis, atopic dermatitis, inflammation, eczema, erythema, papulation, scaling, erosion, oozing, crusting, pruritis, psoriasis, epidermalysis bullosa, erythema, hidradenitis suppurative, warts, diaper rash, and jock itch.

7. A pharmaceutical formulation comprising at least a compound of formula (I) as described in claim 1 and one or more pharmaceutical acceptable excipients.

* * * * *